US008207114B2

(12) United States Patent
LeBowitz et al.

(10) Patent No.: US 8,207,114 B2
(45) Date of Patent: *Jun. 26, 2012

(54) TARGETED THERAPEUTIC PROTEINS

(75) Inventors: Jonathan H. LeBowitz, Whitefish Bay, WI (US); Stephen M. Beverley, Clayton, MO (US); William S. Sly, St. Louis, MO (US)

(73) Assignee: Biomarin Pharmaceutical Inc., Novato, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 12/610,596

(22) Filed: Nov. 2, 2009

(65) Prior Publication Data
US 2010/0075906 A1    Mar. 25, 2010

Related U.S. Application Data

(63) Continuation of application No. 10/981,267, filed on Nov. 3, 2004, now Pat. No. 7,629,309, which is a continuation-in-part of application No. 10/272,531, filed on Oct. 16, 2002, now abandoned, and a continuation-in-part of application No. 10/272,483, filed on Oct. 16, 2002, now Pat. No. 7,560,424, and a continuation-in-part of application No. PCT/US03/17211, filed on May 29, 2003.

(60) Provisional application No. 60/516,990, filed on Nov. 3, 2003, provisional application No. 60/384,452, filed on May 29, 2002, provisional application No. 60/408,816, filed on Sep. 6, 2002, provisional application No. 60/445,734, filed on Feb. 6, 2003, provisional application No. 60/386,019, filed on Jun. 5, 2002.

(51) Int. Cl.
*A61K 38/30* (2006.01)
*A61K 38/00* (2006.01)
*A61K 38/43* (2006.01)
*C07K 14/65* (2006.01)

(52) U.S. Cl. ........... 514/8.6; 514/1.1; 514/8.5; 530/399; 424/94.1

(58) Field of Classification Search .................. None
See application file for complete search history.

(56) References Cited

U.S. PATENT DOCUMENTS

| | | | |
|---|---|---|---|
| 4,309,776 A | 1/1982 | Berguer |
| 4,522,811 A | 6/1985 | Eppstein et al. |
| 4,749,570 A | 6/1988 | Poznansky |
| 4,801,575 A | 1/1989 | Pardridge |
| 4,902,505 A | 2/1990 | Pardridge et al. |
| 5,236,838 A | 8/1993 | Rasmussen et al. |
| 5,258,453 A | 11/1993 | Kopecek et al. |
| 5,356,804 A | 10/1994 | Desnick et al. |
| 5,399,346 A | 3/1995 | Anderson et al. |
| 5,405,942 A | 4/1995 | Bell et al. |
| 5,470,828 A | 11/1995 | Ballard et al. |
| 5,476,779 A | 12/1995 | Chen et al. |
| 5,549,892 A | 8/1996 | Friedman et al. |
| 5,580,757 A | 12/1996 | Desnick et al. |
| 5,633,234 A | 5/1997 | August et al. |
| 5,633,235 A | 5/1997 | Townsend et al. |
| 5,704,910 A | 1/1998 | Humes |
| 5,736,363 A | 4/1998 | Edwards et al. |
| 5,798,366 A | 8/1998 | Platt et al. |
| 5,817,623 A | 10/1998 | Ishii |
| 5,817,789 A | 10/1998 | Heartlein et al. |
| 5,827,703 A | 10/1998 | Debs et al. |
| 5,854,025 A | 12/1998 | Edwards et al. |
| 5,977,307 A | 11/1999 | Friden et al. |
| 5,981,194 A | 11/1999 | Jefferies et al. |
| 6,020,144 A | 2/2000 | Gueiros-Filho et al. |
| 6,027,921 A | 2/2000 | Heartlein et al. |
| 6,066,626 A | 5/2000 | Yew et al. |
| 6,083,725 A | 7/2000 | Selden et al. |
| 6,118,045 A | 9/2000 | Reuser et al. |
| 6,226,603 B1 | 5/2001 | Freire et al. |
| 6,235,874 B1 | 5/2001 | Wu et al. |
| 6,262,026 B1 | 7/2001 | Heartlein et al. |
| 6,270,989 B1 | 8/2001 | Treco et al. |
| 6,273,598 B1 | 8/2001 | Keck et al. |
| 6,281,010 B1 | 8/2001 | Gao et al. |
| 6,284,875 B1 | 9/2001 | Turpen et al. |
| 6,329,501 B1 | 12/2001 | Smith et al. |
| 6,344,436 B1 | 2/2002 | Smith et al. |
| 6,348,194 B1 | 2/2002 | Huse et al. |
| 6,441,147 B1 | 8/2002 | Turpen et al. |
| 6,451,600 B1 | 9/2002 | Rasmussen et al. |
| 6,455,494 B1 | 9/2002 | Jefferies et al. |
| 6,472,140 B1 | 10/2002 | Tanzi et al. |

(Continued)

FOREIGN PATENT DOCUMENTS
EP        0196056 A2    10/1986
(Continued)

OTHER PUBLICATIONS

"Purification," The QIAexpressionist, pp. 63-107 (2001).
"QIAexpress Protein Purification System "QIAexpress—The Complete System for 6xHis Technology pp. 7-12, (2001).
Achord et al., "Human β-Glucuronidase. II. Fate of Infused Human Placental β-Glucuronidase in the Rat," Pediat. Res., 11:816-822 (1977).
Achord, et al., "Human β-Glucuronidase: In Vivo Clearance and in Vitro Uptake by a Glycoprotein Recognition System on Reticuloendothelial Cells" Cell, 15:269-278 (1978).

(Continued)

*Primary Examiner* — Daniel C Gamett
(74) *Attorney, Agent, or Firm* — Marshall, Gerstein & Borun LLP

(57) ABSTRACT

Targeted therapeutics that localize to a specific subcellular compartment such as the lysosome are provided. The targeted therapeutics include a therapeutic agent and a targeting moiety that binds a receptor on an exterior surface of the cell, permitting proper subcellular localization of the targeted therapeutic upon internalization of the receptor. Nucleic acids, cells, and methods relating to the practice of the invention are also provided.

3 Claims, 37 Drawing Sheets

U.S. PATENT DOCUMENTS

| | | |
|---|---|---|
| 6,537,785 B1 | 3/2003 | Canfield |
| 6,566,099 B1 | 5/2003 | Selden et al. |
| 6,569,661 B1 | 5/2003 | Qin et al. |
| 6,596,500 B1 | 7/2003 | Kang et al. |
| 7,396,811 B2 | 7/2008 | LeBowitz et al. |
| 2001/0006635 A1 | 7/2001 | Bennett et al. |
| 2001/0025026 A1 | 9/2001 | Heartlein et al. |
| 2002/0013953 A1 | 1/2002 | Reuser et al. |
| 2002/0081654 A1 | 6/2002 | Sandrin et al. |
| 2002/0110551 A1 | 8/2002 | Chen |
| 2002/0142299 A1 | 10/2002 | Davidson et al. |
| 2003/0004236 A1 | 1/2003 | Meade |
| 2003/0021787 A1 | 1/2003 | Hung et al. |
| 2003/0077806 A1 | 4/2003 | Selden et al. |
| 2003/0082176 A1 | 5/2003 | LeBowitz et al. |
| 2004/0005309 A1 | 1/2004 | LeBowitz et al. |
| 2004/0006008 A1 | 1/2004 | LeBowitz et al. |
| 2004/0029779 A1 | 2/2004 | Zhu et al. |
| 2004/0081645 A1 | 4/2004 | Van Bree et al. |
| 2004/0248262 A1 | 12/2004 | Koeberl et al. |
| 2005/0026823 A1 | 2/2005 | Zankel et al. |
| 2005/0058634 A1 | 3/2005 | Zhu |
| 2005/0281805 A1 | 12/2005 | LeBowitz et al. |

FOREIGN PATENT DOCUMENTS

| | | |
|---|---|---|
| EP | 0466222 A1 | 1/1992 |
| EP | 0599303 A2 | 6/1994 |
| WO | WO-9104014 A1 | 4/1991 |
| WO | WO-9114438 A1 | 10/1991 |
| WO | WO-9222332 A2 | 12/1992 |
| WO | WO-9306216 A1 | 4/1993 |
| WO | WO-9310819 A1 | 6/1993 |
| WO | WO-9402178 A1 | 2/1994 |
| WO | WO-9502421 A1 | 1/1995 |
| WO | WO-0053730 A2 | 9/2000 |
| WO | WO-0119955 A2 | 3/2001 |
| WO | WO-0153730 A1 | 7/2001 |
| WO | WO-02044355 A2 | 6/2002 |
| WO | WO-0256907 A2 | 7/2002 |
| WO | WO-02087510 A2 | 11/2002 |
| WO | WO-03032727 A1 | 4/2003 |
| WO | WO-03032913 A2 | 4/2003 |
| WO | WO-03057179 A2 | 7/2003 |
| WO | WO-03102583 A1 | 12/2003 |
| WO | WO-2005078077 A2 | 8/2005 |

OTHER PUBLICATIONS

Aeed and Elhammer, "Glycosylation of recombinant prorenin in insect cells: the insect cell line Sf9 does not express the mannose 6-phosphate recognition signal. Glycosylation of recombinant prorenin in insect cells: the insect cell line Sf9 does not express the mannose", Biochemistry, 33(29):8793-0797 (1994).

Aerts et al., "Efficient Routing of Glucocerebrosidase to Lysosomes Requires Complex Oligosaccharide Chain Formation," Biochem. Biophys. Res. Commun., 141(2):452-458 (1986).

Allen et al., "Metabolic Correction of Fucosidosis Lymphoid Cells by Galaptin- -L-Fucosidase Conjugates," Biochem. Biophys. Res. Communi., 172(1):335-340 (1990).

Amalfitano et al., "Recombinant Human Acid Alpha-Glucosidase Enzyme Therapy for Infantile Glycogen Storage Disease Type II: Results of a Phase I/II Clinical Trial," Genet. Med. 3(2):132-138 (2001).

Anand, "The Cure", HarperCollins, New York, NY, Chapter 23, pp. 257-268 (2006).

Arai et al., "Conformations of Variably Linked Chimeric Proteins Evaluated by Synchrotron X-ray Small-Angle Scattering," Proteins: Structure, Function, and Bioinformatics, 57:829-838 (2004).

Armstrong et al., "Uptake of Circulating Insulin-Like Growth Factor-I Into the Cerebrospinal Fluid of Normal and Diabetic Rats and Normalization of 1GF-II mRNA Content in Diabetic Rat Brain," Journal of Neuroscience Research, 59:649-660 (2000).

Auletta et at, "Receptor-mediated endocytosis and degradation of insulin-like growth factor I and II in neonatal rat astrocytes", Journal of Neuroscience Research, 31:14-20 (1992).

Authier et al., "In vitro endosome-lysosome transfer of dephosphorylated EGF receptor and She in rat liver," FEBS Letters, 00:25-31 (1999).

Bach et al., "Binding of Mutants of Human Insulin-like Growth Factor II to Insulin-like Growth Factor Binding Proteins 1-6," J. Biol. Chem., 268(12):9246-9254 (1993).

Bartlett et al., "CAVEAT: A Program to Facilitate the Structure-derived Design of Biologically Active Molecules," in Molecular Recognition: Chemical and Biological Problems, 182-196 (1989).

Barton et al., "Therapeutic response to intravenous infusions of glucocerebrosidase in a patient with Gaucher disease," Proc Natl Acad Sci USA, 85(5):1913-1916 (Mar. 1990).

Baxter, "Insulin-like Growth Factor (IGF)-Binding Proteins: Interactions with IGFs and Intrinsic Bioactivities." Am. J. Physiol. Endocrinol. Metab., 278(6)967-976 (2000).

Becker et al., "HLA and Mate Choice," J. Hum. Genet., 62:991 (1998).

Beljaars et al., "Characteristics of the hepatic stellate cell-selective carrier mannose 6-phosphate modified albumin (M6P28-HSA)," LIVER, 21:320-328 (2001).

Beutler et al., "Gaucher Disease," in The Metabolic and Molecular Bases of Inherited Disease, $8^{th}$ ed., 3635-3668 (2001).

Bickel et al., "Delivery of Peptides and Proteins through the Blood-Brain Barrier," Advanced Drug Delivery Reviews 46(1-3):247-279 (2001).

Bijsterbosch et al., "Native and Modified Lipoproteins as Drug Delivery Systems," Advanced Drug Delivery Reviews, 5:231-251 (1990).

Bijvoet et al., "Expression of cDNA-Encoded Human Acid Alpha-Glucosidase in Milk of Transgenic Mice," Biochim. Biophys. Acta, 1308(2):93-96 (1996).

Bijvoet et al., "Human Acid Alpha-Glucosidase from Rabbit Milk Has Therapeutic Effect in Mice with Glycogen Storage Disease Type II," Hum. Mol. Genet., 8(12):2145-2153 (1999).

Bijvoet et al., "Recombinant Human Acid Alpha-Glucosidase: High Level Production in Mouse Milk, Biochemical Characteristics, Correction of Enzyme Deficiency in GSDII KO Mice," Hum. Mol. Genet., 7(11):1815-1824 (1998).

Birkenmeier et al., "Increased Life Span and Correction of Metabolic Defects in Murine Mucopolysaccharidosis Type VII after Syngeneic Bone Marrow Transplantation," Blood, 78(111:3081-3092 (1991).

Birkenmeier et al., "Murine Mucopolysaccharidosis Type VII; Characterization of a Mouse with β-Glucuronidase Deficiency," J. Clin. Invest., 83(4):1258-1266 (1989).

Bishop et al., "Human α-Galactosidase Characterization and Eukaryotic Expression of the Full-length cDNA and Structural Organization of the Gene," in Lipid Storage Disorders Biological and Medical Aspects, vol. 150:809-822 (1987).

Blakey et al., "Effect of Chemical Deglycosylation of Ricin A Chain on the in Vivo Fate and Cytotoxic Activity of an Immunotoxin Composed of Ricin A Chain and Anti-Thy 1.1 Antibody," Cancer Research, 47:947-952 (1987).

Brady et al., "Enzyme replacement therapy in Fabry disease," J. Inherit, Metab. Dis., 24:18-24 (2001).

Braulke, "Type-2 IGF Receptor: A Multi-Ligand Binding Protein," Horm. Metab. Res., 31:242-246 (1999).

Brooks et al., "Functional correction of established central nervous system deficits in an animal model of lysosomal storage disease with feline immunodeficiency virus-based vectors," PNAS Early Editiion, 1-6 (2002).

Brooks, "Immune Response to Enzyme Replacement Therapy in Lysosomal Storage Disorder Patients and Animal Models," Mol. Genet. Metab., 68:268-275 (1999).

Brown et al., "Structure of a Functional IGF2R Fragment Determined from the Anomalous Scattering of Sulfur," EMBO J., 21(5):1054-1062 (2002).

Bungard, Design of Prodrugs, pp. 7-9, 21-24, Elsevier, Amsterdam (1985).

Burgisser et al., "Mutants of Human Insulin-like Growth Factor II with Altered Affinities for the Type 1 and Type 2 Insulin-like Growth Factor Receptor," J. Biol. Chem., 266(2):1029-1033 (1991).

Cacciari et al., "Somatomedin C in Pediatric Pathophysiology," Pediatrician, 14:146-153 (1987).

Calhoun et al., "Fabry Disease: Isolation of a cDNA Clone Encoding Human-Galactosidase A," Proc. Natl. Acad. Sci. USA, 82:7364-7368 (1985).

Cascieri et al., "Structural Analogs of Human Insulin-like Growth Factor (IGF) I with Altered Affinity for Type 2 IGF Receptors," J. Biol. Chem., 264(4):2199-2202 (1999).

Chodobski et al., "Choroid Plexus: Target for Polypeptides and Site of Their Synthesis," Microscopy Research and Technique, 52:65-82 (2001).

Connolly-Martin, "Computer-Assisted Rational Drug Design," Methods in Enzymology 203:587-613 (1991).

Dahms et al., "Mannose 6-Phosphate Receptors and Lysosomal Enzyme Targeting," The Journal of Biological Chemistry, 264(21): 12115-12118 (1989).

Daly et al., "Neonatal Gene Transfer Leads to Widespread Correction of Pathology in a Murine Model of Lysosomal Storage Disease," Proc. Natl. Acad. Sci. USA 96(5):2296-2300 (1999).

Desnick et al., "Enzyme Replacement and Enhancement Therapies: Lessons from Lysosomal Disorders", Nature Reviews Genetics, 3:954-966 (Dec. 2002).

Devedjian et al., "Transgenic mice overexpressing insulin-like growth factor-II in f3 cells develop type 2 diabetes," The Journal of Clinical Investigation 105(6):731-740 (2000).

Devi et al., "An Insulin-Like Growth Factor II (IGF-II) Affinity-Enhancing Domain Localized within Extracytoplasmic Repeat 13 of the IGF-II/Mannose 6-Phosphate Receptor," Molecular Endocrinology, 12(11):1661-1672 (1998).

Difalco et al., "Efficacy of an Insulin-Like Growth Factor-Interleukin-3 Fusion Protein in Reversing the Hematopoietic Toxicity Associated with Azidothymidine in Mice," The Journal of Pharmacology and Experimental Therapeutics, 284:449-454 (1998).

Difalco et al., "Preparation of a recombinan chimaera of insulin-like growth factor II and interleukin 3 with highproliferative potency for haemopoietic cells," Biochem. J., 326:407-413 (1997).

Diment et al., "Generation of Macrophage Variants with 5-Azacytidine: Selection for Mannose Receptor Expression," J. Leukocyte Biol. 42:485-490 (1987).

Dixon, "Computer-Aided Drug Design: Getting the Best Results," TIBTECH, 10:357-363 (1992).

Dobrenis et al., "Neuronal Lysosomal Enzyme Replacement Using Fragment C of Tetanus Toxin," Proc. Natl. Acad. Sci. USA, 89:2297-2301 (1992).

Douglass et al., "Chemical Deglycosylation Can Induce Methylation, Succinimide Formation, and Isomerization " J. Protein Chem., 20(7):571-576 (2001).

Duguay et al., "Post-translational Processing of the Insulin-like Growth Factor-2 Precursor," J. Biol. Chem., 273(29):18443-18451 (1998).

Dziegielewska et al., "The ins and outs of brain-barrier mechanisms," Trends in Neurosciences, 25(2):69-71 (2002).

Eisen et al., "HOOK: A Program for Finding Novel Molecular Architectures That Satisfy the Chemical and Steric Requirements of a Macromolecule Binding Site " Proteins: Structure, Function, and Genetics, 19:199-221 (1994).

European Search Report for EP02801739 (2005).

European Search Report for EP08000935 (2008).

European Supplementary Partial Search Report for European Application No. EP 03 73 6779 (Date of mailing Apr. 5, 2007).

Forbes et al., "Contribution of Residues A54 and L55 of the Human Insulin-like Growth Factor-II (IGF-II) A Domain to Type 2 IGF Receptor Binding Specificity," Growth Factors, 19:163-173 (2001).

Foxwell, et al., "The Preparation of Deglycosylated Ricin by Recombination of Glycosidase Treated A- and B-Chains: Effects of Deglycosylation on Toxicity and in vivo Distribution," Biochemica et Biophysica Acta, 923:59-65 (1987).

Friden et al., "Anti-Transferrin Receptor Antibody and Antibody-Drug Conjugates Cross the Blood-Brain Barrier," Proc. Natl. Acad. Sci. USA, 88:4771-4775 (1991).

Fukuda et al., "Dysfunction of Endocytic and Autophagic Pathways in a Lysosomal Storage Disease, " AIM. Neurol., 59(4):700-708 (2006).

Fukuda et al., "Autophagy and Lysosomes in Pompe Disease," Autophagy, 2(4):318-320 (2006).

Fukuda et al., "Autophagy and Mistargeting of Therapeutic Enzyme in Skeletal Muscle in Pompe Disease," Mol. Therapy, 14(6):831-839 (2006).

Fukuta et al., "Insulin Fragments as a Carrier for Peptide Delivery Across the Blood-Brain Barrier," Pharmaceutical Research, 11(12):1681-1688 (1994).

Godar et al., "M6P/IGFII-Receptor Complexes Urokinase Receptor and Plasminogen for Activation of Transforming Growth Factor-β1," Eur. J. Immunol., 29:1004-1013 (1999).

Golden et al., "Human Blood-Brain Barrier Leptin Receptor," J. Clin. Invest., 99(1):14-18 (1997).

Gozes et al., "Neuropeptides: brain messengers of many faces," TRENDS in Neurosciences, 24(12):687-690 (2001).

Grimme et al., "Endocytosis of Insulin-like Growth Factor II by a Mini-receptor Based on repeat 11 of the Mannose 6-Phosphate/Insulin-like Growth Factor II Receptor," J. Biol. Chem., 275(43):33697-33703 (2000).

Grubb et al., "Large Scale Purification of Phosphorylated Recombinant β-Glucuronidase from Over-Expressing Mouse L Cells," Fed. Am. Soc. Exp. Biol. 7:1255a (1993).

Hashimoto et al., "Binding Sites and Binding Proteins of Binary and Ternary Complexes of Insuline-like Growth Factor II (IGF-II), IGF-binding Protein-3, and Acid-labile Subunit," J. Biol. Chem., 272(44):27936-42 (1997).

Hashimoto et al., "N-terminal Deletion Mutants of Insulin-like Growth Factor-II (IGF-II) Show Thr7 and Leu8 Important for Binding to Insulin and IGF-I Receptors and Leu8 Critical for All IGF-II Functions," J. Biol. Chem., 270(30):18013-18018 (1995).

Haskell et al., "Intracellular Trafficking of the JNCL Protein CLN3," Molecular Genetics and Metabolism, 66:253-260 (1999).

Henikoff and Henikoff, "Amino acid substitution matrices from protein blocks," PNAS, 89:10915-10919 (1992).

Hickman et al., "A Recognition Marker Required tor Uptake of a Lysosomal Enzyme by Cultured Fibroblasts," BBRC, 57:55-61 (1974).

Hirschhorn et al., "Glycogen Storage Disease Type II: Acid α-Glucosidase (Acid Maltase) Deficiency," in The Metabolic and Molecular Basis of Inherited Disease, 8th ed., 3389-3420 (2001).

Hoefsloot et al., "Expression and Routeing of Human Lysosomal Alpha-Glucosidase in Transiently Transfected Mammalian Cells," Biochem. J., 272 (2):485-492 (1990).

Houba et al., "Improved Characteristics of a Human β-Glucuronidase—Antibody Conjugate after Deglycosylation for Use in Antibody-Directed Enzyme Prodrug Therapy," Bioconiugate Chem. 7:606-611 (1996).

International Search Report for PCT/US02/13835 (2002).

International Search Report for PCT/US02/32968 (2002).

International Search Report for PCT/US02/32996 (2002).

International Search Report for PCT/US03/17211 (2003).

International Search Report for PCT/US2007/023881 (2009).

Ishibashi et al., "Asialoglycoprotein Receptor Deficiency in Mice Lacking the Minor Receptor Subunit," J. Biol. Chem. 269(45):27803-27806 (1994).

Islam et al., "C-terminal Processing of Human β-Glucuronidase," J. Biol. Chem., 268(30): 22627-22633 (Oct. 1993).

Jacob et al., "Sucrase Is an Intramolecular Chaperone Located at the C-terminal End of the Sucrase-Isomaltase Enzyme Complex," J. Biol. Chem., 277:32141 (2002).

Journet et al., Proteomic analysis of human lysosomes: Application to monocytic and breast cancer cells, Proteomics 2, 1026-1040 (2002).

Juuti-Uusitalo et al., "Selective Targeting of Avidin/Mannose 6-Phosphate Receptor Chimeras to Early or Late Endosomes," European Journal of Cell Biology, 79:458-468 (2000).

Kang et al., "Mannose 6-Phosphate/Insulin-like Growth Factor II Receptor Mediates the Growth-Inhibitory Effects of Retinoids," Cell Growth & Differentiation, 10:591-600 (1999).

Kang et al., "Mannose-6-phosphate/Insulin-like Growth Factor-II Receptor is a Receptor for Retinoic Acid," Proc. Natl. Acad. Sci. USA, 95:13671-13676 (1998).

Kang et al., "Retinoic Acid Alters the Intracellular Trafficking of the Mannose-6 Phosphate/Insulin-like Growth Factor II Receptor and Lysosomal Enzymes," Proc. Natl. Acad. Sci. USA 95:13687-13691 (1998).

Kerr et al., "Comparison of recombinant and synthetically formed monoclonal antibody beta lactamase conjugates for anticancer prodrug activation," Bioconjugate Chemistry, 10:1084-1089 (1999).

Kiess et al., "Biochemical Evidence that the Type II Insulin-like Growth Factor Receptor Is Identical to the Cation-independent Mannose 6-Phosphate Receptor," J. Biol. Chem., 263:9339-9344 (1988).

Kiess et al., "Insulin-Like Growth Factor II (IGF-II) and the IGF-II/Mannose-6-Phosphate Receptor: the Myth Continues," Horm. Res., 41(suppl. 2):66-73 (1994).

Kiess et al., "Insulin-Like Growth Factor II (IGF-II) Inhibits Both the Cellular Uptake of ?-Galactosidase and the Binding of ?-Galactosidase to Purified IGF-II/Mannose 6-Phosphate Receptor," The Journal of Biological Chemistry, 264(8):4710-4714 (1989).

Kikuchi et al., "Clinical and Metabolic Correction of Pompe Disease by Enzyme Therapy in Acid Maltase-Deficient Quail," J. Clin. Invest. 101(4):827-833 (1998).

Kim et al., "High-Level Expression and Simple Purification of Recombinant Human Insulin-Like Growth Factor I," Journal of Biotechnology, 48:97-105 (1996).

Kishani et al., "Recombinant human acid-glucosidase, Major Clinical Benefits in Infantile-Onset Pompe Disease," Neurology, 68:99-109 (2007).

Kishnani et al., "A Retrospective, Multilational, Multicenter Study on the Natural History of Infantile-Onset Pompe Disease," J Pediatr, 148:671-6 (2006).

Kishnani et al., "Chinese Hamster Ovary Cell-Derived Recombinant Human Acid-Glucosidase in Infantile-Onset Pompe Disease," J Pediatr, 148:671-6 (2006).

Korner et al., "Mannose 6-Phosphate/Insulin-like Growth Factor II Receptor Fails to Interact with G-proteins," The Journal of Biological Chemistry, 270(1):287-295 (1995).

Kundra et al., "Asparagine-linked Oligosaccharides Protect Lamp-1 and Lamp-2 from Intracellular Proteolysis," J. Biol. Chem., 274(43):31039-31046 (1999).

Langford et al., "Leishmania: Codon Utilization of Nuclear Genes," Experimental Parasitology, 74:360-361 (1992).

Lau et al., "Loss of the Imprinted IGF2/Cation-Independent Mannose 6—Phosphate Receptor Results in Fetal Overgrowth and Perinatal Lethality," Genes & Development 8(24):2953-2963 (1994).

Lebowitz et al., "Glycosylation-independent targeting enhances enzyme delivery to lysosomes and decreases storage in mucopolysaccharidosis type VII mice," PNAS USA, 101:3083-3088 (2004).

Lebowitz, "A breach in the blood-brain barrier," PNAS, 102(41):14485-14486 (2005).

Lee et al., "Mannose Receptor—Mediated Regulation of Serum Glycoprotein Homeostasis," Science, 295:1898-1901 (2002).

Lemansky et al., "Synthesis and Processing of a-Galactosidase A in Human Fibroblasts," J. Biol. Chem., 262:2062-2065 (1987).

Linnell et al., "Real Time Kinetics of Insulin-like Growth Factor II (IGF-II) Interaction with the IGF-II/Mannose 6-Phosphate Receptor," The Journal of Biological Chemistry, 276(26):23986-23991, (2001).

Liu et al., "Intranasal administration of insulin-like growth factor-I bypasses the blood-brain barrier and protects against focal cerebral ischemic damage," Journal of the Neurological Sciences, 187: 91-97 (2001).

Ludwig et al., "Mouse Mutants Lacking the Type 2 IGF Receptor (IGF2R) Are Rescued from Perinatal Lethality in Igf2 and Igflr Null Backgrounds," Developmental Biology, 177(2):517-535, (1996).

Ludwig et al., "Roles for Mannose-6-Phosphate Receptors in Lysosomal Enzyme Sorting, IGF-II Binding and Clathrin-Coat Assembly," Trends in Cell Biology, 5:202-206 (1995).

Luthi et al., "Mutants of Human Insulin-like Growth Factor II (IGF II) Expression and Characterization of Truncated IGF II and of Two Naturally Occurring Variants," Eur. J. Biochem. 205(2):483-490 (1992).

Lynch et al., "High-resolution Light Microscopy (HRLM) and Digital Analysis of Pompe Disease Pathology," J. Histochem. Cytochem., 53:63-73 (2005).

Magee et al., "Insulin-like Growth Factor I and Its Binding Proteins: A Study of the Binding Interface Using B-Domain Analogues," Biochemistry, 38(48):15863-15870 (1999).

Mah et al., "Physiological Correction of Pompe Disease by Systemic Delivery of Adeno-associated Virus Serotype 1 Vectors," Molecular Thereapy (online publication) (2007).

Mahuran et al., "Proteolytic Processing of Pro-A and Pro-B Precursors from Human B-Hexosaminidase," J. Biol. Chem., 263:4612-4618 (1988).

Martiniuk et al., "Correction of Glycogen Storage Disease Type II by Enzyme Replacement with a Recombinant Human Acid Maltase Produced by Over-Expression in a CHO-DHFR(neg) Cell Line," Biochem. Biophys. Res. Commun., 276(3):917-923 (2000).

Martiniuk et al., "Recombinant Human Acid-Glucosidase Generated in Bacteria: Antigenic, but Enzymatically Inactive," DNA and Cell Biology, 11(9):701-706 (1992).

Mazzolla et al., "Enhanced Resistance to *Cryptococcus neoformans* Infection Induced by Chloroquine in a Murine Model of Meningoencephalitis," Antimicrobial Agents and Chemotherapy, 41:802-807 (1997).

Meynial-Salles et al., "In vitro glycosylation of proteins: An enzymatic approach," J. Biotechnology, 1-14 (1996).

Moreland et al., "Lysosomal Acid-Glucosidase Consists of Four Different Peptides Processed from a Single Chain Precursor," J. Biol. Chem, 280:6780-6791 (2005).

Morgan et al., "Insulin-like Growth Factor II Receptor as a Multifunctional Binding Protein," Nature 329(6137):301-307 (1987).

Myszka, "Kinetic, Equilibrium, and Thermodynamic Analysis of Macromolecular Interactins with BIACORE," Methods Enzymol., 323:325-340 (2000).

Newrzella et al., "Functional analysis of the glycosylaton of murine acid sphingomyenlinase," J. Biol. Chem., 271:32089-32095 (1996).

Nilsson et al., N. Engl. J. Med., 318:947-50 (1988).

Nissley at al., "Reciprocal modulation of binding of lysosomal enzymes and insulin-like growth factor-II (IGF-II) to the mannose 6-phosphate/IGF-II receptor," Adv. Exp. Med. Biol., 293:311-324 (1991).

Niwa et al., "Efficient Selection for High-Expression Transfectants with a Novel Eukaryotic Vector," Gene 108:193-200 (1991).

Nolan et al., "Binding of Insulin-Like Growth Factor II (IGF-II) by Human Cation-Independent Mannose 6-Phosphate Receptor/IGS-II Receptor Express in Receptor-Deficient Mouse L Cells," Cell Regulation, 1(2):197-213 (Jan. 1990).

Novazyme Website printouts (2001).

Nykjaer et al., "Mannose 6-Phosphate/Insulin-like Growth Factor-II Receptor Targets the Urokinase Receptor to Lysosomes via a Novel Binding Interaction," The Journal of Cell Biology 141(3):815-828 (1998).

O'Connor et al., "Enzyme Replacement Therapy for Murine ucopolysaccharidosis Type VII Leads to Improvements in Behavior and Auditory Function," J. Clin. Invest., 101:1394-1400 (1998).

O'Dell et al., "Molecules in Focus Insulin-like Growth Factor II (IGF-II)," The International Journal of Biochemistry & Cell Biology, 30(7): 767-771 (1998).

Oksche et al., "Late Endosomal/Lysosomal Targeting and Lack of Recycling of the Ligand-Occupied Endothelin B Receptor," Molecular Pharmacology 57:1104-1113 (2000).

Paasche et al., "Mechanisms of Endothelin Receptor Subtype-specific Targeting to Distinct Intracellular Trafficking Pathways," The Journal of Biological Chemistry, 276(36):34041-34050 (2001).

Pardridge, "Drug Delivery to the Brain," Journal of Cerebral Blood Flow and Metabolism, 17:713-731 (1997).

Pardridge, "Targeting Neurotherapeutic Agents Through the Blood-Brain Barrier," Arch Neural., 59: 35-40 (2002).

Pauly et al., "Complete correction of acid-glucosidase deficiency in Pompe disease fibroblasts in vitro, and lysosomally targeted expression in neonatalrat cardiac and skeletal muscle," Gene Therapy, 5:473-480 (1998).

PCT International Preliminary Report on Patentability for International Application No. PCT/US05/004286 (Date of issuance Aug. 14, 2006).
PCT International Search Report for International Application No. PCT/US05/004286 (Date of mailing Aug. 31, 2005).
Pine, Organic Chemistry, 5th ed., McGraw Hill, p. 770 (1987).
Poznansky et al., "Enzyme Replacement Therapy in Fibroblasts from a Patient with Cholesteryl Ester Storage Disease," FASEB J., 3:152-156 (1989).
Prince et al., "Lipoprotein Receptor Binding, Cellular Uptake, and Lysosomal Delivery of Fusions between the Receptor-associated Protein (RAP) and-L-Iduronidase or Acid-Glucosidase," J. Biol. Chem., 279(33):35037-35046 (2004).
Pulford et al., "Uptake of Circulating Insulin-Like Growth Factors (IGFs) into Cerebrospinal Fluid Appears to Be Independent of the IGF Receptors as Well as IGF-Binding Proteins" Endocrinology, 142(1):213-220 (2001).
Raben et al., "Acid-Glucosidase Deficiency (Glycogenosis Type II, Pompe Disease)," Current Molecular Medicine, 2:145-166 (2002).
Raben, JBC, 273:19086-19092 (1998).
Ramalingam et al., "Binding to the transferrin receptor is required for endocytosis of HFE and regulation of iron homeostasis," Nature Cell Biology, 2(12):953-957 (2000).
Reinherdt and Bondy, "Insulin-Like Growth Factors Cross the Blood-Brain Barrier," Endocrinology, 135:1753-1761 (1994).
Reuser et al., "Biochemical, Immunological, and Cell Genetic Studies in Glycogenosis Type II," Am. J. Hum. Genet. 30(2):132-143 (1978).
Rhee et al., "High-level expression of human insulin-like growth factor II in *Escherichia coli*," Journal of Biotechnology, 13:293-304 (1990).
Rocca et al., "Involvement of the Ubiquitin/Proteasome System in Sorting of the Interleukin 2 Receptor β Chain to Late Endocytic Compartments," Molecular Biology of the Cell, 12:1293-1301 (2001).
Rohyt, Essentials of carbohydrate chemistry, Springer-Verlag: New York, p. 34-35 (1998).
Rohyt, Essentials of carbohydrate chemistry, Springer-Verlag: New York, p. 350 (1998).
Rosenberg, et al., "Immunosurveillance of Alglucerase Enzyme Therapy for Gaucher Patients: Induction of Humoral Tolerance in Seroconverted Patients after Repeat Administration," Blood, 93(6):2081-2088 (1999).
Roth et al., "Mutants of Human Insulin-like Growth Factor II: Expression and Characterization of Analogs with a Substitution of TYR27 and/or a Deletion of Residues 62-67," Biochem. Biophys. Res. Commun., 181(2):907-914 (1991).
Russell et al., "Recombinant proteins for genetic disease," Clinical Genetics, 55:389-394 (1999).
Sakano et al., "The Design, Expression, and Characterization of Human Insulin-like Growth Factor II (IGF-II) Mutants Specific for Either the IGF-II/Cation-independent Mannose 6-Phosphate Receptor or IGF-I Receptor" The Journal of Biological Chemistry, 266(31):20626-20635 (1991).
Samoylova et al., "Elucidation of Muscle-Binding Peptides by Phage Display Screening," Muscle and Nerve, 22:460 (1999).
Sandoval et al., "Enhanced proliferative effects of a baculovirus-produced fusion protein of insulin-like growth factor and $_1$proteinase inhibitor and improved anti-elastase activity of the inhibitor with glutamate at position 351," Protein Engineering, 15(5):413-418 (2002).
Sandoval et al., "The fusion of IGF I with stromal cell-derived factor I or 1 proteinase inhibitor alters their mitogenic or chemotactic activities while keeping their ability to inhibit HIV-1-gp120 binding," Biochemical Pharmacology, 65:2055-2063 (2003).
Sands et al., "Biodistribution, Kinetics, and Efficacy of Highly Phosphorylated and Non-phosphorylated β-Glucuronidase in the Murine Model of Mucopolysaccharidosis VII," J. Biol. Chem., 276(46):43160-43165 (2001).
Sands et al., "Enzyme Replacement Therapy for Murine Mucopolysaccharidosis Type VII," J. Clin. Invest., 93(6):2324-2331 (1994).

Sands et al., "Murine Mucopolysaccharidosis Type VII: Long Term Therapeutic Effects of Enzyme Replacement and Enzyme Replacement Followed by Bone Marrow Transplantation," J. Clin. Invest., 99:1596-1605 (1997).
Shin et al., "Functional Properties of Antibody Insulin-like Growth Factor Fusion Proteins" J. Biol. Chem., 269(7):4979-4985 (1994).
Shipley et al., "The Role of Glycosylation and Phosphorylation in the Expression of Active Human β-Glucuronidase," J. Biol. Chem. 268(16):12193-12198 (1993).
Silverman, The Organic Chemistry of Drug Design and Drug Action, pp. 352-401, Academic Press, San. Diego, Calif. (1992).
Sly et al., "Active Site Mutant Transgene Confers Tolerance to Human β-Glucuronidase without Affecting the Phenotype of MPS VII Mice," PNAS, 98(5):2205-2210 (2001).
Smith and Waterman, "Identification of Common Molecular Subsequences," Journal of Molecular Biology, 147:195-197 (1981).
Smith et al., "Structure and Activity Dependence of Recombinant Human Insulin-like Growth Factor II on Disulfide Bond Pairing," The Journal of Biological Chemistry, 264(16):9314-9321 (1989).
Sohar et al., "Mouse Mutants Lacking the Cation-Independent Mannose 6-Phosphate/Insulin-Like Growth Factor II Receptor are Impaired in Lysosomal Enzyme Transport: Comparison of Cation-Independent and Cation-Dependent Mannose 6-Phosphate Receptor-Deficient Mice," Biochem. J., 330:903-908 (1998).
Sojar et al., "Characterization of Rat Ovarian Lutropin Receptor," J. Biol. Chem., 264(5):2552-2559 (1989).
Sojar et al., "Chemical Deglycosylation of Glycoproteins," Methods in Enzymology 138:341-350 (1987).
Soper et al., "Enzyme Replacement Therapy Improves Reproductive Performance in Mucopolysaccharidosis Type VII Mice, but Does Not Prevent Postnatal Losses," Pediatr. Res.45(2):180-186 (1999).
Souriau et al., "Direct Selection of EGF Mutants Displayed on Filamentous Phage Using Cells Overexpressing EGF Receptor," Biol. Chem., 380(4): pp. 451-458 (1999).
Sperr et al., "Rituximab for the treatment of acquired antibodies to factor VIII," Haematologica, 92(1):66-71 (Jan. 2007).
Spiro et al., "Characterization of Carbohydrate Units of Glycoproteins," Methods Enzymol. 8: 44-49 (1966).
Spodsberg, "Molecular Basis of Aberrant Apical Protein Transport in an Instestinal Enzyme Disorder," J. Biol. Chem., 276:23506 (2001).
Stahl et al., "Evidence for Specific Recognition Sites Mediating Clearance of Lysosomal Enzymes in vivo," PNAS 73(11):4045-4049 (1976).
Standley et al., "The role of glycosylation in ionotropic glutamate receptor ligand binding, function, and trafficking," Cellular and Molecular Life Sciences, 57:1508-1516 (1998).
Stanley et al., "Chinese Hamster Ovary Cells Selected for Resistance to the Cytotoxicity of Phytohemagglutinin are Deficient in a UDP-N-Acetylglucosamine-Glycoprotein N-Acetylglucosaminyltransferase Activity," Proc. Natl. Acad. Sci. USA 72(9):3323-3327 (1975).
Stanley et al., "Selection and Characterization of Eight Phenotypically Distinct Lines of Lectin-Resistant Chinese Hamster Ovary Cell" Cell, 6(2):121-128 (1975).
Summary of the Boston IPA Board Meeting Apr. 16-17, 2002, Association for Glycogen Storage Disease (UK) Bulletin, Issue 9, May 2002, p. 14.
Supplementary European Search Report for EP 02 72 5886 (2004).
Terasawa et al., "Solution Structure of Human Insulin-like Growth Factor II; Recognition Sites for Receptors and Binding Proteins," The EMBO Journal 13(23):5590-5597 (1994).
The Cytokine Facts Book (Second Ed. Academic Press, 2001). pp. 301-305; the page cited is included in form 892 and as 'appendix A'.
Thim, "A new family of growth factor-like peptides 'Trefoil disulphide loop structures as a common feature in breast cancer associated peptide (pS2), pancreatic spasmolytic polypeptide (PSP), and frog skin peptides (spasmolysins)," FEBS Lett., 250:85 (1989).
Thorpe et al., "Modification of the Carbohydrate in Ricin with Metaperiodate—Cyanoborohydride Mixtures," Eur. J. Biochem. 147:197-206 (1985).
Thotakura et al., "Enzymatic Deglycosylation of Glycoproteins," Methods in Enzymology, 138:350-359 (1987).

Thurgerg et al., "Characterization of pre- and post-treatment pathology after enzyme replacement therapy for pompe disease," Lab. Invest., 86:1208-1220 (2006).

Timmermans et al., "Angiotensin II Receptors and Angiotensin II Receptor Antagonists," Pharmacological Reviews 45(2):205-251 (1993).

Tong et al., "The Cation-independent Mannose 6-Phosphate Receptor Binds Insulin-like Growth Factor II," The Journal of Biological Chemistry, 263(6):2585-2588 (1988).

Torres et al., "Solution Structure of Human Insulin-like Growth Factor II. Relationship to Receptor and Binding Protein Interactions," J. Mol. Biol. 248(2):385-401 (1995).

Tschinke et al., "The Newlead Program: A New Method for the Design of Candidate Structures from Pharmacophoric Hypotheses," J. Med. Chem., 36:3863-3870 (1993).

Tsuji et al., "Intracellular Transport of Acid α-Glucosidase in Human Fibroblasts: Evidence for Involvement of Phosphomannosyl Receptor-Independent System," J. Biochem., 104(2):276-278 (1988).

Tsuji et al., "Lysosomal Enzyme Replacement Using $\alpha_2$-Macroglobulin as a Transport Vehicle," J. Biochem., 115:937-944 (1994).

Tsuji et al., "The Precursor of Acid α-Glucosidase is Synthesized as a Membrane-Bound Enzyme," Biochem. Int., 15(5):945-952 (1987).

Ulmasov et al., "Purification and Kinetic Analysis of Recombinant CA XII, a Membrane Carbonic Anhydrase Overexpressed in Certain Cancers," PNAS, 97(26):14212-14217 (2000).

Urayama et al., "Developmentally regulated mannose 6-phosephate receptor-mediated transport of a lysosomal enzyme across the blood-brain barrier," PNAS (USA), 101:12658-12663 (2004).

Vaccaro, Karen, email dated Feb. 20, 2002.

Valenzano et al., "Biophysical and Biological Properties of Naturally Occurring High Molecular Weight Insulin-like Growth Factor II Variants," J. Biol. Chem., 272(8):4804-4813 (1997).

Valenzano et al., "Soluble Insulin-like Growth Factor II/Mannose 6-Phosphate Receptor Carries Multiple High Molecular Weight Forms of Insulin-like GrowthFactor II in Fetal Bovine Serum," J. Biol. Chem.,270(27):16441-16448 (1995).

Van Den Hout et al., "Enzyme Therapy for Pompe Disease with Recombinant Human α-Glucosidase from Rabbit Milk," J: Inherit. Metab. Dis., 24(2):266-274 (2001).

Van Den Hout et al., "Recombinant Human α-Glucosidase from Rabbit Milk in Pompe Patients," Lancet 356(9227):397-398 (2000).

Van Der Ploeg et al., "Intravenous Administration of Phosphorylated Acid a-Glucosidase Leads to Uptake of Enzyme in Heart and Skeletal Muscle of Mice," J. Clin. Invest., 87:513-518 (1991).

Van Doorn et al., "Antibodies Directed against the E Region of Pro-Insulin-like Growth Factor-11 Used to Evaluate Non-Islet Cell Tumor-induced Hypoglycemia,"Clinical Chemistry, 48(10):1739-1750 (2002).

Van Hove et al., "High-Level Production of Recombinant Human Lysosomal Acid α-Glucosidase in Chinese Hamster Ovary Cells which Targets to Heart Muscle and Corrects Glycogen Accumulation in Fibroblasts from Patients with Pompe Disease," Pro. Natl. Acad. Sci. USA, 93(1):65-70 (1996).

Vogler et al., "A Murine Model of Mucopolysaccharidosis VII," Am. J. Pathol., 136(1):207-217 (1990).

Vogler et al., "Enzyme Replacement with Recombinant B-glucuronidase in the Newborn Mucopolysaccharidosis Type VII Mouse," Pediatric Research, 34(6):837-840 (1993).

Vogler et al., "Overcoming the blood-brain barier with high-dose enzyme replacement therapy in murine mucopolysaccharidosis VII," PNAS USA 10.1073/pnas.0506892102, 6 pages, (2005).

Vyas et al., "Ligand-Receptor-Mediated Drug Delivery: An Emerging Paradigm in Cellular Drug Targeting," Critical ReviewsTM in Therapeutic Drug Carrier Systems 18(1):1-76 (2001).

Wadensten et al., "Purification and Characterization of Recombinant Human Insulin-like Growth Factor II (IGF-II) Expressed as a Secreted Fusion Protein in *Escherichia coli*," Biotechnology and Applied Biochemistry, 13(3):412-421 (1991).

Waheed et al., "Human Lysosomal Acid Phosphatase is Transported as a Transmembrane Protein to Lysosomes in Transfected Baby Hamster Kidney Cells," EMBO J., 7(8):2351-2358 (1988).

Waheed et al., "Regulation of Transferrin-Mediated Iron Uptake by HFE, the Protein Defective in Hereditary Hemochromatosis," PNAS 99(5):3117-3122 (2002).

Wang et al., "A study of protein-protein interactions in living cells using luminescence resonance energy transfer (LRET) from Renilla luciferase to Aequorea GFP," Mol. Gen. Genet., 264:578-587 (2001).

Wang et al., "Regulation of Embryonic Growth and Lysosomal Targeting by the Imprinted *Igf2/Mpr* Gene," Nature, 372(6505):464-467 (1994).

Wang et al., "The Insulin A and B Chains Contain Sufficient Structural Information to Form the Native Molecule," Trends in Biochemical Sciences 16:279-281 (1991).

Waszkowycz et al., "Pro_Ligand: An Approach to de Novo Molecular Design. 2. Design of Novel Molecules from Molecular Field Analysis (MFA) Models and Pharmacophores," J. Med. Chem., 37:3994-4002 (1994).

Wilczak et al., "Insulin-like growth factor system in serum and cerebrospinal fluid in patients with multiple sclerosis," Neuroscience letters, 257:168-170 (1998).

Williams et al.,"Enzymes Replacement in Pompe Disease With an¯Glucosidase-Low Density Lipoprotein Complex"; XVI(1):415-423 (1980).

Willingham et al., "The Receptosome: an Intermediate Organelle of Receptor-Mediated Endocytosis in Cultured Fibroblasts," Cell, 21(1):67-77 (1980).

Wisselaar et al., "Structural and Functional Changes of Lysosomal Acid α-Glucosidase during Intracellular Transport and Maturation," J. Biol. Chem., 268(3):2223-2231 (1993).

Wolfe of al., "Murine Mucopolysaccharidosis Type VII: A Model System for Somatic Gene Therapy of the Central Nervous System," in Protocols for Gene Transfer in Neuroscience: Towards Gene Therapy of Neurological Disorders, Lowenstein, et al., eds., John Wiley & Sons Ltd., Chap. 20, pp. 263-274 (1996).

Written Opinion for PCT/US2005/004286 (2005).

Written Opinion for PCT/US2007/023881 (2009).

Yamashiro et al., "Acidification of Endocytic Compartments and the Intracellular Pathways of Ligands and Receptors," Journal of Cellular Biochemistry, 26:231-246 (1984).

Yang et al.,"Probing the Folding Pathways of Long R3 Insulin-like Growth Factor-1 (LR3IGF-1) and IGF-1 via Capture and Identification of Disulfide Intermediates by Cyanylation Methodology and Mass Spectrometry," The Journal of Biological Chemistry 274(53):37598-37604 (1999).

York et al., "The Rate of Internalization of the Mannose 6-Phosphate/ Insulin-like Growth Factor II Receptor Is Enhanced by Multivalent Ligand Binding," The Journal of Biological Chemistry, 274(2):1164-1171 (1999).

Yu et al., "Insuline-Like Growth Factors (IG-I, Free IGF-I, and IGF-II) and Insulin-Like Growth Factor Binding Proteins (IGFBP2, IGFBP-3, IGFBP-6, and ALS) in Blood Circulation," J. Clin. Lab. Anal., 13(4):166-72 (1999).

Zarn et al., "A Mutant of Human Insulin-like Growth Factor II (IGF II) with the Processing Sites of Proinsulin," Eur. J. Biochem. 210:665-669 (1992).

Zhu et al., "Carbohydrate-remodeled acid a-glucosidase with higher affinity for the cation-independent mannose 6-phosphate receptor demonstrates improved delivery to muscles of Pompe mice," Biochemical Journal, Biochem J., 389:619-628 (2005).

Zhu et al., "Conjugation of Mannose 6-Phosphate-containing Oligosaccharides to Acid-Glucosidase Improves the Clearance of Glycogen in Pompe Mice,"The Journal of Biological Chemistry, 279(48):50336-50341 (2004).

Zubieta et al., "Response: Measuring our natural painkiller," Trends in Neurosciences, 25(21:69-71 (2002).

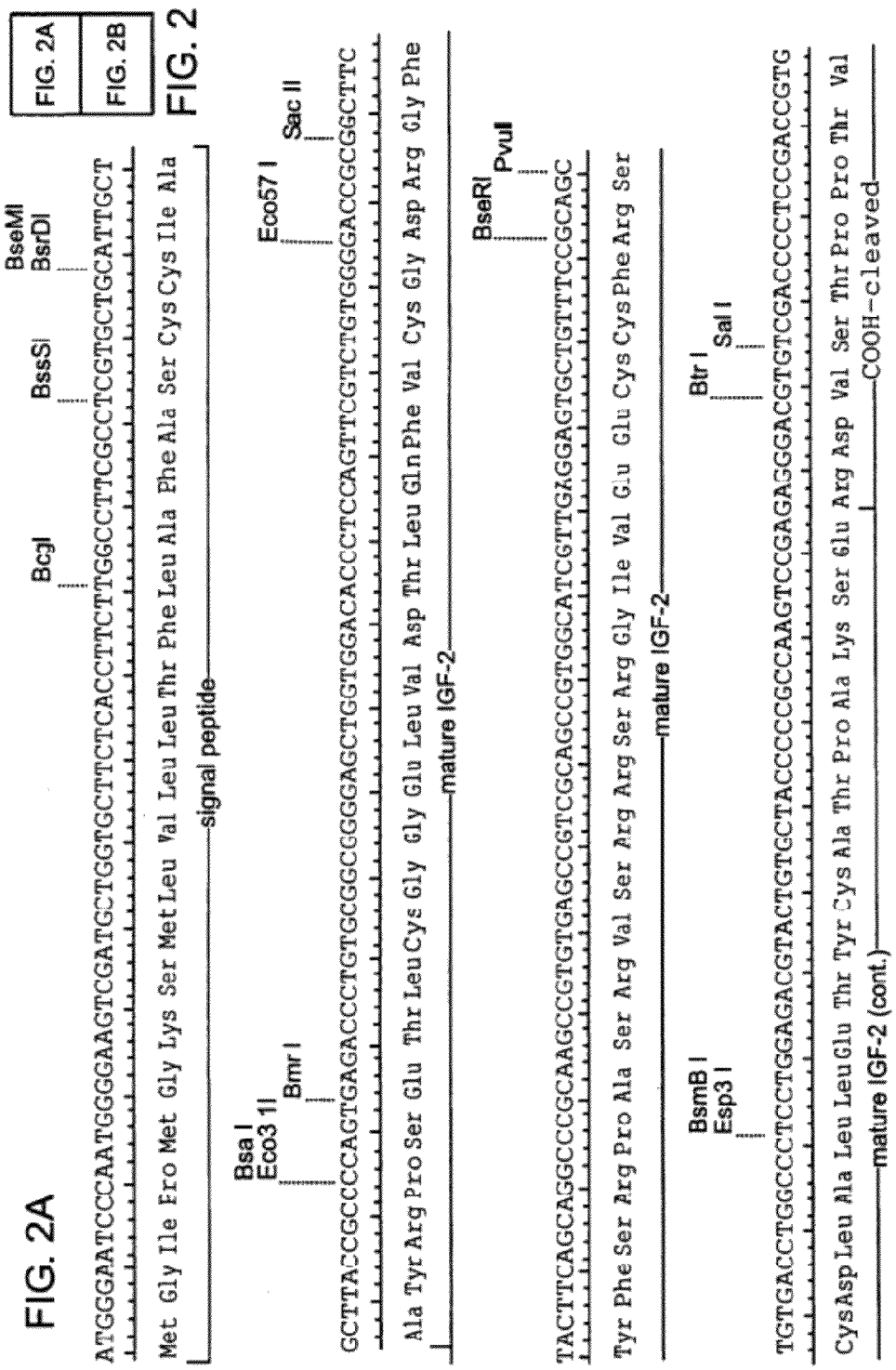

| FIG. 4A |
|---|
| FIG. 4B |
| FIG. 4C |
| FIG. 4D |
| FIG. 4E |

ATGGCCTCTAGGCTCGTCCGTGTGCTGGCGGCGCCATGCTGGTTGCAGGCGGCCGTGTCGGTCGCGCTGCAGGGC
   Met Ala Ser Arg Leu Val Arg Val Leu Ala Ala Met Leu Val Ala Ala Ala Val Ser Val Asp Ala Leu Gln Gly
   |————————————————————————— SAP signal peptide —————————————————————————|

GGGATGCTGTACCCCCAGGAGAGCCCGTCGCGGGAGTGCAAGGAGCTGGACGGCCTCTGGAGCTTCCGCGCC   150
Gly Met Leu Tyr Pro Gln Glu Ser Pro Ser Arg Glu Cys Lys Glu Leu Asp Gly Leu Trp Ser Phe Arg Ala
|——————————————————————————— mature β-GUS ———————————————————————————

GACTTCTCTGACAACCGACGCCGGGGCTTCGAGGAGCAGTGGTACCGGTGTACCGGTGTCAGGCCCCACCGTG
Asp Phe Ser Asp Asn Arg Arg Gly Phe Glu Glu Gln Trp Tyr Arg Arg Pro Leu Trp Glu Ser Gly Pro Thr Val
——————————————————————————— mature β-GUS ———————————————————————————

GACATGCCAGTTCCCTCCAGTTCAATGACATCAGCCAGGACTGGCGTCTCGGCATTTTGTCGGCTGGGTG   300
Asp Met Pro Val Pro Ser Ser Phe Asn Asp Ser Gln Asp Trp Arg Leu Arg His Phe Val Gly Trp Val
——————————————————————————— mature β-GUS ———————————————————————————

```
TGGTACGAACGGGAGGTGATCCTGCCGGAGCGATGACCCAGGACCTGCCGCACAAGAGTGGTGCTGAGGATTGGCAGT
                                    ———————mature β-GUS———————
Trp Tyr Glu Arg Glu Val Ile Leu Pro Glu Arg Trp Thr Gln Asp Leu Arg Arg Thr Arg Val Val Leu Arg Ile Gly Ser GCCCATTCCTATGCCATCGTGTGGGTGAATGGGGTCGACACGCTAGAGCATGAGGGGGCTACCTCCCTTC    450
                                    ———————mature β-GUS———————
Ala His Ser Tyr Ala Ile Val Trp Val Asn Gly Val Asp Thr Leu Glu His Glu Gly Gly Tyr Leu Pro Phe GAGGCCGATATCAGCAACCTGGTCCAGGTGGGCCCCCTCCCGGCTCCGAATCACTATGCCATCAACAACACA
                                    ———————mature β-GUS———————
Glu Ala Asp Ile Ser Asn Leu Val Gln Val Gly Pro Leu Pro Ser Arg Leu Arg Ile Thr Ile Ala Ile Asn Asn Thr CTCACCCCCCACCACCTGCCACCAGGACCATCCAATACCTGACTGACACCTCCAAGTATCCCAAGGGTTAC    600
                                    ———————mature β-GUS———————
Leu Thr Pro Thr Thr Leu Pro Pro Gly Thr Ile Gln Tyr Leu Thr Asp Thr Ser Lys Tyr Pro Lys Gly Tyr TTTGTCCAGAACACATATTTGACTTTTCAACTACGCTGGACTGCAGGGGTCTGTACTTCTGTACACGACACCCACC
                                    ———————mature β-GUS———————
Phe Val Gln Asn Thr Tyr Phe Asp Phe Phe Asn Tyr Ala Gly Leu Gln Arg Ser Val Leu Leu Tyr Thr Thr Pro Thr ACCTACATCGATGACATCACCGTCACCACCAGCGTGGAGCAAGACAGTGGCTGGTGAATTACCAGATCTCT    750
                                    ———————mature β-GUS———————
Thr Tyr Ile Asp Asp Ile Thr Val Thr Thr Ser Val Glu Gln Asp Ser Gly Leu Val Asn Tyr Gln Ile Ser
```

FIG. 4B

```
GTCAAGGCAGTAACCTGTTCAAGTTGGAAGTGCGTCTTTGGATGCAGAAACAAAGTCGTGGGAATGGGACTGGG
                     ─────────────── mature β-GUS ───────────────
Val Lys Gly Ser Asn Leu Phe Lys Leu Glu Val Arg Leu Asp Glu Asn Lys Val Val Ala Asn Gly Thr   Gly ACCCAGGGCCAACTTAAGGTGCCAGGTGTCAGCCTCTGTGGCCGTACCTGATGCACGAACGCCCTGCCTAT     900
                   ─────────────── mature β-GUS ───────────────
Thr Gln Gly Gln Leu Lys Val Pro Gy Val Ser Leu Trp Trp Pro Tyr Leu Met His Glu Arg Pro Ala Tyr CTGTATTCATTGGAGGTGCAGCTGACTGCACAGATGCAGCTGTGTCTGACTTCTACACTCCCTGTGGGG
 ────────────────── mature β-GUS ──────────────────
Leu Tyr Ser Leu Glu Val Gln Leu Thr Ala Gln Thr Ser Leu Gly Pro Val Ser Asp Phe Tyr Thr Leu Pro Val Gly ATCCGCACTGTGGCTGTCACCAAGAGCCAGTTCCTCATCAATGGGAAACCTTTCTATTTCCACGGTGTCAAC  1050
                    ─────────────── mature β-GUS ───────────────
Ile Arg Thr Val Ala Val Thr Lys Ser Gln Phe Leu Ile Asn Gly Lys Pro Phe Tyr Phe His Gly Val Asn AAGCATGAGGATGCCGGACATCCGAGGGAAGGGCTTGACTGGCCGCTGCTGGTGAAGGACTTCAACCTGCTTGCTGG
                ─────────────── mature β-GUS ───────────────
Lys His Glu Asp Ala Asp Ile Arg Gly Lys Gly Phe Asp Trp Pro Leu Leu Val Lys Asp Phe Asn Leu Leu Arg Trp CTTGGTGCCAAGCTTCCGTACCAGCCACTACCCCTATGCAGAGAAGTGATGCAGATGTGTGACCGCTAT      1200
              ─────────────── mature β-GUS ───────────────
Leu Gly Ala Asn Ala Phe Arg Thr Ser His Tyr Pro Tyr Ala Glu Gu  Val Met Gln Met Cys Asp Arg Tyr
```

FIG. 4C

```
GGGATTGTGGTCATCGATGAGTGTCCCGGCGTGGGTCTGGCGCTGCCCCAGTTCTTCAACAACGTTTCTCTGCATCAC
        Gly Ile Val Val Ile Asp Glu Cys Pro Gly Val Gly Leu Ala Leu Pro Gln Phe Phe Asn Asn Val Ser Leu His His
                                              mature β-GUS CACATGCAGGTGATGGAAGAAGTGGTGCGTAGGACAAGAACACCCCGGTCGTGATGTGGTCTGTGGCC 1350
 His Met Gln Val Met Glu Glu Val Val Arg Arg Asp Lys Asn His Pro Ala Val Val Met Trp Ser Val Ala
                                          mature β-GUS AACGAGCCTGCGTCCCACCTAGAATCTGCTACTACTTGAAGATGTGATCGCTCACACCAAATCCTTGGACCCC
 Asn Glu Pro Ala Ser His Leu Glu Ser Ala Gly Tyr Tyr Leu Lys Met Val Ile Ala His Thr Lys Ser Leu Asp Pro
                                         mature β-GUS TCCCGGCCTGTGACCTTTGTGAGCAACTCTAACTATGCAGCAGACAAGGGGCTCCGTATGTGGATGTGATC 1500
 Ser Arg Pro Val Thr Phe Val Ser Asn Ser Asn Tyr Ala Ala Asp Lys Gly Ala Pro Tyr Val Asp Val Ile
                                         mature β-GUS TGTTTGAACAGTACTACTACTCTTGGTATCACGACTGGCACCTGGAGTTGATTCAGCTGCAGTTGGCCACCCAGTTT
 Cys Leu Asn Ser Tyr Tyr Tyr Ser Trp Tyr His Asp Trp His Leu Glu Leu Ile Gln Leu Gln Leu Ala Thr Gln Phe
                                         mature β-GUS GAGAACTGGTATAAGAAGTATCAGAAGCCCATTATTCAGAGCGAGTATGGAGCAGAAACGATTGCAGGGTTT 1650
 Glu Asn Trp Tyr Lys Lys Tyr Gln Lys Pro Ile Ile Gln Ser Glu Tyr Gly Ala Glu Thr Ile Ala Gly Phe
```

FIG. 4D

```
CACCAGGATCCACCCTCTGATGTTCACTGAAGAGTACCAGAAAGTCTCTGAGAGCAGTACCATCTGGGTCTGGATCAA
              |----------------------- mature β-GUS -----------------------
His Gln Asp Pro Pro Leu Met Phe Thr Glu Glu Tyr Gln Lys Ser Leu Leu Glu Gln Tyr His Leu Gly Leu Asp Gln AACGCAGAAATATGTGGTTGGAGAGCTCATTTGGAATTTCATGACTGAACAGTCACCGACG                    1800
  ------------------------ mature β-GUS ------------------------
Lys Arg Arg Lys Tyr Val Val Gly Glu Leu Ile Trp Asn Phe Ala Asp Phe Met Thr Glu Gln Ser Pro Thr AGAGTGCTGGGAATAAAAGGGATCTTCACTCGGCAGAGACAACCAAAAGTGCAGTCCTTTTGCGAGAGAGA
  ------------------------ mature β-GUS ------------------------
Arg Val Leu Gly Asn Lys Lys Gly Ile Phe Thr Arg Gln Arg Gln Pro Lys Ser Ala Ala Phe Leu Leu Arg Glu Arg TACTGAAGATTGCCAATGAACCAGTATCCCACTCAGTAGCCAACTCACAATGTTTGAAAACAGCCCG             1950
  ------------------------ mature β-GUS ------------------------
Tyr Trp Lys Ile Ala Asn Glu Thr Arg Tyr Pro His Ser Val Ala Lys Ser Gln Cys Leu Glu Asn Ser Pro TTTACTGGCGCGCCGCCGGGTACCGCCCGAGAGCGCTGTGCGGCGAGCTGGTGGACACGCTGCAGTTCGTGTGC
  ---bridge---|------------------------ IGF-II ------------------------
Phe Thr Gly Ala Pro Ala Tyr Arg Pro Ser Glu Thr Leu Cys Gly Gly Glu Leu Val Asp Thr Leu Gln Phe Val Cys GGCGACCGCGGCTTCTACTTCAGCCGCCCCGCCAGCCGCGTGAGCCGCCGCAGCCGCGGCATCGTGGAGGAG         2100
  ------------------------ IGF-II ------------------------
Gly Asp Arg Gly Phe Tyr Phe Ser Arg Pro Ala Ser Arg Val Ser Arg Arg Ser Arg Gly Ile Val Glu Glu TGCTGCTTCCGCAGCTGCGACCTGGCGCTGCTGGAGACGTACTGCGCGACGCCGGCGAAGTCGGAGTAA         2169
  ------------------------ IGF-II ------------------------
Cys Cys Phe Arg Ser Cys Asp Leu Ala Leu Leu Glu Thr Tyr Cys Ala Thr Pro Ala Lys Ser Glu
```

FIG. 4E

FIG. 16: Liver

FIG. 17: Kidney

FIG. 18: Bone

FIG. 19: Spleen

B-glucuronidase Levels after infusion with endoglycosidase F1-treated, CHO-produced ΔΔ, endoglycosidase F1-treated, Lec-1-produced ΔΔ, or untreated, HEK-produced ΔΔ

Tissue B-glucuronidase units/mg protein

| Expt. # | Treated CHO ΔΔ | | | Treated Lec-1 ΔΔ | | | Untreated HEK ΔΔ | | |
|---|---|---|---|---|---|---|---|---|---|
| Tissue | 1 | 2 | 3 | 4 | 5 | 6 | 7 | 8 | 9 |
| Brain | 0.49 | .024 | 0.15 | 0.19 | 0.16 | 0.15 | 0.17 | 0.19 | 0.23 |
| Liver | 144 | 147 | 163 | 125 | 105 | 130 | 188 | 155 | 184 |
| Heart | 2.24 | 3.00 | 1.92 | 2.69 | 2.79 | 3.49 | 4.64 | 2.35 | 3.12 |
| Kidney | 2.41 | 2.76 | - | 3.71 | 2.63 | 3.72 | 5.41 | 4.56 | 5.58 |
| Muscle | 1.18 | .071 | 0.79 | 1.41 | 1.57 | 1.87 | 5.01 | 1.49 | 2.00 |
| Serum (u/ml) @ 1 hr | 740 | 740 | 700 | 2920 | 1930 | 1880 | 2590 | 1250 | 1060 |
| Serum (u/ml) @ 24 hr | 1.77 | 151 | 2.13 | 16.47 | 10.43 | 6.95 | 4.05 | 1.94 | 2.08 |

| Enzyme | Half life (days) |
|---|---|
| HBG5 | 17.2 |
| HBG5 +F1 | 18.5 |
| CHO | 25.1 |
| CHO +F1 | 22 |
| Lec1 | 18.7 |
| Lec1 +F1 | 19.6 |

GAL-GILTΔ1-7:

ctcgagaggtcgacggtatcgataagcttgatatcgaattcgtgacaatgatgcagctgaggaacccagaac
tacatctgggctgcgcgcttgcgcttcgcttcctggccctcgtttcctgggacatccctggggctagagcac
tggacaatggattggcaaggacgcctaccatgggctggctgcactgggagcgcttcatgtgcaaccttgact
gccaggaagagccagattcctgcatcagtgagaagctcttcatggagatggcagagctcatgtctcagaag
gctggaaggatgcaggttatgagtacctctgcattgatgactgttggatggctccccaaagagattcagaag
gcagacttcaggcagaccctcagcgctttcctcatgggattcgccagctagctaattatgttcacagcaaag
gactgaagctagggatttatgcagatgttggaaataaaacctgcgcaggcttccctgggagttttggatact
acgacattgatgcccagacctttgctgactggggagtagatctgctaaaatttgatggttgttactgtgaca
gtttggaaaatttggcagatggttataagcacatgtccttggccctgaataggactggcagaagcattgtgt
actcctgtgagtggcctctcttatatgtggccctttcaaaagcccaattatacagaaatccgacagtactgca
atcactggcgaaattttgctgacattgatgattcctggaaaagtataaagagtatcttggactggacatctt
ttaaccaggagagaattgttgatgttgctggaccaggggggttggaatgacccagatatgttagtgattggca
actttggcctcagctggaatcagcaagtaactcagatggccctctgggctatcatggctgctcctttattca
tgtctaatgacctccgacacatcagccctcaagccaaagctctccttcaggataaggacgtaattgccatca
atcaggacccccttgggcaagcaagggtaccagcttagacaggagagacaactttgaagtgtgggaacgacctc
tctcaggcttagcctgggctgtagctatgataaaccggcaggagattggtggacctcgtcttataccatcg
cagttgcttccctgggtaaaggagtggcctgtaatcctgcctgcttcatcacacagctcctccctgtgaaaa
ggaagctagggttctatgaatggacttcaaggttaagaagtcacataaatcccacaggcactgttttgcttc
agctagaaaatacaatgcagatgtcattaaaagacttacttggcgcgccgctgtgcggcggcgagctggtgg
acacgctgcagttcgtgtgcggcgaccgcggcttctacttcagccgcccggccagccgcgtgagccgccgca
gccgcggcatcgtgaggagtgctgcttccgcagctgcgacctggcgctgctggagacgtactgcgcgacgc
cggcgaagtcggagtaagaattcctgcagcccggg

FIG. 27

GAL:

ctcgagaggtcgacggtatcgataagcttgatatcgaattcgtgacaatgcagctgaggaacccagaactac
atctgggctgcgcgcttgcgcttcgcttcctggccctcgtttcctgggacatccctggggctagagcactgg
acaatggattggcaaggacgcctaccatgggctggctgcactgggagcgcttcatgtgcaaccttgactgcc
aggaagagccagattcctgcatcagtgagaagctcttcatggagatggcagagctcatggtctcagaaggct
ggaaggatgcaggttatgagtacctctgcattgatgactgttggatggctccccaaagagattcagaaggca
gacttcaggcagaccctcagcgctttcctcatgggattcgccagctagctaattatgttcacagcaaaggac
tgaagctagggatttatgcagatgttggaaataaaacctgcgcaggcttccctgggagttttggatactacg
acattgatgcccagacctttgctgactggggagtagatctgctaaaatttgatggttgttactgtgacagtt
tggaaaatttggcagatggttataagcacatgtccttggccctgaataggactggcagaagcattgtgtact
cctgtgagtggcctctttatatgtggccctttcaaaagcccaattatacagaaatccgacagtactgcaatc
actggcgaaattttgctgacattgatgattcctggaaaagtataaagagtatcttggactggacatcttta
accaggagagaattgttgatgttgctggaccaggggggttggaatgacccagatatgttagtgattggcaact
ttggcctcagctggaatcagcaagtaactcagatggccctctgggctatcatggctgctcctttattcatgt
ctaatgacctccgacacatcagccctcaagccaaagctctccttcaggataaggacgtaattgccatcaatc
aggacccttgggcaagcaagggtaccagcttagacagggagacaactttgaagtgtgggaacgacctctct
caggcttagcctgggctgtagctatgataaaccggcaggagattggtggacctcgctcttataccatcgcag
ttgcttccctgggtaaaggagtggcctgtaatcctgcctgcttcatcacacagctcctccctgtgaaaagga
agctagggttctatgaatggacttcaaggttaagaagtcacataaatcccacaggcactgttttgcttcagc
tagaaaatacaatgcagatgtcattaaaagacttactttaagaattcctgcagcccggg

FIG. 28 pISSWA:

```
tagttattaatagtaatcaattacggggtcattagttcatagcccatatatggagttccgcgttacataact
tacggtaaatggcccgcctggctgaccgcccaacgaccccgcccattgacgtcaataatgacgtatgttcc
catagtaacgccaatagggactttccattgacgtcaatgggtggagtatttacggtaaactgcccacttggc
agtacatcaagtgtatcatatgccaagtacgccccctattgacgtcaatgacggtaaatggcccgcctggca
ttatgcccagtacatgaccttatgggactttcctacttggcagtacatctacgtattagtcatcgctattac
catggtgatgcggttttggcagtacatcaatgggcgtggatagcggtttgactcacggggatttccaagtct
ccacccccattgacgtcaatgggagtttgttttggcaccaaaatcaacgggactttccaaaatgtcgtaacaa
ctccgccccattgacgcaaatgggcggtaggcgtgtacggtgggaggtctatataagcagagctcgtttagt
gaaccgtcagatcgcctggagacgccatccacgctgttttgacctccatagaagacaccgggaccgatccag
cctccgcggccgggaacggtgcattggaacgcggattccccgtgccaagagtgacgtaagtaccgcctatag
actctataggcacaccccttttggctcttatgcatgaattaatacgactcactatagggagacagactgttcc
tttcctgggtcttttctgcaggcaccgtcgtcgacttaacagatctcgagctcaagcttcgaattctgcagt
cgacggtaccgcgggcccgggatccaccgggtacaagtaaagcggccgcgactctagatcataatcagccat
accacatttgtagaggttttacttgcttttaaaaaacctcccacacctccccctgaacctgaaacataaaatg
aatgcaattgttgttgttaacttgtttattgcagcttataatggttacaaataaagcaatagcatcacaaat
ttcacaaataaagcatttttttcactgcattctagttgtggtttgtccaaactcatcaatgtatcTTAAatt
taaatggctttacactttatgcttccggctcgtataatgtgcactacgtgaaccatcaccctaatcaagttt
tttgggtcgaggtgccgtaaagcactaaatcggaaccctaaagggagccccgatttagagcttgacgggg
aaagccggcgaacgtggcgagaaaggaagggaagaaagcgaaaggagcgggcgctagggcgctggcaagtgt
agcggtcacgctgcgcgtaaccacaccccgccgcgcttaatgcgccgctacagggcgcgtcaggtggcac
ttttcggggaaatgtgcgcggaacccctatttgtttatttttctaaatacattcaaatatgtatccgctcat
gagacaataaccctgataaatgcttcaataatattgaaaaaggaagagtcctgaggcggaaagaaccagtct
caattagtcagcaaccatagtcccgcccctaactccgcccatcccgcccctaactccgcccagttccgccca
ttctccgcccatggctgactaatttttttattatgcagaggccgaggccgcctcggcctctgagctatt
ccagaagtagtgaggaggcttttttggaggcctaggcttttgcaaagatcgatcaagagacaggatgaggat
cgtttcgcatgattgaacaagatggattgcacgcaggttctccggccgcttgggtggagaggctattcggct
atgactgggcacaacagacaatcggctgctctgatgccgccgtgttccggctgtcagcgcaggggcgcccgg
ttcttttttgtcaagaccgacctgtccggtgccctgaatgaactgcaagacgaggcagcgcggctatcgtggc
tggccacgacgggcgttccttgcgcagctgtgctcgacgttgtcactgaagcgggaagggactggctgctat
tgggcgaagtgccggggcaggatctcctgtcatctcaccttgctcctgccgagaaagtatccatcatggctg
atgcaatgcggcggctgcatacgcttgatccggctacctgcccattcgaccaccaagcgaaacatcgcatcg
agcgagcacgtactcggatggaagccggtcttgtcgatcaggatgatctggacgaagagcatcaggggctcg
cgccagccgaactgttcgccaggctcaaggcgagcatgcccgacggcgatgatctcgtcgtgacccatggcg
atgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctg
accgcttcctcgtgctttacggtatcgccgctcccgattcgcagcgcatcgccttctatcgccttcttgacg
agttcttctgagcgggactctggggttcgaaatgaccgaccaagcgacgcccaacctgccatcacgagattt
cgattccaccgccgccttctatgaaaggttgggcttcggaatcgttttccgggacgccggctggatgatcct
ccagcgcggggatctcatgctggagttcttcgcccacccctaggggaggctaactgaaacacggaaggagac
aataccggaaggaacccgcgctatgacggcaataaaaagacagaataaaacgcacggtgttgggtcgtttgt
tcataaacgcggggttcggtcccagggctggcactctgtcgataccccaccgagaccccattggggccaata
cgcccgcgtttcttccttttccccaccccaccccccaagttcgggtgaaggcccagggctcgcagccaacgt
cggggcggcaggccctgccatagcctcaggttactcatatatactttagattgatttaaaacttcatttta
atttaaaaggatctaggtgaagatccttttgataatctcatgaccaaaatcccttaacgtgagttttcgtt
ccactgagcgtcagaccccgtagaaaagatcaaaggatcttcttgagatccttttttttctgcgcgtaatctg
ctgcttgcaaacaaaaaaaccaccgctaccagcggtggtttgtttgccggatcaagagctaccaactcttt
tccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccag
tggcgataagtcgtgtcttaccgggttggactcaagacgatagttaccggataaggcgcagcggtcgggctg
```

FIG. 29 (page 1 of 2)

```
aacgggggttcgtgcacacagcccagcttggagcgaacgacctacaccgaactgagatacctacagcgtga
gctatgagaaagcgccacgcttcccgaagggagaaaggcggacaggtatccggtaagcggcagggtcggaac
aggagagcgcacgagggagcttcaggggaaacgcctggtatctttatagtcctgtcgggtttcgccacct
ctgacttgagcgtcgattttgtgatgctcgtcaggggggcggagcctatggaaaaacgccagcaacgcggc
cttttacggttcctggccttttgctggccttttgctcacatgttctttcctgcgttatcccctgattctgt
ggataaccgtattaccgccatgcat
```

FIG. 29 (page 2 of 2)

SEQUENCE LISTING

```
<160> NUMBER OF SEQ ID NOS: 30

<210> SEQ ID NO 1
<211> LENGTH: 543
<212> TYPE: DNA
<213> ORGANISM: Homo sapiens
<220> FEATURE:
<221> NAME/KEY: CDS
<222> LOCATION: (1)..(540)

<400> SEQUENCE: 1 atg gga atc cca atg ggg aag tcg atg ctg gtg ctt ctc acc ttc ttg         48
Met Gly Ile Pro Met Gly Lys Ser Met Leu Val Leu Leu Thr Phe Leu
1               5                   10                  15 gcc ttc gcc tcg tgc tgc att gct gct tac cgc ccc agt gag acc ctg         96
Ala Phe Ala Ser Cys Cys Ile Ala Ala Tyr Arg Pro Ser Glu Thr Leu
            20                  25                  30 tgc ggc ggg gag ctg gtg gac acc ctc cag ttc gtc tgt ggg gac cgc        144
Cys Gly Gly Glu Leu Val Asp Thr Leu Gln Phe Val Cys Gly Asp Arg
        35                  40                  45 ggc ttc tac ttc agc agg ccc gca agc cgt gtg agc cgt cgc agc cgt        192
Gly Phe Tyr Phe Ser Arg Pro Ala Ser Arg Val Ser Arg Arg Ser Arg
    50                  55                  60 ggc atc gtt gag gag tgc tgt ttc cgc agc tgt gac ctg gcc ctc ctg        240
Gly Ile Val Glu Glu Cys Cys Phe Arg Ser Cys Asp Leu Ala Leu Leu
65                  70                  75                  80 gag acg tac tgt gct acc ccc gcc aag tcc gag agg gac gtg tcg acc        288
Glu Thr Tyr Cys Ala Thr Pro Ala Lys Ser Glu Arg Asp Val Ser Thr
                85                  90                  95 cct ccg acc gtg ctt ccg gac aac ttc ccc aga tac ccc gtg ggc aag        336
Pro Pro Thr Val Leu Pro Asp Asn Phe Pro Arg Tyr Pro Val Gly Lys
            100                 105                 110 ttc ttc caa tat gac acc tgg aag cag tcc acc cag cgc ctg cgc agg        384
Phe Phe Gln Tyr Asp Thr Trp Lys Gln Ser Thr Gln Arg Leu Arg Arg
        115                 120                 125 ggc ctg cct gcc ctc ctg cgt gcc cgc cgg ggt cac gtg ctc gcc aag        432
Gly Leu Pro Ala Leu Leu Arg Ala Arg Arg Gly His Val Leu Ala Lys
    130                 135                 140 gag ctc gag gcg ttc agg gag gcc aaa cgt cac cgt ccc ctg att gct        480
Glu Leu Glu Ala Phe Arg Glu Ala Lys Arg His Arg Pro Leu Ile Ala
145                 150                 155                 160 cta ccc acc caa gac ccc gcc cac ggg ggc gcc cca gag atg gcc             528
Leu Pro Thr Gln Asp Pro Ala His Gly Gly Ala Pro Glu Met Ala
                165                 170                 175 agc aat cgg aag tga                                                     543
Ser Asn Arg Lys
            180
```

```
<210> SEQ ID NO 2
<211> LENGTH: 180
<212> TYPE: PRT
<213> ORGANISM: Homo sapiens

<400> SEQUENCE: 2

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
                165                 170                 175

Ser Asn Arg Lys
            180

<210> SEQ ID NO 3
<211> LENGTH: 180
<212> TYPE: PRT
<213> ORGANISM: Homo sapiens

<400> SEQUENCE: 3

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
        35                  40                  45

Gly Phe Tyr Phe Ser Arg Pro Ala Ser Arg Val Ser Arg Arg Ser Arg
    50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His Arg Pro Leu Ile Ala
145                 150                 155                 160
```

```
Leu Pro Thr Gln Asp Pro Ala His Gly Gly Ala Pro Pro Glu Met Ala
            165                 170                 175

Ser Asn Arg Lys
            180

<210> SEQ ID NO 4
<211> LENGTH: 237
<212> TYPE: DNA
<213> ORGANISM: Artificial Sequence
<220> FEATURE:
<223> OTHER INFORMATION: Leishmania codon optimized IGF-II
<220> FEATURE:
<221> NAME/KEY: CDS
<222> LOCATION: (14)..(223)

<400> SEQUENCE: 4
ccgtctagag ctc ggc gcg ccg gcg tac cgc ccg agc gag acg ctg tgc         49
               Gly Ala Pro Ala Tyr Arg Pro Ser Glu Thr Leu Cys
                 1               5                  10 ggc ggc gag ctg gtg gac acg ctg cag ttc gtg tgc ggc gac cgc ggc        97
Gly Gly Glu Leu Val Asp Thr Leu Gln Phe Val Cys Gly Asp Arg Gly
             15                  20                  25 ttc tac ttc agc cgc ccg gcc agc cgc gtg agc cgc cgc agc cgc ggc       145
Phe Tyr Phe Ser Arg Pro Ala Ser Arg Val Ser Arg Arg Ser Arg Gly
     30                  35                  40 atc gtg gag gag tgc tgc ttc cgc agc tgc gac ctg gcg ctg ctg gag       193
Ile Val Glu Glu Cys Cys Phe Arg Ser Cys Asp Leu Ala Leu Leu Glu
 45                  50                  55                  60 acg tac tgc gcg acg ccg gcg aag tcg gag taagatctag agcg               237
Thr Tyr Cys Ala Thr Pro Ala Lys Ser Glu
                 65                  70

<210> SEQ ID NO 5
<211> LENGTH: 70
<212> TYPE: PRT
<213> ORGANISM: Artificial Sequence
<220> FEATURE:
<223> OTHER INFORMATION: Synthetic Construct

<400> SEQUENCE: 5

Gly Ala Pro Ala Tyr Arg Pro Ser Glu Thr Leu Cys Gly Gly Glu Leu
1               5                  10                  15

Val Asp Thr Leu Gln Phe Val Cys Gly Asp Arg Gly Phe Tyr Phe Ser
            20                  25                  30

Arg Pro Ala Ser Arg Val Ser Arg Arg Ser Arg Gly Ile Val Glu Glu
        35                  40                  45

Cys Cys Phe Arg Ser Cys Asp Leu Ala Leu Leu Glu Thr Tyr Cys Ala
    50                  55                  60

Thr Pro Ala Lys Ser Glu
65                  70

<210> SEQ ID NO 6
<211> LENGTH: 70
<212> TYPE: PRT
<213> ORGANISM: Artificial Sequence
<220> FEATURE:
<223> OTHER INFORMATION: Synthetic Construct

<400> SEQUENCE: 6

Gly Ala Pro Ala Tyr Arg Pro Ser Glu Thr Leu Cys Gly Gly Glu Leu
1               5                  10                  15

Val Asp Thr Leu Gln Phe Val Cys Gly Asp Arg Gly Phe Tyr Phe Ser
            20                  25                  30
```

-continued

```
Arg Pro Ala Ser Arg Val Ser Arg Arg Ser Arg Gly Ile Val Glu Glu
            35                  40                  45

Cys Cys Phe Arg Ser Cys Asp Leu Ala Leu Leu Glu Thr Tyr Cys Ala
        50                  55                  60

Thr Pro Ala Lys Ser Glu
65                  70

<210> SEQ ID NO 7
<211> LENGTH: 2169
<212> TYPE: DNA
<213> ORGANISM: Artificial Sequence
<220> FEATURE:
<223> OTHER INFORMATION: A recombinant DNA sequence incorporating a
      signal peptide sequence, the mature human beta-glucuronidase
      sequence, a bridge of three amino acids, and an IGF-II sequence
<220> FEATURE:
<221> NAME/KEY: CDS
<222> LOCATION: (1)..(2166)

<400> SEQUENCE: 7 atg gcc tct agg ctc gtc cgt gtg ctg gcg gcc gcc atg ctg gtt gca        48
Met Ala Ser Arg Leu Val Arg Val Leu Ala Ala Ala Met Leu Val Ala
1               5                   10                  15 gcg gcc gtg tcg gtc gac gcg ctg cag ggc ggg atg ctg tac ccc cag        96
Ala Ala Val Ser Val Asp Ala Leu Gln Gly Gly Met Leu Tyr Pro Gln
                20                  25                  30 gag agc ccg tcg cgg gag tgc aag gag ctg gac ggc ctc tgg agc ttc       144
Glu Ser Pro Ser Arg Glu Cys Lys Glu Leu Asp Gly Leu Trp Ser Phe
            35                  40                  45 cgc gcc gac ttc tct gac aac cga cgc cgg ggc ttc gag gag cag tgg       192
Arg Ala Asp Phe Ser Asp Asn Arg Arg Arg Gly Phe Glu Glu Gln Trp
        50                  55                  60 tac cgg cgg ccg ctg tgg gag tca ggc ccc acc gtg gac atg cca gtt       240
Tyr Arg Arg Pro Leu Trp Glu Ser Gly Pro Thr Val Asp Met Pro Val
65                  70                  75                  80 ccc tcc agc ttc aat gac atc agc cag gac tgg cgt ctg cgg cat ttt       288
Pro Ser Ser Phe Asn Asp Ile Ser Gln Asp Trp Arg Leu Arg His Phe
                85                  90                  95 gtc ggc tgg gtg tgg tac gaa cgg gag gtg atc ctg ccg gag cga tgg       336
Val Gly Trp Val Trp Tyr Glu Arg Glu Val Ile Leu Pro Glu Arg Trp
            100                 105                 110 acc cag gac ctg cgc aca aga gtg gtg ctg agg att ggc agt gcc cat       384
Thr Gln Asp Leu Arg Thr Arg Val Val Leu Arg Ile Gly Ser Ala His
        115                 120                 125 tcc tat gcc atc gtg tgg gtg aat ggg gtc gac acg cta gag cat gag       432
Ser Tyr Ala Ile Val Trp Val Asn Gly Val Asp Thr Leu Glu His Glu
    130                 135                 140 ggg ggc tac ctc ccc ttc gag gcc gac atc agc aac ctg gtc cag gtg       480
Gly Gly Tyr Leu Pro Phe Glu Ala Asp Ile Ser Asn Leu Val Gln Val
145                 150                 155                 160 ggg ccc ctg ccc tcc cgg ctc cga atc act atc gcc atc aac aac aca       528
Gly Pro Leu Pro Ser Arg Leu Arg Ile Thr Ile Ala Ile Asn Asn Thr
                165                 170                 175 ctc acc ccc acc acc ctg cca cca ggg acc atc caa tac ctg act gac       576
Leu Thr Pro Thr Thr Leu Pro Pro Gly Thr Ile Gln Tyr Leu Thr Asp
            180                 185                 190 acc tcc aag tat ccc aag ggt tac ttt gtc cag aac aca tat ttt gac       624
Thr Ser Lys Tyr Pro Lys Gly Tyr Phe Val Gln Asn Thr Tyr Phe Asp
        195                 200                 205 ttt ttc aac tac gct gga ctg cag cgg tct gta ctt ctg tac acg aca       672
Phe Phe Asn Tyr Ala Gly Leu Gln Arg Ser Val Leu Leu Tyr Thr Thr
    210                 215                 220
```

```
ccc acc acc tac atc gat gac atc acc gtc acc acc agc gtg gag caa         720
Pro Thr Thr Tyr Ile Asp Asp Ile Thr Val Thr Thr Ser Val Glu Gln
225             230                 235                 240 gac agt ggg ctg gtg aat tac cag atc tct gtc aag ggc agt aac ctg         768
Asp Ser Gly Leu Val Asn Tyr Gln Ile Ser Val Lys Gly Ser Asn Leu
                245                 250                 255 ttc aag ttg gaa gtg cgt ctt ttg gat gca gaa aac aaa gtc gtg gcg         816
Phe Lys Leu Glu Val Arg Leu Leu Asp Ala Glu Asn Lys Val Val Ala
            260                 265                 270 aat ggg act ggg acc cag ggc caa ctt aag gtg cca ggt gtc agc ctc         864
Asn Gly Thr Gly Thr Gln Gly Gln Leu Lys Val Pro Gly Val Ser Leu
        275                 280                 285 tgg tgg ccg tac ctg atg cac gaa cgc cct gcc tat ctg tat tca ttg         912
Trp Trp Pro Tyr Leu Met His Glu Arg Pro Ala Tyr Leu Tyr Ser Leu
    290                 295                 300 gag gtg cag ctg act gca cag acg tca ctg ggg cct gtg tct gac ttc         960
Glu Val Gln Leu Thr Ala Gln Thr Ser Leu Gly Pro Val Ser Asp Phe
305                 310                 315                 320 tac aca ctc cct gtg ggg atc cgc act gtg gct gtc acc aag agc cag        1008
Tyr Thr Leu Pro Val Gly Ile Arg Thr Val Ala Val Thr Lys Ser Gln
                325                 330                 335 ttc ctc atc aat ggg aaa cct ttc tat ttc cac ggt gtc aac aag cat        1056
Phe Leu Ile Asn Gly Lys Pro Phe Tyr Phe His Gly Val Asn Lys His
            340                 345                 350 gag gat gcg gac atc cga ggg aag ggc ttc gac tgg ccg ctg ctg gtg        1104
Glu Asp Ala Asp Ile Arg Gly Lys Gly Phe Asp Trp Pro Leu Leu Val
        355                 360                 365 aag gac ttc aac ctg ctt cgc tgg ctt ggt gcc aac gct ttc cgt acc        1152
Lys Asp Phe Asn Leu Leu Arg Trp Leu Gly Ala Asn Ala Phe Arg Thr
    370                 375                 380 agc cac tac ccc tat gca gag gaa gtg atg cag atg tgt gac cgc tat        1200
Ser His Tyr Pro Tyr Ala Glu Glu Val Met Gln Met Cys Asp Arg Tyr
385                 390                 395                 400 ggg att gtg gtc atc gat gag tgt ccc ggc gtg ggt ctg gcg ctg ccg        1248
Gly Ile Val Val Ile Asp Glu Cys Pro Gly Val Gly Leu Ala Leu Pro
                405                 410                 415 cag ttc ttc aac aac gtt tct ctg cat cac cac atg cag gtg atg gaa        1296
Gln Phe Phe Asn Asn Val Ser Leu His His His Met Gln Val Met Glu
            420                 425                 430 gaa gtg gtg cgt agg gac aag aac cac ccc gcg gtc gtg atg tgg tct        1344
Glu Val Val Arg Arg Asp Lys Asn His Pro Ala Val Val Met Trp Ser
        435                 440                 445 gtg gcc aac gag cct gcg tcc cac cta gaa tct gct ggc tac tac ttg        1392
Val Ala Asn Glu Pro Ala Ser His Leu Glu Ser Ala Gly Tyr Tyr Leu
    450                 455                 460 aag atg gtg atc gct cac acc aaa tcc ttg gac ccc tcc cgg cct gtg        1440
Lys Met Val Ile Ala His Thr Lys Ser Leu Asp Pro Ser Arg Pro Val
465                 470                 475                 480 acc ttt gtg agc aac tct aac tat gca gca gac aag ggg gct ccg tat        1488
Thr Phe Val Ser Asn Ser Asn Tyr Ala Ala Asp Lys Gly Ala Pro Tyr
                485                 490                 495 gtg gat gtg atc tgt ttg aac agc tac tac tct tgg tat cac gac tac        1536
Val Asp Val Ile Cys Leu Asn Ser Tyr Tyr Ser Trp Tyr His Asp Tyr
            500                 505                 510 ggg cac ctg gag ttg att cag ctg cag ctg gcc acc cag ttt gag aac        1584
Gly His Leu Glu Leu Ile Gln Leu Gln Leu Ala Thr Gln Phe Glu Asn
        515                 520                 525 tgg tat aag aag tat cag aag ccc att att cag agc gag tat gga gca        1632
Trp Tyr Lys Lys Tyr Gln Lys Pro Ile Ile Gln Ser Glu Tyr Gly Ala
    530                 535                 540
```

-continued

```
gaa acg att gca ggg ttt cac cag gat cca cct ctg atg ttc act gaa    1680
Glu Thr Ile Ala Gly Phe His Gln Asp Pro Pro Leu Met Phe Thr Glu
545                 550                 555                 560 gag tac cag aaa agt ctg cta gag cag tac cat ctg ggt ctg gat caa    1728
Glu Tyr Gln Lys Ser Leu Leu Glu Gln Tyr His Leu Gly Leu Asp Gln
            565                 570                 575 aaa cgc aga aaa tat gtg gtt gga gag ctc att tgg aat ttt gcc gat    1776
Lys Arg Arg Lys Tyr Val Val Gly Glu Leu Ile Trp Asn Phe Ala Asp
        580                 585                 590 ttc atg act gaa cag tca ccg acg aga gtg ctg ggg aat aaa aag ggg    1824
Phe Met Thr Glu Gln Ser Pro Thr Arg Val Leu Gly Asn Lys Lys Gly
    595                 600                 605 atc ttc act cgg cag aga caa cca aaa agt gca gcg ttc ctt ttg cga    1872
Ile Phe Thr Arg Gln Arg Gln Pro Lys Ser Ala Ala Phe Leu Leu Arg
610                 615                 620 gag aga tac tgg aag att gcc aat gaa acc agg tat ccc cac tca gta    1920
Glu Arg Tyr Trp Lys Ile Ala Asn Glu Thr Arg Tyr Pro His Ser Val
625                 630                 635                 640 gcc aag tca caa tgt ttg gaa aac agc ccg ttt act ggc gcg ccg gcg    1968
Ala Lys Ser Gln Cys Leu Glu Asn Ser Pro Phe Thr Gly Ala Pro Ala
            645                 650                 655 tac cgc ccg agc gag acg ctg tgc ggc ggc gag ctg gtg gac acg ctg    2016
Tyr Arg Pro Ser Glu Thr Leu Cys Gly Gly Glu Leu Val Asp Thr Leu
        660                 665                 670 cag ttc gtg tgc ggc gac cgc ggc ttc tac ttc agc cgc ccg gcc agc    2064
Gln Phe Val Cys Gly Asp Arg Gly Phe Tyr Phe Ser Arg Pro Ala Ser
    675                 680                 685 cgc gtg agc cgc cgc agc cgc ggc atc gtg gag gag tgc tgc ttc cgc    2112
Arg Val Ser Arg Arg Ser Arg Gly Ile Val Glu Glu Cys Cys Phe Arg
690                 695                 700 agc tgc gac ctg gcg ctg ctg gag acg tac tgc gcg acg ccg gcg aag    2160
Ser Cys Asp Leu Ala Leu Leu Glu Thr Tyr Cys Ala Thr Pro Ala Lys
705                 710                 715                 720 tcg gag taa                                                        2169
Ser Glu

<210> SEQ ID NO 8
<211> LENGTH: 722
<212> TYPE: PRT
<213> ORGANISM: Artificial Sequence
<220> FEATURE:
<223> OTHER INFORMATION: Synthetic Construct

<400> SEQUENCE: 8

Met Ala Ser Arg Leu Val Arg Val Leu Ala Ala Ala Met Leu Val Ala
1               5                   10                  15

Ala Ala Val Ser Val Asp Ala Leu Gln Gly Gly Met Leu Tyr Pro Gln
                20                  25                  30

Glu Ser Pro Ser Arg Glu Cys Lys Glu Leu Asp Gly Leu Trp Ser Phe
            35                  40                  45

Arg Ala Asp Phe Ser Asp Asn Arg Arg Gly Phe Glu Glu Gln Trp
        50                  55                  60

Tyr Arg Arg Pro Leu Trp Glu Ser Gly Pro Thr Val Asp Met Pro Val
65                  70                  75                  80

Pro Ser Ser Phe Asn Asp Ile Ser Gln Asp Trp Arg Leu Arg His Phe
                85                  90                  95

Val Gly Trp Val Trp Tyr Glu Arg Glu Val Ile Leu Pro Glu Arg Trp
            100                 105                 110

Thr Gln Asp Leu Arg Thr Arg Val Val Leu Arg Ile Gly Ser Ala His
```

```
            115                 120                 125
Ser Tyr Ala Ile Val Trp Val Asn Gly Val Asp Thr Leu Glu His Glu
130                 135                 140
Gly Gly Tyr Leu Pro Phe Glu Ala Asp Ile Ser Asn Leu Val Gln Val
145                 150                 155                 160
Gly Pro Leu Pro Ser Arg Leu Arg Ile Thr Ile Ala Ile Asn Asn Thr
                165                 170                 175
Leu Thr Pro Thr Thr Leu Pro Pro Gly Thr Ile Gln Tyr Leu Thr Asp
                180                 185                 190
Thr Ser Lys Tyr Pro Lys Gly Tyr Phe Val Gln Asn Thr Tyr Phe Asp
                195                 200                 205
Phe Phe Asn Tyr Ala Gly Leu Gln Arg Ser Val Leu Leu Tyr Thr Thr
210                 215                 220
Pro Thr Thr Tyr Ile Asp Asp Ile Thr Val Thr Ser Val Glu Gln
225                 230                 235                 240
Asp Ser Gly Leu Val Asn Tyr Gln Ile Ser Val Lys Gly Ser Asn Leu
                245                 250                 255
Phe Lys Leu Glu Val Arg Leu Leu Asp Ala Glu Asn Lys Val Val Ala
                260                 265                 270
Asn Gly Thr Gly Thr Gln Gly Gln Leu Lys Val Pro Gly Val Ser Leu
                275                 280                 285
Trp Trp Pro Tyr Leu Met His Glu Arg Pro Ala Tyr Leu Tyr Ser Leu
290                 295                 300
Glu Val Gln Leu Thr Ala Gln Thr Ser Leu Gly Pro Val Ser Asp Phe
305                 310                 315                 320
Tyr Thr Leu Pro Val Gly Ile Arg Thr Val Ala Val Thr Lys Ser Gln
                325                 330                 335
Phe Leu Ile Asn Gly Lys Pro Phe Tyr Phe His Gly Val Asn Lys His
                340                 345                 350
Glu Asp Ala Asp Ile Arg Gly Lys Gly Phe Asp Trp Pro Leu Leu Val
                355                 360                 365
Lys Asp Phe Asn Leu Leu Arg Trp Leu Gly Ala Asn Ala Phe Arg Thr
370                 375                 380
Ser His Tyr Pro Tyr Ala Glu Glu Val Met Gln Met Cys Asp Arg Tyr
385                 390                 395                 400
Gly Ile Val Val Ile Asp Glu Cys Pro Gly Val Gly Leu Ala Leu Pro
                405                 410                 415
Gln Phe Phe Asn Asn Val Ser Leu His His Met Gln Val Met Glu
                420                 425                 430
Glu Val Val Arg Arg Asp Lys Asn His Pro Ala Val Val Met Trp Ser
                435                 440                 445
Val Ala Asn Glu Pro Ala Ser His Leu Glu Ser Ala Gly Tyr Tyr Leu
450                 455                 460
Lys Met Val Ile Ala His Thr Lys Ser Leu Asp Pro Ser Arg Pro Val
465                 470                 475                 480
Thr Phe Val Ser Asn Ser Asn Tyr Ala Ala Asp Lys Gly Ala Pro Tyr
                485                 490                 495
Val Asp Val Ile Cys Leu Asn Ser Tyr Tyr Ser Trp Tyr His Asp Tyr
                500                 505                 510
Gly His Leu Glu Leu Ile Gln Leu Gln Leu Ala Thr Gln Phe Glu Asn
                515                 520                 525
Trp Tyr Lys Lys Tyr Gln Lys Pro Ile Ile Gln Ser Glu Tyr Gly Ala
530                 535                 540
```

```
Glu Thr Ile Ala Gly Phe His Gln Asp Pro Pro Leu Met Phe Thr Glu
545                 550                 555                 560

Glu Tyr Gln Lys Ser Leu Leu Glu Gln Tyr His Leu Gly Leu Asp Gln
            565                 570                 575

Lys Arg Arg Lys Tyr Val Val Gly Glu Leu Ile Trp Asn Phe Ala Asp
        580                 585                 590

Phe Met Thr Glu Gln Ser Pro Thr Arg Val Leu Gly Asn Lys Lys Gly
            595                 600                 605

Ile Phe Thr Arg Gln Arg Gln Pro Lys Ser Ala Ala Phe Leu Leu Arg
        610                 615                 620

Glu Arg Tyr Trp Lys Ile Ala Asn Glu Thr Arg Tyr Pro His Ser Val
625                 630                 635                 640

Ala Lys Ser Gln Cys Leu Glu Asn Ser Pro Phe Thr Gly Ala Pro Ala
            645                 650                 655

Tyr Arg Pro Ser Glu Thr Leu Cys Gly Gly Glu Leu Val Asp Thr Leu
        660                 665                 670

Gln Phe Val Cys Gly Asp Arg Gly Phe Tyr Phe Ser Arg Pro Ala Ser
            675                 680                 685

Arg Val Ser Arg Arg Ser Arg Gly Ile Val Glu Cys Cys Phe Arg
        690                 695                 700

Ser Cys Asp Leu Ala Leu Leu Glu Thr Tyr Cys Ala Thr Pro Ala Lys
705                 710                 715                 720

Ser Glu

<210> SEQ ID NO 9
<211> LENGTH: 722
<212> TYPE: PRT
<213> ORGANISM: Artificial Sequence
<220> FEATURE:
<223> OTHER INFORMATION: Synthetic Construct

<400> SEQUENCE: 9

Met Ala Ser Arg Leu Val Arg Val Leu Ala Ala Ala Met Leu Val Ala
1               5                   10                  15

Ala Ala Val Ser Val Asp Ala Leu Gln Gly Gly Met Leu Tyr Pro Gln
            20                  25                  30

Glu Ser Pro Ser Arg Glu Cys Lys Glu Leu Asp Gly Leu Trp Ser Phe
        35                  40                  45

Arg Ala Asp Phe Ser Asp Asn Arg Arg Gly Phe Glu Glu Gln Trp
    50                  55                  60

Tyr Arg Arg Pro Leu Trp Glu Ser Gly Pro Thr Val Asp Met Pro Val
65                  70                  75                  80

Pro Ser Ser Phe Asn Asp Ile Ser Gln Asp Trp Arg Leu Arg His Phe
                85                  90                  95

Val Gly Trp Val Trp Tyr Glu Arg Glu Val Ile Leu Pro Glu Arg Trp
            100                 105                 110

Thr Gln Asp Leu Arg Thr Arg Val Val Leu Arg Ile Gly Ser Ala His
        115                 120                 125

Ser Tyr Ala Ile Val Trp Val Asn Gly Val Asp Thr Leu Glu His Glu
    130                 135                 140

Gly Gly Tyr Leu Pro Phe Glu Ala Asp Ile Ser Asn Leu Val Gln Val
145                 150                 155                 160

Gly Pro Leu Pro Ser Arg Leu Arg Ile Thr Ile Ala Ile Asn Asn Thr
                165                 170                 175

Leu Thr Pro Thr Thr Leu Pro Pro Gly Thr Ile Gln Tyr Leu Thr Asp
            180                 185                 190
```

```
Thr Ser Lys Tyr Pro Lys Gly Tyr Phe Val Gln Asn Thr Tyr Phe Asp
            195                 200                 205

Phe Phe Asn Tyr Ala Gly Leu Gln Arg Ser Val Leu Leu Tyr Thr Thr
        210                 215                 220

Pro Thr Thr Tyr Ile Asp Asp Ile Thr Val Thr Thr Ser Val Glu Gln
225                 230                 235                 240

Asp Ser Gly Leu Val Asn Tyr Gln Ile Ser Val Lys Gly Ser Asn Leu
                245                 250                 255

Phe Lys Leu Glu Val Arg Leu Leu Asp Ala Glu Asn Lys Val Val Ala
            260                 265                 270

Asn Gly Thr Gly Thr Gln Gly Gln Leu Lys Val Pro Gly Val Ser Leu
        275                 280                 285

Trp Trp Pro Tyr Leu Met His Glu Arg Pro Ala Tyr Leu Tyr Ser Leu
        290                 295                 300

Glu Val Gln Leu Thr Ala Gln Thr Ser Leu Gly Pro Val Ser Asp Phe
305                 310                 315                 320

Tyr Thr Leu Pro Val Gly Ile Arg Thr Val Ala Val Thr Lys Ser Gln
                325                 330                 335

Phe Leu Ile Asn Gly Lys Pro Phe Tyr Phe His Gly Val Asn Lys His
            340                 345                 350

Glu Asp Ala Asp Ile Arg Gly Lys Gly Phe Asp Trp Pro Leu Leu Val
        355                 360                 365

Lys Asp Phe Asn Leu Leu Arg Trp Leu Gly Ala Asn Ala Phe Arg Thr
        370                 375                 380

Ser His Tyr Pro Tyr Ala Glu Glu Val Met Gln Met Cys Asp Arg Tyr
385                 390                 395                 400

Gly Ile Val Val Ile Asp Glu Cys Pro Gly Val Gly Leu Ala Leu Pro
                405                 410                 415

Gln Phe Phe Asn Asn Val Ser Leu His His His Met Gln Val Met Glu
            420                 425                 430

Glu Val Val Arg Arg Asp Lys Asn His Pro Ala Val Val Met Trp Ser
        435                 440                 445

Val Ala Asn Glu Pro Ala Ser His Leu Glu Ser Ala Gly Tyr Tyr Leu
450                 455                 460

Lys Met Val Ile Ala His Thr Lys Ser Leu Asp Pro Ser Arg Pro Val
465                 470                 475                 480

Thr Phe Val Ser Asn Ser Asn Tyr Ala Ala Asp Lys Gly Ala Pro Tyr
                485                 490                 495

Val Asp Val Ile Cys Leu Asn Ser Tyr Tyr Ser Trp Tyr His Asp Tyr
            500                 505                 510

Gly His Leu Glu Leu Ile Gln Leu Gln Leu Ala Thr Gln Phe Glu Asn
        515                 520                 525

Trp Tyr Lys Lys Tyr Gln Lys Pro Ile Ile Gln Ser Glu Tyr Gly Ala
        530                 535                 540

Glu Thr Ile Ala Gly Phe His Gln Asp Pro Pro Leu Met Phe Thr Glu
545                 550                 555                 560

Glu Tyr Gln Lys Ser Leu Leu Glu Gln Tyr His Leu Gly Leu Asp Gln
                565                 570                 575

Lys Arg Arg Lys Tyr Val Val Gly Glu Leu Ile Trp Asn Phe Ala Asp
            580                 585                 590

Phe Met Thr Glu Gln Ser Pro Thr Arg Val Leu Gly Asn Lys Lys Gly
        595                 600                 605

Ile Phe Thr Arg Gln Arg Gln Pro Lys Ser Ala Ala Phe Leu Leu Arg
```

```
                        610                 615                 620
Glu Arg Tyr Trp Lys Ile Ala Asn Glu Thr Arg Tyr Pro His Ser Val
625                 630                 635                 640

Ala Lys Ser Gln Cys Leu Glu Asn Ser Pro Phe Thr Gly Ala Pro Ala
                645                 650                 655

Tyr Arg Pro Ser Glu Thr Leu Cys Gly Gly Glu Leu Val Asp Thr Leu
                    660                 665                 670

Gln Phe Val Cys Gly Asp Arg Gly Phe Tyr Phe Ser Arg Pro Ala Ser
                675                 680                 685

Arg Val Ser Arg Arg Ser Arg Gly Ile Val Glu Glu Cys Cys Phe Arg
                690                 695                 700

Ser Cys Asp Leu Ala Leu Leu Glu Thr Tyr Cys Ala Thr Pro Ala Lys
705                 710                 715                 720

Ser Glu

<210> SEQ ID NO 10
<211> LENGTH: 70
<212> TYPE: PRT
<213> ORGANISM: Homo sapiens

<400> SEQUENCE: 10

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
50                  55                  60

Lys Pro Ala Lys Ser Ala
65                  70

<210> SEQ ID NO 11
<211> LENGTH: 67
<212> TYPE: PRT
<213> ORGANISM: Homo sapiens

<400> SEQUENCE: 11

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
                20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
50                  55                  60

Lys Ser Glu
65

<210> SEQ ID NO 12
<211> LENGTH: 50
<212> TYPE: DNA
<213> ORGANISM: Artificial Sequence
<220> FEATURE:
<223> OTHER INFORMATION: Oligonucleotide GILT 1

<400> SEQUENCE: 12
gcggcggcga gctggtggac acgctgcagt tcgtgtgcgg cgaccgcggc            50
```

```
<210> SEQ ID NO 13
<211> LENGTH: 50
<212> TYPE: DNA
<213> ORGANISM: Artificial Sequence
<220> FEATURE:
<223> OTHER INFORMATION: Oligonucleotide GILT 2

<400> SEQUENCE: 13
ttctacttca gccgcccggc cagccgcgtg agccgccgca gccgcggcat          50

<210> SEQ ID NO 14
<211> LENGTH: 50
<212> TYPE: DNA
<213> ORGANISM: Artificial Sequence
<220> FEATURE:
<223> OTHER INFORMATION: Oligonucleotide GILT 3

<400> SEQUENCE: 14
cgtggaggag tgctgcttcc gcagctgcga cctggcgctg ctggagacgt          50

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide GILT 4

<400> SEQUENCE: 15
actgcgcgac gccggcgaag tcggagtaag atctagagcg                    40

<210> SEQ ID NO 16
<211> LENGTH: 50
<212> TYPE: DNA
<213> ORGANISM: Artificial Sequence
<220> FEATURE:
<223> OTHER INFORMATION: Oligonucleotide GILT 5

<400> SEQUENCE: 16
agcgtgtcca ccagctcgcc gccgcacagc gtctcgctcg ggcggtacgc          50

<210> SEQ ID NO 17
<211> LENGTH: 50
<212> TYPE: DNA
<213> ORGANISM: Artificial Sequence
<220> FEATURE:
<223> OTHER INFORMATION: Oligonucleotide GILT 6

<400> SEQUENCE: 17
ggctggccgg gcggctgaag tagaagccgc ggtcgccgca cacgaactgc          50

<210> SEQ ID NO 18
<211> LENGTH: 50
<212> TYPE: DNA
<213> ORGANISM: Artificial Sequence
<220> FEATURE:
<223> OTHER INFORMATION: Oligonucleotide GILT 7

<400> SEQUENCE: 18
gctgcggaag cagcactcct ccacgatgcc gcggctgcgg cggctcacgc          50

<210> SEQ ID NO 19
<211> LENGTH: 51
<212> TYPE: DNA
<213> ORGANISM: Artificial Sequence
<220> FEATURE:
<223> OTHER INFORMATION: Oligonucleotide GILT 8
```

-continued

```
<400> SEQUENCE: 19
ctccgacttc gccggcgtcg cgcagtacgt ctccagcagc gccaggtcgc a        51

<210> SEQ ID NO 20
<211> LENGTH: 47
<212> TYPE: DNA
<213> ORGANISM: Artificial Sequence
<220> FEATURE:
<223> OTHER INFORMATION: Oligonucleotide GILT 9

<400> SEQUENCE: 20
ccgtctagag ctcggcgcgc cggcgtaccg cccgagcgag acgctgt              47

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide GILT 10

<400> SEQUENCE: 21
cgctctagat cttactccga cttcg                                      25

<210> SEQ ID NO 22
<211> LENGTH: 46
<212> TYPE: DNA
<213> ORGANISM: Artificial Sequence
<220> FEATURE:
<223> OTHER INFORMATION: Oligonucleotide GILT 11

<400> SEQUENCE: 22
ccgtctagag ctcggcgcgc cgctgtgcgg cggcgagctg gtggac               46

<210> SEQ ID NO 23
<211> LENGTH: 50
<212> TYPE: DNA
<213> ORGANISM: Artificial Sequence
<220> FEATURE:
<223> OTHER INFORMATION: Oligonucleotide GILT 12

<400> SEQUENCE: 23
ttcctgttca gccgcccggc cagccgcgtg agccgccgca gccgcggcat            50

<210> SEQ ID NO 24
<211> LENGTH: 50
<212> TYPE: DNA
<213> ORGANISM: Artificial Sequence
<220> FEATURE:
<223> OTHER INFORMATION: Oligonucleotide GILT 16

<400> SEQUENCE: 24
ggctggccgg gcggctgaac aggaagccgc ggtcgccgca cacgaactgc            50

<210> SEQ ID NO 25
<211> LENGTH: 25
<212> TYPE: DNA
<213> ORGANISM: Artificial Sequence
<220> FEATURE:
<223> OTHER INFORMATION: Oligonucleotide GILT 20

<400> SEQUENCE: 25
ccgtctagag ctcggcgcgc cggcg                                      25

<210> SEQ ID NO 26
<211> LENGTH: 2851
<212> TYPE: DNA
```

<213> ORGANISM: Homo sapiens
<220> FEATURE:
<221> NAME/KEY: CDS
<222> LOCATION: (1)..(2850)

<400> SEQUENCE: 26

```
atg gga gtg agg cac ccg ccc tgc tcc cac cgg ctc ctg gcc gtc tgc      48
Met Gly Val Arg His Pro Pro Cys Ser His Arg Leu Leu Ala Val Cys
1               5                   10                  15 gcc ctc gtg tcc ttg gca acc gct gca ctc ctg ggg cac atc cta ctc      96
Ala Leu Val Ser Leu Ala Thr Ala Ala Leu Leu Gly His Ile Leu Leu
                20                  25                  30 cat gat ttc ctg ctg gtt ccc cga gag ctg agt ggc tcc tcc cca gtc     144
His Asp Phe Leu Leu Val Pro Arg Glu Leu Ser Gly Ser Ser Pro Val
            35                  40                  45 ctg gag gag act cac cca gct cac cag cag gga gcc agc aga cca ggg     192
Leu Glu Glu Thr His Pro Ala His Gln Gln Gly Ala Ser Arg Pro Gly
        50                  55                  60 ccc cgg gat gcc cag gca cac ccc ggc gtc ccc aga gca gtg ccc aca     240
Pro Arg Asp Ala Gln Ala His Pro Gly Val Pro Arg Ala Val Pro Thr
65                  70                  75                  80 cag tgc gac gtc ccc ccc aac agc cgc ttc gat tgc gcc cct gac aag     288
Gln Cys Asp Val Pro Pro Asn Ser Arg Phe Asp Cys Ala Pro Asp Lys
                85                  90                  95 gcc atc acc cag gaa cag tgc gag gcc cgc ggc tgc tgc tac atc cct     336
Ala Ile Thr Gln Glu Gln Cys Glu Ala Arg Gly Cys Cys Tyr Ile Pro
                100                 105                 110 gca aag cag ggg ctg cag gga gcc cag atg ggg cag ccc tgg tgc ttc     384
Ala Lys Gln Gly Leu Gln Gly Ala Gln Met Gly Gln Pro Trp Cys Phe
            115                 120                 125 ttc cca ccc agc tac ccc agc tac aag ctg gag aac ctg agc tcc tct     432
Phe Pro Pro Ser Tyr Pro Ser Tyr Lys Leu Glu Asn Leu Ser Ser Ser
        130                 135                 140 gaa atg ggc tac acg gcc acc ctg acc cgt acc acc ccc acc ttc ttc     480
Glu Met Gly Tyr Thr Ala Thr Leu Thr Arg Thr Thr Pro Thr Phe Phe
145                 150                 155                 160 ccc aag gac atc ctg acc ctg cgg ctg gac gtg atg atg gag act gag     528
Pro Lys Asp Ile Leu Thr Leu Arg Leu Asp Val Met Met Glu Thr Glu
                165                 170                 175 aac cgc ctc cac ttc acg atc aaa gat cca gct aac agg cgc tac gag     576
Asn Arg Leu His Phe Thr Ile Lys Asp Pro Ala Asn Arg Arg Tyr Glu
                180                 185                 190 gtg ccc ttg gag acc ccg cgt gtc cac agc cgg gca ccg tcc cca ctc     624
Val Pro Leu Glu Thr Pro Arg Val His Ser Arg Ala Pro Ser Pro Leu
            195                 200                 205 tac agc gtg gag ttc tct gag gag ccc ttc ggg gtg atc gtg cac cgg     672
Tyr Ser Val Glu Phe Ser Glu Glu Pro Phe Gly Val Ile Val His Arg
        210                 215                 220 cag ctg gac ggc cgc gtg ctg ctg aac acg acg gtg gcg ccc ctg ttc     720
Gln Leu Asp Gly Arg Val Leu Leu Asn Thr Thr Val Ala Pro Leu Phe
225                 230                 235                 240 ttt gcg gac cag ttc ctt cag ctg tcc acc tcg ctg ccc tcg cag tat     768
Phe Ala Asp Gln Phe Leu Gln Leu Ser Thr Ser Leu Pro Ser Gln Tyr
                245                 250                 255 atc aca ggc ctc gcc gag cac ctc agt ccc ctg atg ctc agc acc agc     816
Ile Thr Gly Leu Ala Glu His Leu Ser Pro Leu Met Leu Ser Thr Ser
                260                 265                 270 tgg acc agg atc acc ctg tgg aac cgg gac ctt gcg ccc acg ccc ggt     864
Trp Thr Arg Ile Thr Leu Trp Asn Arg Asp Leu Ala Pro Thr Pro Gly
            275                 280                 285 gcg aac ctc tac ggg tct cac cct ttc tac ctg gcg ctg gag gac ggc     912
Ala Asn Leu Tyr Gly Ser His Pro Phe Tyr Leu Ala Leu Glu Asp Gly
```

```
                  Ala Asn Leu Tyr Gly Ser His Pro Phe Tyr Leu Ala Leu Glu Asp Gly
                      290                 295                 300 ggg tcg gca cac ggg gtg ttc ctg cta aac agc aat gcc atg gat gtg         960
Gly Ser Ala His Gly Val Phe Leu Leu Asn Ser Asn Ala Met Asp Val
305                 310                 315                 320 gtc ctg cag ccg agc cct gcc ctt agc tgg agg tcg aca ggt ggg atc        1008
Val Leu Gln Pro Ser Pro Ala Leu Ser Trp Arg Ser Thr Gly Gly Ile
                325                 330                 335 ctg gat gtc tac atc ttc ctg ggc cca gag ccc aag agc gtg gtg cag        1056
Leu Asp Val Tyr Ile Phe Leu Gly Pro Glu Pro Lys Ser Val Val Gln
                340                 345                 350 cag tac ctg gac gtt gtg gga tac ccg ttc atg ccg cca tac tgg ggc        1104
Gln Tyr Leu Asp Val Val Gly Tyr Pro Phe Met Pro Pro Tyr Trp Gly
            355                 360                 365 ctg ggc ttc cac ctg tgc cgc tgg ggc tac tcc tcc acc gct atc acc        1152
Leu Gly Phe His Leu Cys Arg Trp Gly Tyr Ser Ser Thr Ala Ile Thr
        370                 375                 380 cgc cag gtg gtg gag aac atg acc agg gcc cac ttc ccc ctg gac gtc        1200
Arg Gln Val Val Glu Asn Met Thr Arg Ala His Phe Pro Leu Asp Val
385                 390                 395                 400 caa tgg aac gac ctg gac tac atg gac tcc cgg agg gac ttc acg ttc        1248
Gln Trp Asn Asp Leu Asp Tyr Met Asp Ser Arg Arg Asp Phe Thr Phe
                405                 410                 415 aac aag gat ggc ttc cgg gac ttc ccg gcc atg gtg cag gag ctg cac        1296
Asn Lys Asp Gly Phe Arg Asp Phe Pro Ala Met Val Gln Glu Leu His
                420                 425                 430 cag ggc ggc cgg cgc tac atg atg atc gtg gat cct gcc atc agc agc        1344
Gln Gly Gly Arg Arg Tyr Met Met Ile Val Asp Pro Ala Ile Ser Ser
            435                 440                 445 tcg ggc cct gcc ggg agc tac agg ccc tac gac gag ggt ctg cgg agg        1392
Ser Gly Pro Ala Gly Ser Tyr Arg Pro Tyr Asp Glu Gly Leu Arg Arg
        450                 455                 460 ggg gtt ttc atc acc aac gag acc ggc cag ccg ctg att ggg aag gta        1440
Gly Val Phe Ile Thr Asn Glu Thr Gly Gln Pro Leu Ile Gly Lys Val
465                 470                 475                 480 tgg ccc ggg tcc act gcc ttc ccc gac ttc acc aac ccc aca gcc ctg        1488
Trp Pro Gly Ser Thr Ala Phe Pro Asp Phe Thr Asn Pro Thr Ala Leu
                485                 490                 495 gcc tgg tgg gag gac atg gtg gct gag ttc cat gac cag gtg ccc ttc        1536
Ala Trp Trp Glu Asp Met Val Ala Glu Phe His Asp Gln Val Pro Phe
                500                 505                 510 gac ggc atg tgg att gac atg aac gag cct tcc aac ttc atc agg ggc        1584
Asp Gly Met Trp Ile Asp Met Asn Glu Pro Ser Asn Phe Ile Arg Gly
            515                 520                 525 tct gag gac ggc tgc ccc aac aat gag ctg gag aac cca ccc tac gtg        1632
Ser Glu Asp Gly Cys Pro Asn Asn Glu Leu Glu Asn Pro Pro Tyr Val
        530                 535                 540 cct ggg gtg gtt ggg ggg acc ctc cag gcg gca acc atc tgt gcc tcc        1680
Pro Gly Val Val Gly Gly Thr Leu Gln Ala Ala Thr Ile Cys Ala Ser
545                 550                 555                 560 agc cac cag ttt ctc tcc aca cac tac aac ctg cac aac ctc tac ggc        1728
Ser His Gln Phe Leu Ser Thr His Tyr Asn Leu His Asn Leu Tyr Gly
                565                 570                 575 ctg acc gaa gcc atc gcc tcc cac agg gcg ctg gtg aag gct cgg ggg        1776
Leu Thr Glu Ala Ile Ala Ser His Arg Ala Leu Val Lys Ala Arg Gly
                580                 585                 590 aca cgc cca ttt gtg atc tcc cgc tcg acc ttt gct ggc cac ggc cga        1824
Thr Arg Pro Phe Val Ile Ser Arg Ser Thr Phe Ala Gly His Gly Arg
            595                 600                 605 tac gcc ggc cac tgg acg ggg gac gtg tgg agc tcc tgg gag cag ctc        1872
```

```
                Tyr Ala Gly His Trp Thr Gly Asp Val Trp Ser Ser Trp Glu Gln Leu
                    610                 615                 620 gcc tcc tcc gtg cca gaa atc ctg cag ttt aac ctg ctg ggg gtg cct      1920
Ala Ser Ser Val Pro Glu Ile Leu Gln Phe Asn Leu Leu Gly Val Pro
625                 630                 635                 640 ctg gtc ggg gcc gac gtc tgc ggc ttc ctg ggc aac acc tca gag gag      1968
Leu Val Gly Ala Asp Val Cys Gly Phe Leu Gly Asn Thr Ser Glu Glu
                645                 650                 655 ctg tgt gtg cgc tgg acc cag ctg ggg gcc ttc tac ccc ttc atg cgg      2016
Leu Cys Val Arg Trp Thr Gln Leu Gly Ala Phe Tyr Pro Phe Met Arg
            660                 665                 670 aac cac aac agc ctg ctc agt ctg ccc cag gag ccg tac agc ttc agc      2064
Asn His Asn Ser Leu Leu Ser Leu Pro Gln Glu Pro Tyr Ser Phe Ser
        675                 680                 685 gag ccg gcc cag cag gcc atg agg aag gcc ctc acc ctg cgc tac gca      2112
Glu Pro Ala Gln Gln Ala Met Arg Lys Ala Leu Thr Leu Arg Tyr Ala
    690                 695                 700 ctc ctc ccc cac ctc tac acg ctg ttc cac cag gcc cac gtc gcg ggg      2160
Leu Leu Pro His Leu Tyr Thr Leu Phe His Gln Ala His Val Ala Gly
705                 710                 715                 720 gag acc gtg gcc cgg ccc ctc ttc ctg gag ttc ccc aag gac tct agc      2208
Glu Thr Val Ala Arg Pro Leu Phe Leu Glu Phe Pro Lys Asp Ser Ser
                725                 730                 735 acc tgg act gtg gac cac cag ctc ctg tgg ggg gag gcc ctc ctc atc      2256
Thr Trp Thr Val Asp His Gln Leu Leu Trp Gly Glu Ala Leu Leu Ile
                740                 745                 750 acc cca gtg ctc cag gcc ggg aag gcc gaa gtg act ggc tac ttc ccc      2304
Thr Pro Val Leu Gln Ala Gly Lys Ala Glu Val Thr Gly Tyr Phe Pro
            755                 760                 765 ttg ggc aca tgg tac gac ctg cag acg gtg cca ata gag gcc ctt ggc      2352
Leu Gly Thr Trp Tyr Asp Leu Gln Thr Val Pro Ile Glu Ala Leu Gly
        770                 775                 780 agc ctc cca ccc cca cct gca gct ccc cgt gag cca gcc atc cac agc      2400
Ser Leu Pro Pro Pro Pro Ala Ala Pro Arg Glu Pro Ala Ile His Ser
785                 790                 795                 800 gag ggg cag tgg gtg acg ctg ccg gcc ccc ctg gac acc atc aac gtc      2448
Glu Gly Gln Trp Val Thr Leu Pro Ala Pro Leu Asp Thr Ile Asn Val
                805                 810                 815 cac ctc cgg gct ggg tac atc atc ccc ctg cag ggc cct ggc ctc aca      2496
His Leu Arg Ala Gly Tyr Ile Ile Pro Leu Gln Gly Pro Gly Leu Thr
                820                 825                 830 acc aca gag tcc cgc cag cag ccc atg gcc ctg gct gtg gcc ctg acc      2544
Thr Thr Glu Ser Arg Gln Gln Pro Met Ala Leu Ala Val Ala Leu Thr
            835                 840                 845 aag ggt gga gag gcc cga ggg gag ctg ttc tgg gac gat gga gag agc      2592
Lys Gly Gly Glu Ala Arg Gly Glu Leu Phe Trp Asp Asp Gly Glu Ser
        850                 855                 860 ctg gaa gtg ctg gag cga ggg gcc tac aca cag gtc atc ttc ctg gcc      2640
Leu Glu Val Leu Glu Arg Gly Ala Tyr Thr Gln Val Ile Phe Leu Ala
865                 870                 875                 880 agg aat aac acg atc gtg aat gag ctg gta cgt gtg acc agt gag gga      2688
Arg Asn Asn Thr Ile Val Asn Glu Leu Val Arg Val Thr Ser Glu Gly
                885                 890                 895 gct ggc ctg cag ctg cag aag gtg act gtc ctg ggc gtg gcc acg gcg      2736
Ala Gly Leu Gln Leu Gln Lys Val Thr Val Leu Gly Val Ala Thr Ala
                900                 905                 910 ccc cag cag gtc ctc tcc aac ggt gtc cct gtc tcc aac ttc acc tac      2784
Pro Gln Gln Val Leu Ser Asn Gly Val Pro Val Ser Asn Phe Thr Tyr
            915                 920                 925 agc ccc gac acc aag gtc ctg gac atc tgt gtc tcg ctg ttg atg gga      2832
```

```
Ser Pro Asp Thr Lys Val Leu Asp Ile Cys Val Ser Leu Leu Met Gly
        930                 935                 940 gag cag ttt ctc gtc agc t                                           2851
Glu Gln Phe Leu Val Ser
945                 950

<210> SEQ ID NO 27
<211> LENGTH: 950
<212> TYPE: PRT
<213> ORGANISM: Homo sapiens

<400> SEQUENCE: 27

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350
```

```
Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
```

|  |  |  | 770 |  |  |  | 775 |  |  |  | 780 |  |
|---|---|---|---|---|---|---|---|---|---|---|---|---|
| Ser | Leu | Pro | Pro | Pro | Ala | Ala | Pro | Arg | Glu | Pro | Ala | Ile | His | Ser |
| 785 |  |  |  |  | 790 |  |  |  |  | 795 |  |  |  | 800 |

| Glu | Gly | Gln | Trp | Val | Thr | Leu | Pro | Ala | Pro | Leu | Asp | Thr | Ile | Asn | Val |
|---|---|---|---|---|---|---|---|---|---|---|---|---|---|---|---|
|  |  |  |  | 805 |  |  |  |  | 810 |  |  |  |  | 815 |  |

| His | Leu | Arg | Ala | Gly | Tyr | Ile | Ile | Pro | Leu | Gln | Gly | Pro | Gly | Leu | Thr |
|---|---|---|---|---|---|---|---|---|---|---|---|---|---|---|---|
|  |  |  | 820 |  |  |  |  | 825 |  |  |  |  | 830 |  |  |

| Thr | Thr | Glu | Ser | Arg | Gln | Gln | Pro | Met | Ala | Leu | Ala | Val | Ala | Leu | Thr |
|---|---|---|---|---|---|---|---|---|---|---|---|---|---|---|---|
|  |  |  | 835 |  |  |  |  | 840 |  |  |  |  | 845 |  |  |

| Lys | Gly | Gly | Glu | Ala | Arg | Gly | Glu | Leu | Phe | Trp | Asp | Asp | Gly | Glu | Ser |
|---|---|---|---|---|---|---|---|---|---|---|---|---|---|---|---|
|  | 850 |  |  |  |  | 855 |  |  |  |  | 860 |  |  |  |  |

| Leu | Glu | Val | Leu | Glu | Arg | Gly | Ala | Tyr | Thr | Gln | Val | Ile | Phe | Leu | Ala |
|---|---|---|---|---|---|---|---|---|---|---|---|---|---|---|---|
| 865 |  |  |  |  | 870 |  |  |  |  | 875 |  |  |  |  | 880 |

| Arg | Asn | Asn | Thr | Ile | Val | Asn | Glu | Leu | Val | Arg | Val | Thr | Ser | Glu | Gly |
|---|---|---|---|---|---|---|---|---|---|---|---|---|---|---|---|
|  |  |  |  | 885 |  |  |  |  | 890 |  |  |  |  | 895 |  |

| Ala | Gly | Leu | Gln | Leu | Gln | Lys | Val | Thr | Val | Leu | Gly | Val | Ala | Thr | Ala |
|---|---|---|---|---|---|---|---|---|---|---|---|---|---|---|---|
|  |  |  | 900 |  |  |  |  | 905 |  |  |  |  | 910 |  |  |

| Pro | Gln | Gln | Val | Leu | Ser | Asn | Gly | Val | Pro | Val | Ser | Asn | Phe | Thr | Tyr |
|---|---|---|---|---|---|---|---|---|---|---|---|---|---|---|---|
|  |  |  | 915 |  |  |  |  | 920 |  |  |  |  | 925 |  |  |

| Ser | Pro | Asp | Thr | Lys | Val | Leu | Asp | Ile | Cys | Val | Ser | Leu | Leu | Met | Gly |
|---|---|---|---|---|---|---|---|---|---|---|---|---|---|---|---|
| 930 |  |  |  |  | 935 |  |  |  |  | 940 |  |  |  |  |  |

| Glu | Gln | Phe | Leu | Val | Ser |
|---|---|---|---|---|---|
| 945 |  |  |  |  | 950 |

<210> SEQ ID NO 28
<211> LENGTH: 1547
<212> TYPE: DNA
<213> ORGANISM: Artificial Sequence
<220> FEATURE:
<223> OTHER INFORMATION: An exemplary GILT-tagged alpha-GAL A cassette sequence

<400> SEQUENCE: 28

```
ctcgagaggt cgacggtatc gataagcttg atatcgaatt cgtgacaatg atgcagctga      60
ggaacccaga actacatctg gctgcgcgc ttgcgcttcg cttcctggcc ctcgtttcct     120
gggacatccc tgggctaga gcactggaca tggattggc aaggacgcct accatgggct     180
ggctgcactg ggagcgcttc atgtgcaacc ttgactgcca ggaagagcca gattcctgca    240
tcagtgagaa gctcttcatg agatggcag agctcatggt ctcagaaggc tggaaggatg    300
caggttatga gtacctctgc attgatgact gttggatggc tccccaaaga gattcagaag    360
gcagacttca ggcagaccct cagcgctttc ctcatgggat cgccagcta gctaattatg    420
ttcacagcaa aggactgaag ctagggattt atgcagatgt tggaaataaa acctgcgcag    480
gcttccctgg gagttttgga tactacgaca ttgatgccca gacctttgct gactggggag    540
tagatctgct aaaatttgat ggttgttact gtgacagttt ggaaaatttg cagatggtt    600
ataagcacat gtccttggcc ctgaatagga ctggcagaag cattgtgtac tcctgtgagt    660
ggcctcttta tatgtggccc tttcaaaaagc ccaattatac agaaatccga cagtactgca    720
atcactggcg aaattttgct gacattgatg attcctggaa aagtataaag agtatcttgg    780
actggacatc ttttaaccag agagaattg ttgatgttgc tggaccaggg ggttggaatg    840
acccagatat gttagtgatt ggcaactttg gcctcagctg gaatcagcaa gtaactcaga    900
tggccctctg gctatcatg gctgctcctt tattcatgtc taatgacctc cgacacatca    960
gccctcaagc caaagctctc cttcaggata aggacgtaat tgccatcaat caggacccct   1020
```

```
tgggcaagca agggtaccag cttagacagg agacaacttt tgaagtgtgg gaacgacctc    1080
tctcaggctt agcctgggct gtagctatga taaaccggca ggagattggt ggacctcgct    1140
cttataccat cgcagttgct tccctgggta aaggagtggc ctgtaatcct gcctgcttca    1200
tcacacagct cctccctgtg aaaggaagc tagggttcta tgaatggact tcaaggttaa     1260
gaagtcacat aaatcccaca ggcactgttt tgcttcagct agaaaataca atgcagatgt    1320
cattaaaaga cttacttggc gcgccgctgt cggcggcga gctggtggac acgctgcagt     1380
tcgtgtgcgg cgaccgcggc ttctacttca gccgcccggc cagccgcgtg agccgccgca    1440
gccgcggcat cgtggaggag tgctgcttcc gcagctgcga cctggcgctg ctggagacgt    1500
actgcgcgac gccggcgaag tcggagtaag aattcctgca gcccggg                  1547

<210> SEQ ID NO 29
<211> LENGTH: 1355
<212> TYPE: DNA
<213> ORGANISM: Homo sapiens

<400> SEQUENCE: 29
ctcgagaggt cgacggtatc gataagcttg atatcgaatt cgtgacaatg cagctgagga      60
acccagaact acatctgggc tgcgcgcttg cgcttcgctt cctggccctc gtttcctggg     120
acatccctgg ggctagagca ctggacaatg gattggcaag gacgcctacc atgggctggc     180
tgcactggga gcgcttcatg tgcaaccttg actgccagga gagccagat tcctgcatca      240 gtgagaagct cttcatggag atggcagagc tcatggtctc agaaggctgg aaggatgcag     300
gttatgagta cctctgcatt gatgactgtt ggatggctcc ccaaagagat tcagaaggca    360
gacttcaggc agaccctcag cgcttcctc atgggattcg ccagctagct aattatgttc     420
acagcaaagg actgaagcta gggatttatg cagatgttgg aaataaaacc tgcgcaggct    480
tccctgggag ttttggatac tacgacattg atgcccagac ctttgctgac tggggagtag    540
atctgctaaa atttgatggt tgttactgtg acagtttgga aaatttggca gatggttata    600
agcacatgtc cttggccctg aataggactg gcagaagcat tgtgtactcc tgtgagtggc    660
ctctttatat gtgccctttt caaaagccca attatacaga aatccgacag tactgcaatc    720
actggcgaaa ttttgctgac attgatgatt cctggaaaag tataaagagt atcttggact    780
ggacatcttt taaccaggag agaattgttg atgttgctgg accaggggt tggaatgacc     840 cagatatgtt agtgattggc aactttggcc tcagctggaa tcagcaagta actcagatgg    900
ccctctgggc tatcatggct gctcctttat tcatgtctaa tgacctccga cacatcagcc    960
ctcaagccaa agctctcctt caggataagg acgtaattgc catcaatcag gaccccttgg   1020
gcaagcaagg gtaccagctt agacaggag acaactttga agtgtgggaa cgacctctct    1080
caggcttagc ctgggctgta gctatgataa accggcagga gattggtgga cctcgctctt    1140
ataccatcgc agttgcttcc ctgggtaaag gagtggcctg taatcctgcc tgcttcatca    1200
cacagctcct ccctgtgaaa aggaagctag ggttctatga atggacttca aggttaagaa    1260
gtcacataaa tcccacaggc actgttttgc ttcagctaga aaatacaatg cagatgtcat    1320
taaaagactt actttaagaa ttcctgcagc ccggg                              1355

<210> SEQ ID NO 30
<211> LENGTH: 3913
<212> TYPE: DNA
<213> ORGANISM: Artificial Sequence
<220> FEATURE:
<223> OTHER INFORMATION: Sequence of pISSWA vector
```

```
<400> SEQUENCE: 30
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt      540
acggtgggag gtctatataa gcagagctcg tttagtgaac cgtcagatcg cctggagacg     600
ccatccacgc tgttttgacc tccatagaag acaccgggac cgatccagcc tccgcggccg     660
ggaacggtgc attggaacgc ggattccccg tgccaagagt gacgtaagta ccgcctatag     720
actctatagg cacacccctt tggctcttat gcatgaatta atacgactca ctatagggag     780
acagactgtt cctttcctgg gtcttttctg caggcaccgt cgtcgactta acagatctcg     840
agctcaagct tcgaattctg cagtcgacgg taccgcgggc ccgggatcca ccgggtacaa     900
gtaaagcggc cgcgactcta gatcataatc agccatacca catttgtaga ggttttactt     960
gctttaaaaa acctcccaca cctccccctg aacctgaaac ataaaatgaa tgcaattgtt    1020
gttgttaact tgtttattgc agcttataat ggttacaaat aaagcaatag catcacaaat    1080
ttcacaaata aagcattttt ttcactgcat tctagttgtg gtttgtccaa actcatcaat    1140
gtatcttaaa tttaaatggc tttacacttt atgcttccgg ctcgtataat gtgcactacg    1200
tgaaccatca ccctaatcaa gttttttggg gtcgaggtgc cgtaaagcac taaatcggaa    1260
ccctaaaggg agcccccgat ttagagcttg acggggaaag ccggcgaacg tggcgagaaa    1320
ggaagggaag aaagcgaaag gagcgggcgc tagggcgctg gcaagtgtag cggtcacgct    1380
gcgcgtaacc accacacccg ccgcgcttaa tgcgccgcta cagggcgcgt caggtggcac    1440
ttttcgggga aatgtgcgcg gaaccccttt ttgtttattt ttctaaatac attcaaatat    1500
gtatccgctc atgagacaat aaccctgata aatgcttcaa taatattgaa aaaggaagag    1560
tcctgaggcg gaaagaacca gtctcaatta gtcagcaacc atagtcccgc ccctaactcc    1620
gcccatcccg cccctaactc cgcccagttc cgcccattct ccgccccatg gctgactaat    1680
ttttttttatt tatgcagagg ccgaggccgc ctcggcctct gagctattcc agaagtagtg    1740
aggaggcttt tttggaggcc taggctttg caaagatcga tcaagagaca ggatgaggat    1800
cgtttcgcat gattgaacaa gatggattgc acgcaggttc tccggccgct tgggtggaga    1860
ggctattcgg ctatgactgg gcacaacaga caatcggctg ctctgatgcc gccgtgttcc    1920
ggctgtcagc gcaggggcgc ccggttcttt ttgtcaagac cgacctgtcc ggtgccctga    1980
atgaactgca agacgaggca gcgcggctat cgtggctggc cacgacgggc gttccttgcg    2040
cagctgtgct cgacgttgtc actgaagcgg gaagggactg gctgctattg ggcgaagtgc    2100
cggggcagga tctcctgtca tctcaccttg ctcctgccga aaagtatcc atcatggctg    2160
atgcaatgcg gcggctgcat acgcttgatc cggctacctg cccattcgac caccaagcga    2220
aacatcgcat cgagcgagca cgtactcgga tggaagccgg tcttgtcgat caggatgatc    2280
tggacgaaga gcatcagggg ctcgcgccag ccgaactgtt cgccaggctc aaggcgagca    2340
```

```
tgcccgacgg cgatgatctc gtcgtgaccc atggcgatgc ctgcttgccg aatatcatgg    2400
tggaaaatgg ccgcttttct ggattcatcg actgtggccg gctgggtgtg gcggaccgct    2460
atcaggacat agcgttggct acccgtgata ttgctgaaga gcttggcggc gaatgggctg    2520
accgcttcct cgtgctttac ggtatcgccg ctcccgattc gcagcgcatc gccttctatc    2580
gccttcttga cgagttcttc tgagcgggac tctggggttc gaaatgaccg accaagcgac    2640
gcccaacctg ccatcacgag atttcgattc caccgccgcc ttctatgaaa ggttgggctt    2700
cggaatcgtt ttccgggacg ccggctggat gatcctccag cgcgggatc tcatgctgga     2760 gttcttcgcc caccctaggg ggaggctaac tgaaacacgg aaggagacaa taccggaagg    2820
aacccgcgct atgacggcaa taaaaagaca gaataaaacg cacggtgttg ggtcgtttgt    2880
tcataaacgc ggggttcggt cccagggctg gcactctgtc gatacccccac cgagaccccca  2940 ttggggccaa tacgcccgcg tttcttcctt ttccccaccc caccccccaa gttcgggtga    3000
aggcccaggg ctcgcagcca acgtcggggc ggcaggccct gccatagcct caggttactc    3060
atatatactt tagattgatt taaaacttca tttttaattt aaaaggatct aggtgaagat    3120 ccttttttgat aatctcatga ccaaaatccc ttaacgtgag ttttcgttcc actgagcgtc   3180 agacccgta gaaaagatca aaggatcttc ttgagatcct ttttttctgc gcgtaatctg     3240
ctgcttgcaa acaaaaaaac caccgctacc agcggtggtt tgtttgccgg atcaagagct    3300
accaactctt tttccgaagg taactggctt cagcagagcg cagataccaa atactgtcct    3360
tctagtgtag ccgtagttag gccaccactt caagaactct gtagcaccgc ctacatacct    3420
cgctctgcta atcctgttac cagtggctgc tgccagtggc gataagtcgt gtcttaccgg    3480
gttggactca agacgatagt taccggataa ggcgcagcgg tcgggctgaa cggggggttc    3540
gtgcacacag cccagcttgg agcgaacgac ctacaccgaa ctgagatacc tacagcgtga    3600
gctatgagaa agcgccacgc ttcccgaagg gagaaaggcg gacaggtatc cggtaagcgg    3660
cagggtcgga acaggagagc gcacgaggga gcttccaggg ggaaacgcct ggtatcttta    3720
tagtcctgtc gggtttcgcc acctctgact tgagcgtcga ttttttgtgat gctcgtcagg   3780 ggggcggagc ctatggaaaa acgccagcaa cgcggccttt ttacggttcc tggccttttg    3840
ctggcctttt gctcacatgt tctttcctgc gttatcccct gattctgtgg ataaccgtat    3900
taccgccatg cat                                                       3913
```

TARGETED THERAPEUTIC PROTEINS

REFERENCE TO RELATED APPLICATIONS

This application claims the benefit of U.S. Ser. No. 60/516,990, filed Nov. 3, 2003, and claims priority to International Application Serial No. PCT/US03/17211, filed May 29, 2003, an international application designating the United States, which claims the benefit of U.S. Ser. No. 60/445,734, filed Feb. 6, 2003; U.S. Ser. No. 10/272,531, filed Oct. 16, 2002; U.S. Ser. No. 60/408,816, filed Sep. 6, 2002; U.S. Ser. No. 60/386,019, filed Jun. 5, 2002; and U.S. Ser. No. 60/384,452, filed May 29, 2002; this application also claims priority to U.S. Ser. No. 10/272,531, filed Oct. 16, 2002, which claims the benefit of U.S. Ser. No. 60/408,816, filed Sep. 6, 2002; U.S. Ser. No. 60/386,019, filed Jun. 5, 2002; and U.S. Ser. No. 60/384,452, filed May 29, 2002, the contents of each of which are incorporated by reference in their entireties. This application is also related to U.S. Ser. No. 60/287,531, filed Apr. 30, 2001; U.S. Ser. No. 60/304,609, filed Jul. 10, 2001; U.S. Ser. No. 60/329,461, filed Oct. 15, 2001; U.S. Ser. No. 60/351,276, filed Jan. 23, 2002; U.S. Ser. No. 10/136,841, filed Apr. 30, 3002; U.S. Ser. No. 10/272,483, filed Oct. 16, 2002, the contents of each of which are incorporated by reference in their entireties.

This invention provides a means for specifically delivering proteins to a targeted subcellular compartment of a mammalian cell. The ability to target proteins to a subcellular compartment is of great utility in the treatment of metabolic diseases such as lysosomal storage diseases, a class of over 40 inherited disorders in which particular lysosomal enzymes are absent or deficient.

BACKGROUND

Enzyme deficiencies in cellular compartments such as the golgi, the endoplasmic reticulum, and the lysosome cause a wide variety of human diseases. For example, lysyl hydroxylase, an enzyme normally in the lumen of the endoplasmic reticulum, is required for proper processing of collagen; absence of the enzyme causes Ehlers-Danlos syndrome type VI, a serious connective tissue disorder. GnT II, normally found in the golgi, is required for normal glycosylation of proteins; absence of GnT II causes leads to defects in brain development. More than forty lysosomal storage diseases (LSDs) are caused, directly or indirectly, by the absence of one or more proteins in the lysosome.

Mammalian lysosomal enzymes are synthesized in the cytosol and traverse the ER where they are glycosylated with N-linked, high mannose type carbohydrate. In the golgi, the high mannose carbohydrate is modified on lysosomal proteins by the addition of mannose-6-phosphate (M6P) which targets these proteins to the lysosome. The M6P-modified proteins are delivered to the lysosome via interaction with either of two M6P receptors. The most favorable form of modification is when two M6Ps are added to a high mannose carbohydrate.

Enzyme replacement therapy for lysosomal storage diseases (LSDs) is being actively pursued. Therapy, except in Gaucher's disease, generally requires that LSD proteins be taken up and delivered to the lysosomes of a variety of cell types in an M6P-dependent fashion. One possible approach involves purifying an LSD protein and modifying it to incorporate a carbohydrate moiety with M6P. This modified material may be taken up by the cells more efficiently than unmodified LSD proteins due to interaction with M6P receptors on the cell surface. However, because of the time and expense required to prepare, purify and modify proteins for use in subcellular targeting, a need for new, simpler, more efficient, and more cost-effective methods for targeting therapeutic agents to a cellular compartment remains.

SUMMARY OF THE INVENTION

The present invention facilitates the treatment of metabolic diseases by providing targeted protein therapeutics that localize to a subcellular compartment of a cell where the therapeutic is needed. The invention simplifies preparation of targeted protein therapeutics by reducing requirements for posttranslational or postsynthesis processing of the protein. For example, a targeted therapeutic of the present invention can be synthesized as a fusion protein including a therapeutic domain and a domain that targets the fusion protein to a correct subcellular compartment. ("Fusion protein," as used herein, refers to a single polypeptide having at least two domains that are not normally present in the same polypeptide. Thus, naturally occurring proteins are not "fusion proteins" as used herein.) Synthesis as a fusion protein permits targeting of the therapeutic domain to a desired subcellular compartment without complications associated with chemical crosslinking of separate therapeutic and targeting domains, for example.

The invention also permits targeting of a therapeutic to a lysosome in an M6P-independent manner. Accordingly, the targeted therapeutic need not be synthesized in a mammalian cell, but can be synthesized chemically or in a bacterium, yeast, protozoan, or other organism regardless of glycosylation pattern, facilitating production of the targeted therapeutic with high yield and comparatively low cost. The targeted therapeutic can be synthesized as a fusion protein, further simplifying production, or can be generated by associating independently-synthesized therapeutic agents and targeting moieties.

The present invention permits lysosomal targeting of therapeutics without the need for M6P addition to high mannose carbohydrate. It is based in part on the observation that one of the 2 M6P receptors also binds other ligands with high affinity. For example, the cation-independent mannose-6-phosphate receptor is also known as the insulin-like growth factor 2 (IGF-II) receptor because it binds IGF-II with high affinity. This low molecular weight polypeptide interacts with three receptors, the insulin receptor, the IGF-I receptor and the M6P/IGF-II receptor. It is believed to exert its biological effect primarily through interactions with the former two receptors while interaction with the cation-independent M6P receptor is believed to result predominantly in the IGF-II being transported to the lysosome where it is degraded.

Accordingly, the invention relates in one aspect to a targeted therapeutic including a targeting moiety and a therapeutic agent that is therapeutically active in a mammalian lysosome. "Therapeutically active," as used herein, encompasses at least polypeptides or other molecules that provide an enzymatic activity to a cell or a compartment thereof that is deficient in that activity. "Therapeutically active" also encompasses other polypeptides or other molecules that are intended to ameliorate or to compensate for a biochemical deficiency in a cell, but does not encompass molecules that are primarily cytotoxic or cytostatic, such as chemotherapeutics.

In one embodiment, the targeting moiety is a means (e.g. a molecule) for binding the extracellular domain of the human cation-independent M6P receptor in an M6P-independent manner when the receptor is present in the plasma membrane of a target cell. In another embodiment, the targeting moiety is an unglycosylated lysosomal targeting domain that binds the extracellular domain of the human cation-independent M6P receptor. In either embodiment, the targeting moiety can include, for example, IGF-II; retinoic acid or a derivative thereof; a protein having an amino acid sequence at least 70% identical to a domain of urokinase-type plasminogen activator receptor; an antibody variable domain that recognizes the receptor; or variants thereof. In some embodiments, the targeting moiety binds to the receptor with a submicromolar dissociation constant (e.g. less than $10^{-8}$ M, less than $10^{-9}$ M, less than $10^{-10}$ M, or between $10^{-7}$ M and $10^{-11}$ M) at or about pH 7.4 and with a dissociation constant at or about pH 5.5 of at least $10^{-6}$ M and at least ten times the dissociation constant at or about pH 7.4. In particular embodiments, the means for binding binds to the extracellular domain at least 10-fold less avidly (i.e. with at least a ten-fold greater dissociation constant) at or about pH 5.5 than at or about pH 7.4; in one embodiment, the dissociation constant at or about pH 5.5 is at least $10^{-6}$ M. In a further embodiment, association of the targeted therapeutic with the means for binding is destabilized by a pH change from at or about pH 7.4 to at or about pH 5.5.

In another embodiment, the targeting moiety is a lysosomal targeting domain that binds the extracellular domain of the human cation-independent M6P receptor but does not bind a mutein of the receptor in which amino acid 1572 is changed from isoleucine to threonine, or binds the mutein with at least ten-fold less affinity (i.e. with at least a ten-fold greater dissociation constant). In another embodiment, the targeting moiety is a lysosomal targeting domain capable of binding a receptor domain consisting essentially of repeats 10-15 of the human cation-independent M6P receptor: the lysosomal targeting domain can bind a protein that includes repeats 10-15 even if the protein includes no other moieties that bind the lysosomal targeting domain. Preferably, the lysosomal targeting domain can bind a receptor domain consisting essentially of repeats 10-13 of the human cation-independent mannose-6-phosphate receptor. More preferably, the lysosomal targeting domain can bind a receptor domain consisting essentially of repeats 11-12, repeat 11, or amino acids 1508-1566 of the human cation-independent M6P receptor. In each of these embodiments, the lysosomal targeting domain preferably binds the receptor or receptor domain with a submicromolar dissociation constant at or about pH 7.4. In one preferred embodiment, the lysosomal targeting domain binds with an dissociation constant of about $10^{-7}$ M. In another preferred embodiment, the dissociation constant is less than about $10^{-7}$ M.

In another embodiment, the targeting moiety is a binding moiety sufficiently duplicative of human IGF-II such that the binding moiety binds the human cation-independent M6P receptor. The binding moiety can be sufficiently duplicative of IGF-II by including an amino acid sequence sufficiently homologous to at least a portion of IGF-II, or by including a molecular structure sufficiently representative of at least a portion of IGF-II, such that the binding moiety binds the cation-independent M6P receptor. The binding moiety can be an organic molecule having a three-dimensional shape representative of at least a portion of IGF-II, such as amino acids 48-55 of human IGF-II, or at least three amino acids selected from the group consisting of amino acids 8, 48, 49, 50, 54, and 55 of human IGF-II. A preferred organic molecule has a hydrophobic moiety at a position representative of amino acid 48 of human IGF-II and a positive charge at or about pH 7.4 at a position representative of amino acid 49 of human IGF-II. In one embodiment, the binding moiety is a polypeptide including a polypeptide having antiparallel alpha-helices separated by not more than five amino acids. In another embodiment, the binding moiety includes a polypeptide with the amino acid sequence of IGF-I or of a mutein of IGF-I in which amino acids 55-56 are changed and/or amino acids 1-4 are deleted or changed. In a further embodiment, the binding moiety includes a polypeptide with an amino acid sequence at least 60% identical to human IGF-II; amino acids at positions corresponding to positions 54 and 55 of human IGF-II are preferably uncharged or negatively charged at or about pH 7.4.

In one embodiment, the targeting moiety is a polypeptide comprising the amino acid sequence phenylalanine-arginine-serine. In another embodiment, the targeting moiety is a polypeptide including an amino acid sequence at least 75% homologous to amino acids 48-55 of human IGF-II. In another embodiment, the targeting moiety includes, on a single polypeptide or on separate polypeptides, amino acids 8-28 and 41-61 of human IGF-II. In another embodiment, the targeting moiety includes amino acids 41-61 of human IGF-II and a mutein of amino acids 8-28 of human IGF-II differing from the human sequence at amino acids 9, 19, 26, and/or 27.

In some embodiments, the association of the therapeutic agent with the targeting moiety is labile at or about pH 5.5. In a preferred embodiment, association of the targeting moiety with the therapeutic agent is mediated by a protein acceptor (such as imidazole or a derivative thereof such as histidine) having a pKa between 5.5 and 7.4. Preferably, one of the therapeutic agent or the targeting moiety is coupled to a metal, and the other is coupled to a pH-dependent metal binding moiety.

In another aspect, the invention relates to a therapeutic fusion protein including a therapeutic domain and a subcellular targeting domain. The subcellular targeting domain binds to an extracellular domain of a receptor on an exterior surface of a cell. Upon internalization of the receptor, the subcellular targeting domain permits localization of the therapeutic domain to a subcellular compartment such as a lysosome, an endosome, the endoplasmic reticulum (ER), or the golgi complex, where the therapeutic domain is therapeutically active. In one embodiment, the receptor undergoes constitutive endocytosis. In another embodiment, the therapeutic domain has a therapeutic enzymatic activity. The enzymatic activity is preferably one for which a deficiency (in a cell or in a particular compartment of a cell) is associated with a human disease such as a lysosomal storage disease.

In further aspects, the invention relates to nucleic acids encoding therapeutic proteins and to cells (e.g. mammalian cells, insect cells, yeast cells, protozoans, or bacteria) comprising these nucleic acids. The invention also provides methods of producing the proteins by providing these cells with conditions (e.g. in the context of in vitro culture or by maintaining the cells in a mammalian body) permitting expression of the proteins. The proteins can be harvested thereafter (e.g. if produced in vitro) or can be used without an intervening harvesting step (e.g. if produced in vivo in a patient). Thus, the invention also provides methods of treating a patient by administering a therapeutic protein (e.g. by injection, in situ synthesis, or otherwise), by administering a nucleic acid encoding the protein (thereby permitting in vivo protein synthesis), or by administering a cell comprising a nucleic acid encoding the protein. In one embodiment, the method includes synthesizing a targeted therapeutic including a therapeutic agent that is therapeutically active in a mammalian lysosome and a targeting moiety that binds human cation-independent mannose-6-phosphate receptor in a mannose-6-phosphate-independent manner, and administering the targeted therapeutic to a patient. The method can also include identifying the targeting moiety (e.g. by a recombinant display technique such as phage display, bacterial display, or yeast two-hybrid or by screening libraries for requisite binding properties). In another embodiment, the method includes providing (e.g. on a computer) a molecular model defining a three-dimensional shape representative of at least a portion of human IGF-II; identifying a candidate IGF-II analog having a three-dimensional shape representative of at least a portion of IGF-II (e.g. amino acids 48-55), and producing a therapeutic agent that is active in a mammalian lysosome and directly or indirectly bound to the candidate IGF-II analog. The method can also include determining whether the candidate IGF-II analog binds to the human cation-independent M6P receptor.

This invention also provides methods for producing therapeutic proteins that are targeted to lysosomes and/or across the blood-brain barrier and that possess an extended half-life in circulation in a mammal. The methods include producing an underglycosylated therapeutic protein. As used herein, "underglycosylated" refers to a protein in which one or more carbohydrate structures that would normally be present if the protein were produced in a mammalian cell (such as a CHO cell) has been omitted, removed, modified, or masked, thereby extending the half-life of the protein in a mammal. Thus, a protein may be actually underglycosylated due to the absence of one or more carbohydrate structures, or functionally underglycosylated by modification or masking of one or more carbohydrate structures that promote clearance from circulation. For example, a structure could be masked (i) by the addition of one or more additional moieties (e.g. carbohydrate groups, phosphate groups, alkyl groups, etc.) that interfere with recognition of the structure by a mannose or asialoglycoprotein receptor, (ii) by covalent or noncovalent association of the glycoprotein with a binding moiety, such as a lectin or an extracellular portion of a mannose or asialoglycoprotein receptor, that interferes with binding to those receptors in vivo, or (iii) any other modification to the polypeptide or carbohydrate portion of a glycoprotein to reduce its clearance from the blood by masking the presence of all or a portion of the carbohydrate structure.

In one embodiment, the therapeutic protein includes a peptide targeting moiety (e.g. IGF-I, IGF-II, or a portion thereof effective to bind a target receptor) that is produced in a host (e.g. bacteria or yeast) that does not glycosylate proteins as conventional mammalian cells (e.g. Chinese hamster ovary (CHO) cells) do. For example, proteins produced by the host cell may lack terminal mannose, fucose, and/or N-acetylglucosamine residues, which are recognized by the mannose receptor, or may be completely unglycosylated. In another embodiment, the therapeutic protein, which may be produced in mammalian cells or in other hosts, is treated chemically or enzymatically to remove one or more carbohydrate residues (e.g. one or more mannose, fucose, and/or N-acetylglucosamine residues) or to modify or mask one or more carbohydrate residues. Such a modification or masking may reduce binding of the therapeutic protein to the hepatic mannose and/or asialoglycoprotein receptors. In another embodiment, one or more potential glycosylation sites are removed by mutation of the nucleic acid encoding the targeted therapeutic protein, thereby reducing glycosylation of the protein when synthesized in a mammalian cell or other cell that glycosylates proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a depiction of a preferred embodiment of the invention, incorporating a signal peptide sequence, the mature human β-glucuronidase sequence, a bridge of three amino acids, and an IGF-II sequence. The depicted nucleic acid is SEQ ID NO:5, and the encoded protein is SEQ ID NO:6.

FIG. 5 depicts β-glucuronidase (GUS) activity in human mucopolysaccharidosis VII skin fibroblast GM4668 cells exposed to GUS, a GUS-IGF-II fusion protein (GILT-GUS), GILT-GUS with Δ1-7 and Y27L mutations in the portion ($GILT^2$-GUS), or a negative control (DMEM).

FIG. 6 depicts GUS activity in GM4668 cells exposed to GUS (+β-GUS), GUS-GILT (+GILT), GUS-GILT in the presence of excess IGF-II (+GILT+IGF-II), or a negative control (GM4668).

FIG. 7 is an alignment of human IGF-I (SEQ ID NO:7) and IGF-II (SEQ ID NO:8), showing the A, B, C, and D domains.

FIG. 8 depicts GUS in GM4668 cells exposed to GUS, GUS-GILT, GUS-GILT, GUS-GILT with a deletion of the seven amino-terminal residues (GUS-GILT Δ1-7), GUS-GILT in the presence of excess IGF-II, GUS-GILT Δ1-7 in the presence of excess IGF-II, or a negative control (Mock).

FIG. 9A depicts one form of a phosphorylated high mannose carbohydrate structure linked to a glycoprotein via an asparagine residue, and also depicts the structures of mannose and N-acetylglucosamine (GlcNAc). FIG. 9B depicts a portion of the high mannose carbohydrate structure at a higher level of detail, and indicates positions vulnerable to cleavage by periodate treatment. The positions of the sugar residues within the carbohydrate structure are labeled with circled, capital letters A-H; phosphate groups are indicated with a circled capital P.

FIG. 10 depicts SDS-PAGE analysis of GUSΔC18-GILTΔ1-7 (ΔΔN), GUS (HBG), and GUSΔC18-GILTΔ1-7 treated with endoglycosidase F1 (ΔΔN+F1).

FIG. 11 depicts uptake of untagged β-glucuronidase (M6P), GUSΔC18-GILTΔ1-7 (GILT), or GUSΔC18-GILTΔ1-7 treated with endoglycosidase F1 (GILT+F1) in the absence (Enzyme only) of competitor or in the presence of mannose-6-phosphate (+M6P) or IGF-II (+Tag).

FIG. 12 depicts results of an experiment measuring the in vivo half-life of GUSΔC18-GILTΔ1-7, untreated, treated with endoglycosidases F1 and F2 (+F1+F2), or further treated with dithiothreitol (+F1+F2+DTT).

FIG. 13 depicts results of an experiment measuring accumulation of infused untagged β-glucuronidase (M6P), GUSΔC18-GILTΔ1-7 (GILT), or GUSΔC18-GILTΔ1-7 treated with endoglycosidase F1 (GILT+F1) in the liver, spleen, or bone marrow.

FIG. 14 depicts results of an experiment measuring accumulation of infused untagged β-glucuronidase (M6P), GUSΔC18-GILTΔ1-7 (GILT), or GUSΔC18-GILTΔ1-7 treated with endoglycosidase F1 (GILT+F1) in heart, kidney, or lung tissues.

Figure 15:
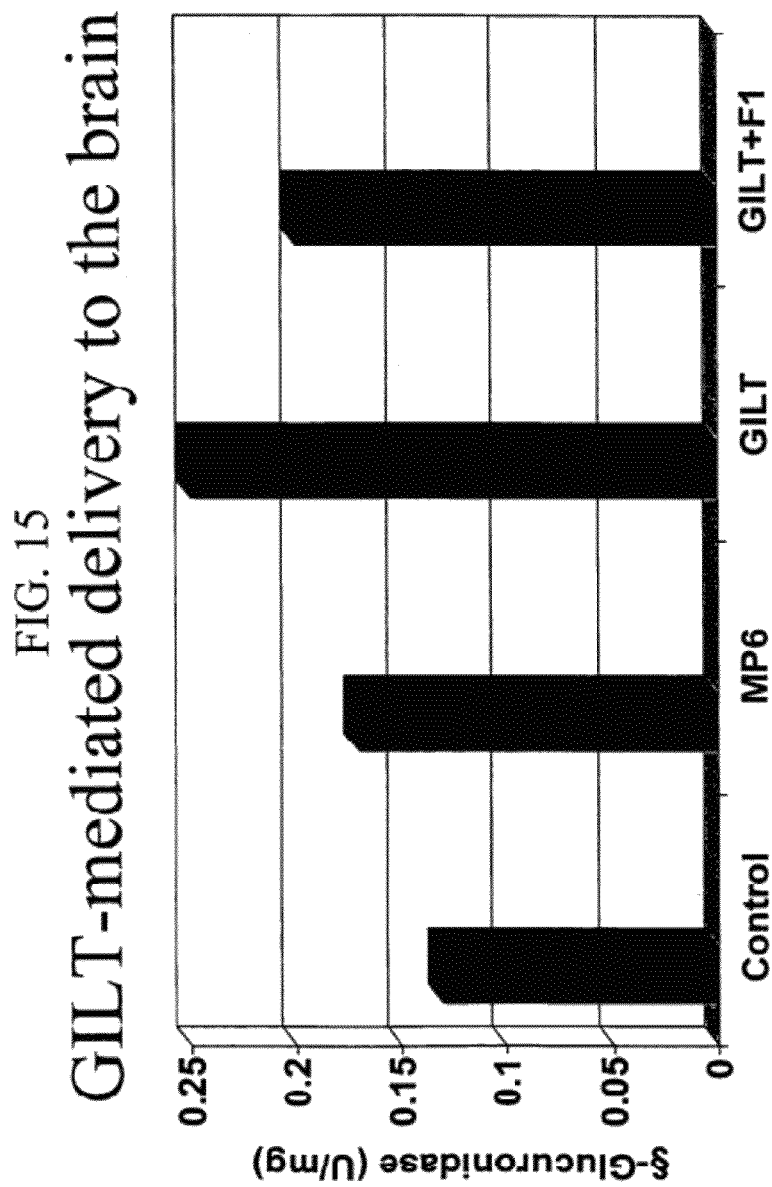

FIG. 15 depicts results of an experiment measuring accumulation of infused untagged β-glucuronidase (M6P), GUSΔC18-GILTΔ1-7 (GILT), or GUSΔC18-GILTΔ1-7 treated with endoglycosidase F1 (GILT+F1) in brain tissue.

Figure 16:
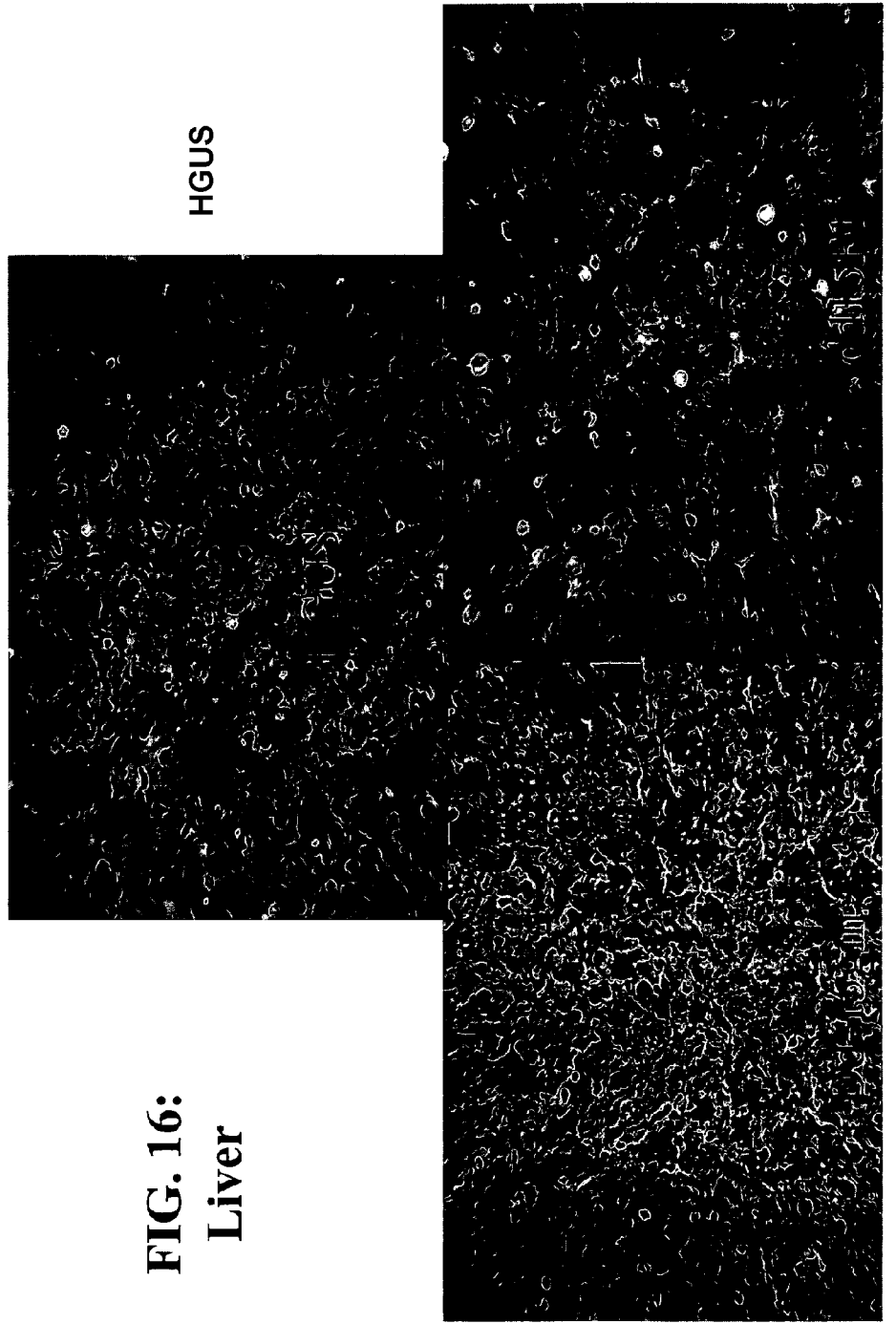

FIG. 16 depicts histological analysis of liver tissue of animals infused with untagged β-glucuronidase (HGUS), GUSΔC18-GILTΔ1-7 (Dd-15gilt), or GUSΔC18-GILTΔ1-7 treated with endoglycosidase F1 (dd15F1).

Figure 17:
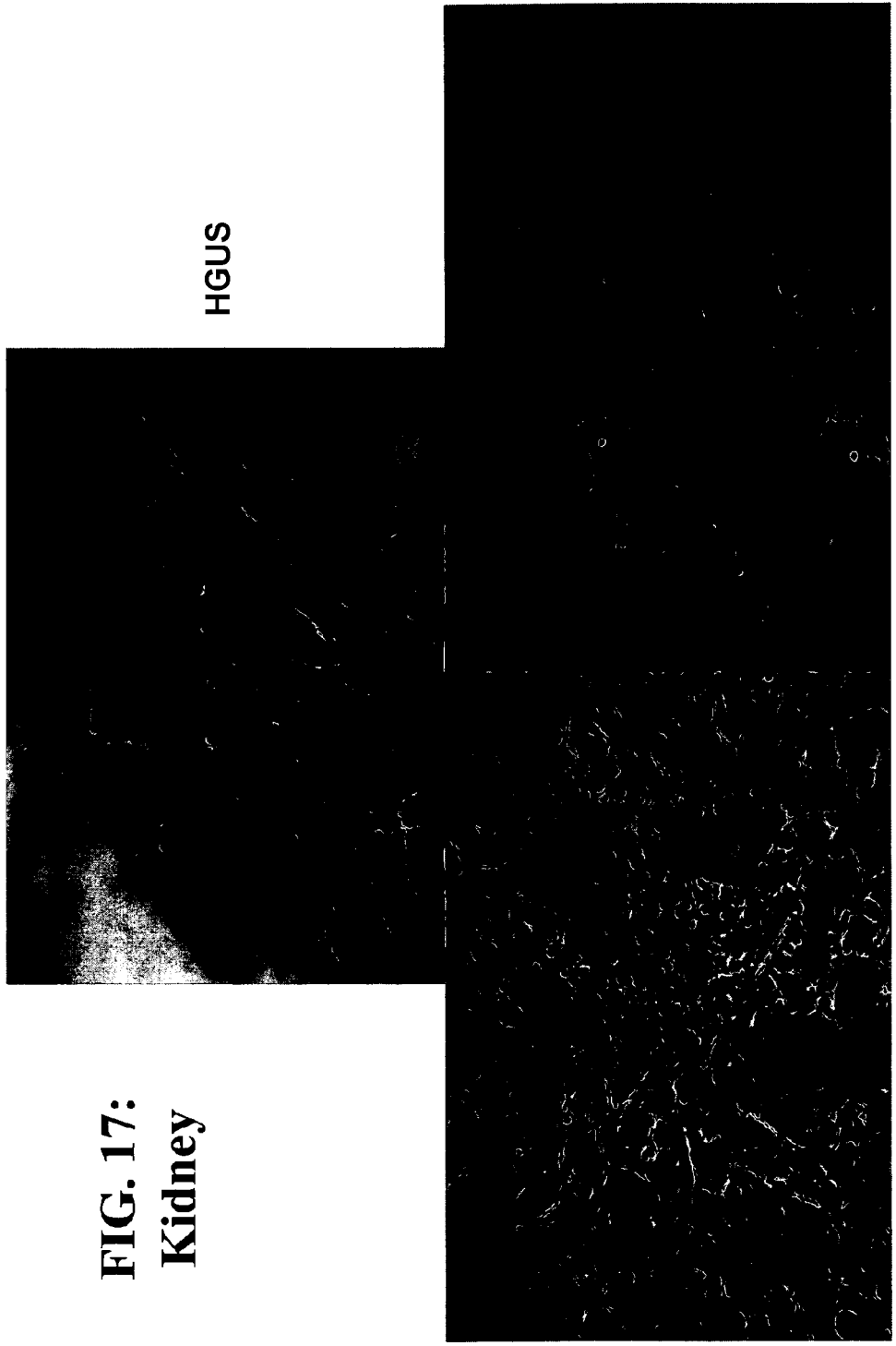

FIG. 17 depicts histological analysis of kidney tissue of animals infused with untagged β-glucuronidase (HGUS), GUSΔC18-GILTΔ1-7 (Dd-15), or GUSΔC18-GILTΔ1-7 treated with endoglycosidase F1 (F1).

Figure 18:
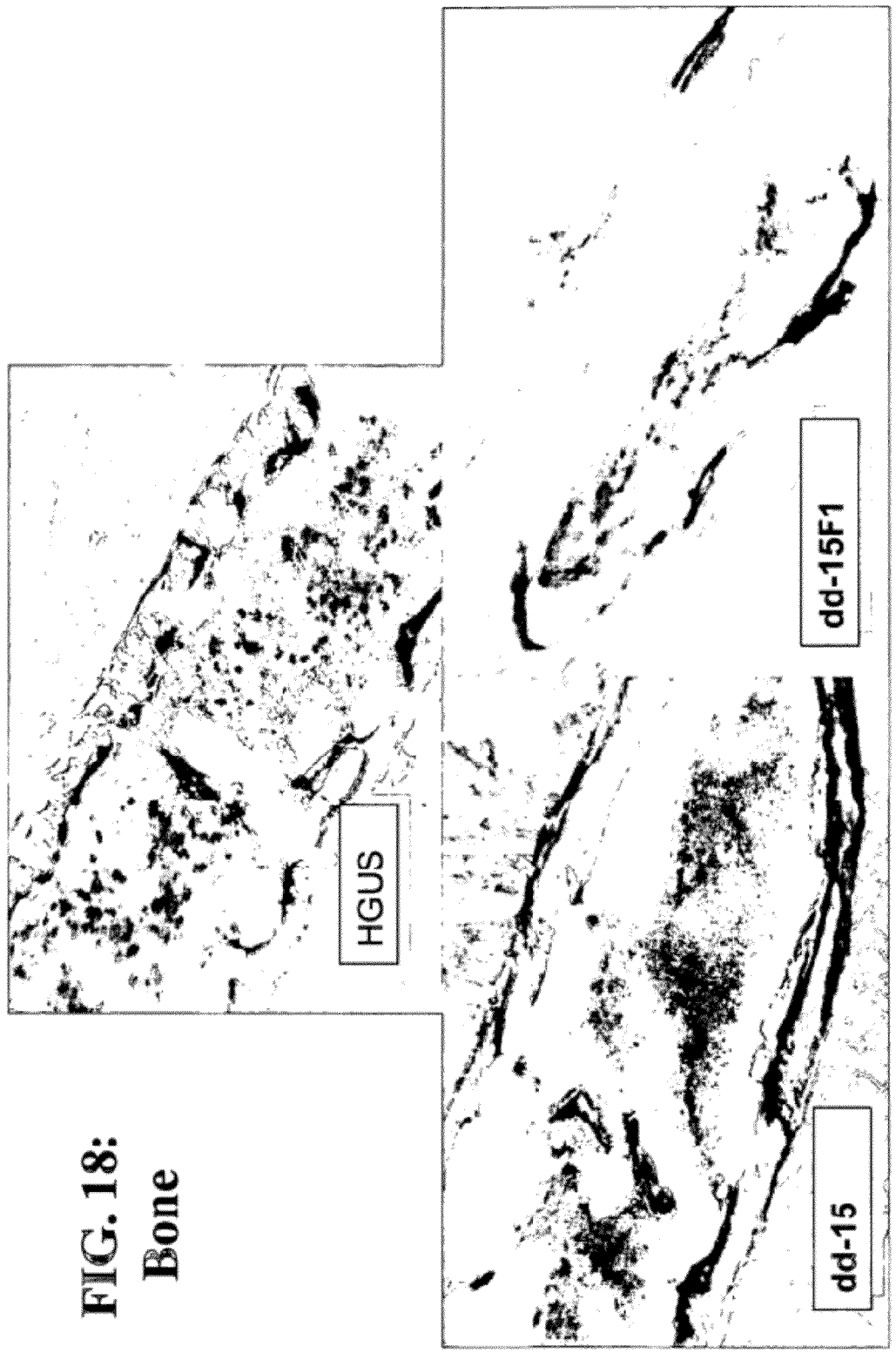

FIG. 18 depicts histological analysis of bone tissue of animals infused with untagged β-glucuronidase (HGUS), GUSΔC18-GILTΔ1-7 (dd-15), or GUSΔC18-GILTΔ1-7 treated with endoglycosidase F1 (dd-15F1).

Figure 19:
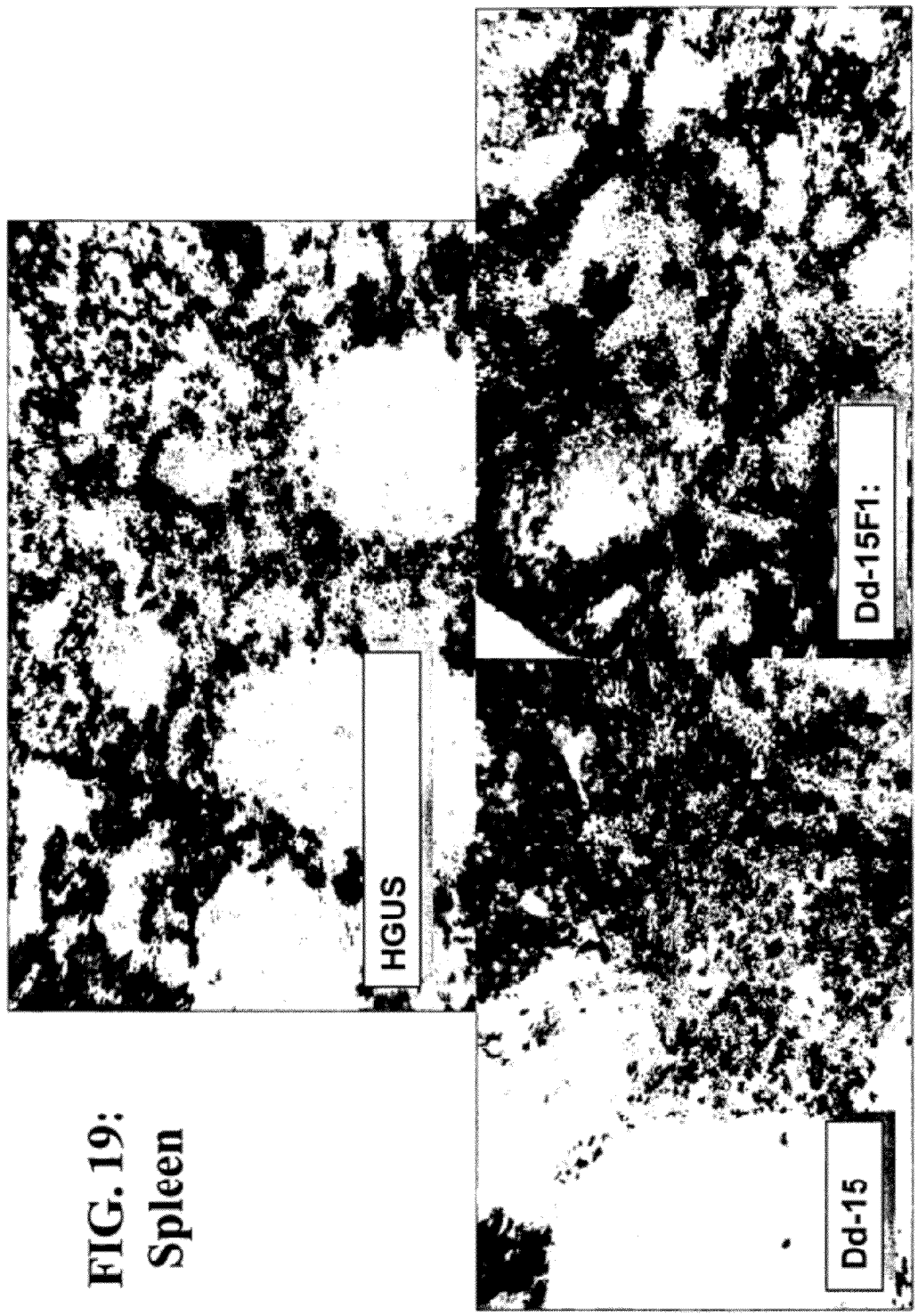

FIG. 19 depicts histological analysis of spleen tissue of animals infused with untagged β-glucuronidase (HGUS), GUSΔC18-GILTΔ1-7 (Dd-15), or GUSΔC18-GILTΔ1-7 treated with endoglycosidase F1 (Dd-15F1:).

Figure 20:
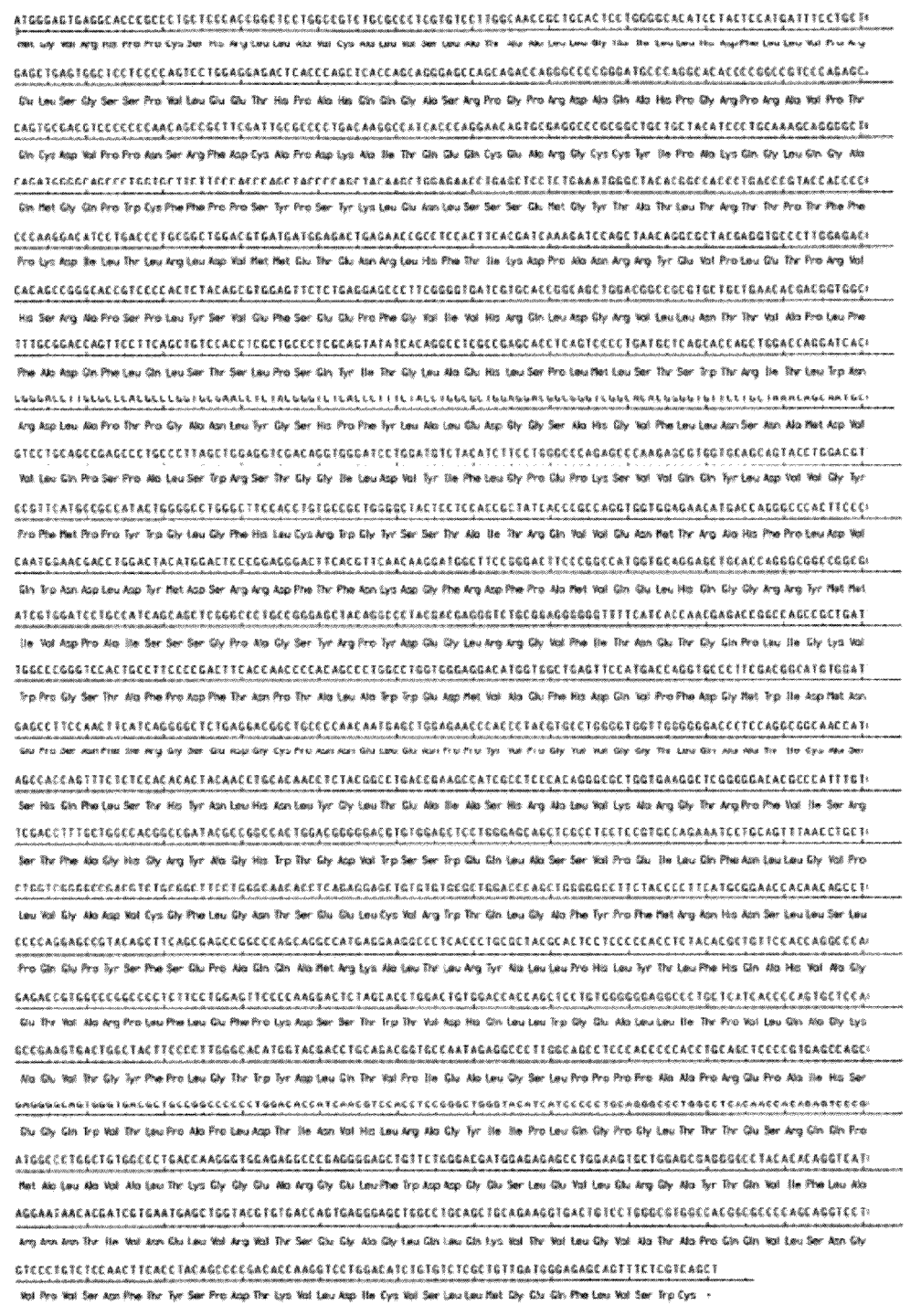

FIG. 20 shows the GAA cDNA sequence (SEQ ID NO:23) of Human Image cDNA clone No. 4374238 and its encoded GAA protein (SEQ ID NO:24).

Figure 21:
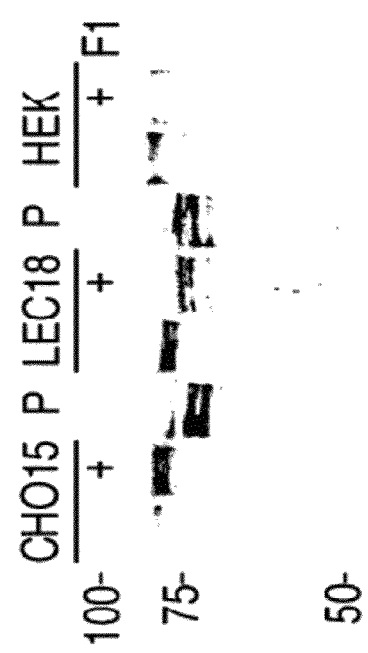

FIG. 21 depicts an SDS-PAGE analysis of GUSΔC18-GILTΔ1-7 produced in CHO cells (CHO15), Lec1 cells (LEC18), or HEK293 cells (HEK) with (+) or without endoglycosidase F1 treatment. Lanes marked "P" denote enzymes treated with PNGase F, which is expected to completely deglycosylate the enzymes.

FIG. 22 depicts the results of a 24 hour GUSΔC18-GILTΔ1-7 accumulation experiment in immunotolerant MPSVII mice using endoglycosidase F1-treated CHO- or Lec1-produced enzymes and untreated HEK293-produced enzyme.

Figure 23:
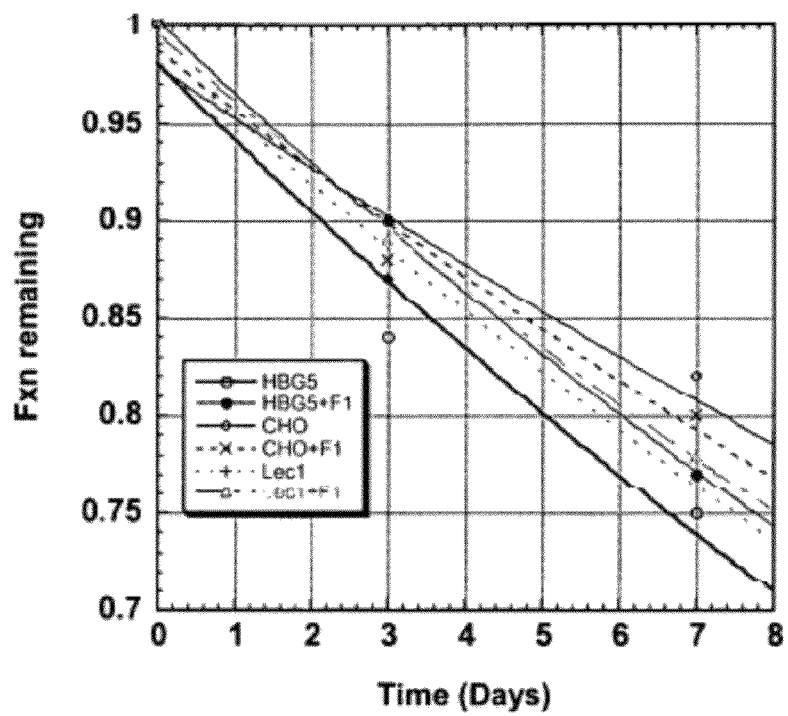

FIG. 23 depicts the results of a half life experiment in human MPSVII fibroblasts using untagged human β-glucuronidase (HBG5), or GUSΔC18-GILTΔ1-7 produced in CHO or Lec1 cells with (+F1) or without endoglycosidase F1 treatment.

Figure 24:
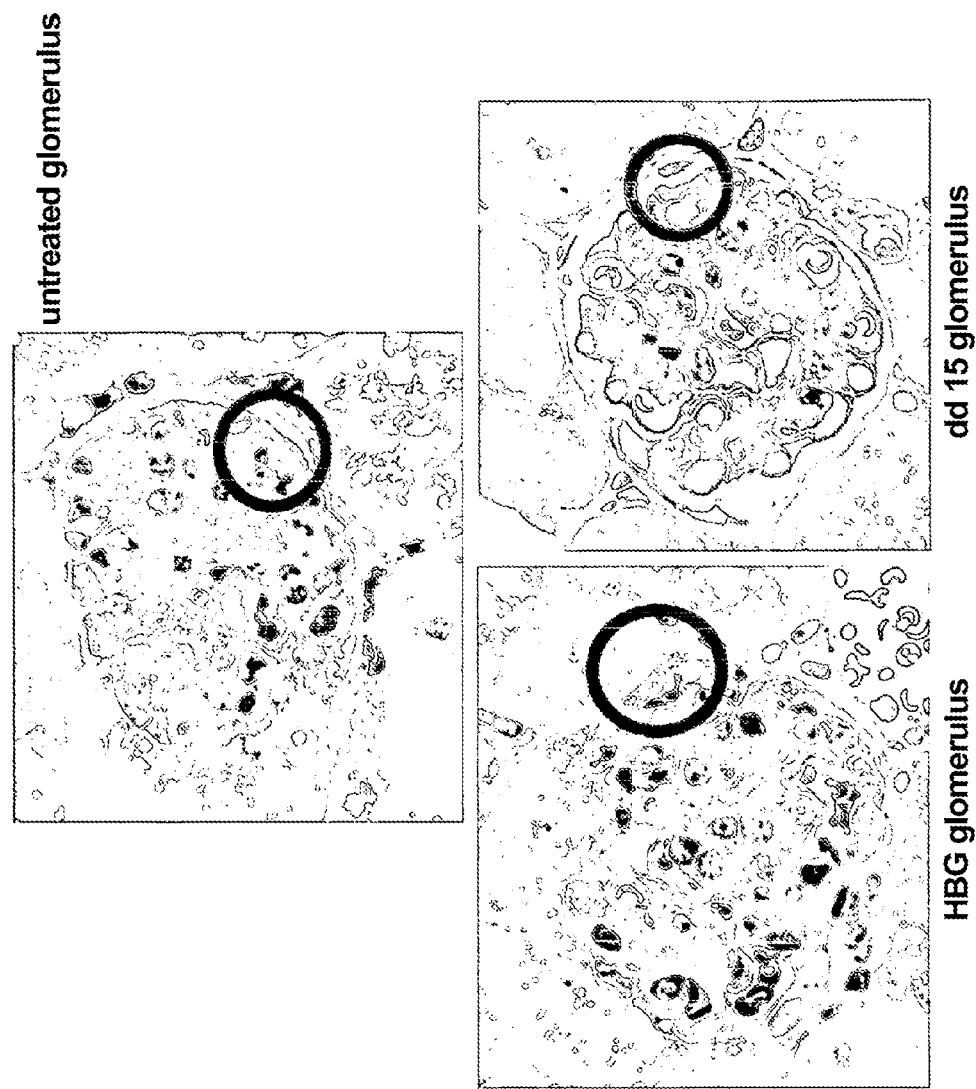

FIG. 24 depicts histological analysis of kidney glomerular epithelial cells (podocytes) from MPS VII mice treated with GUSΔC18-GILTΔ1-7 (dd 15), untagged human β-glucuronidase (HBG), or no enzyme.

Figure 25:
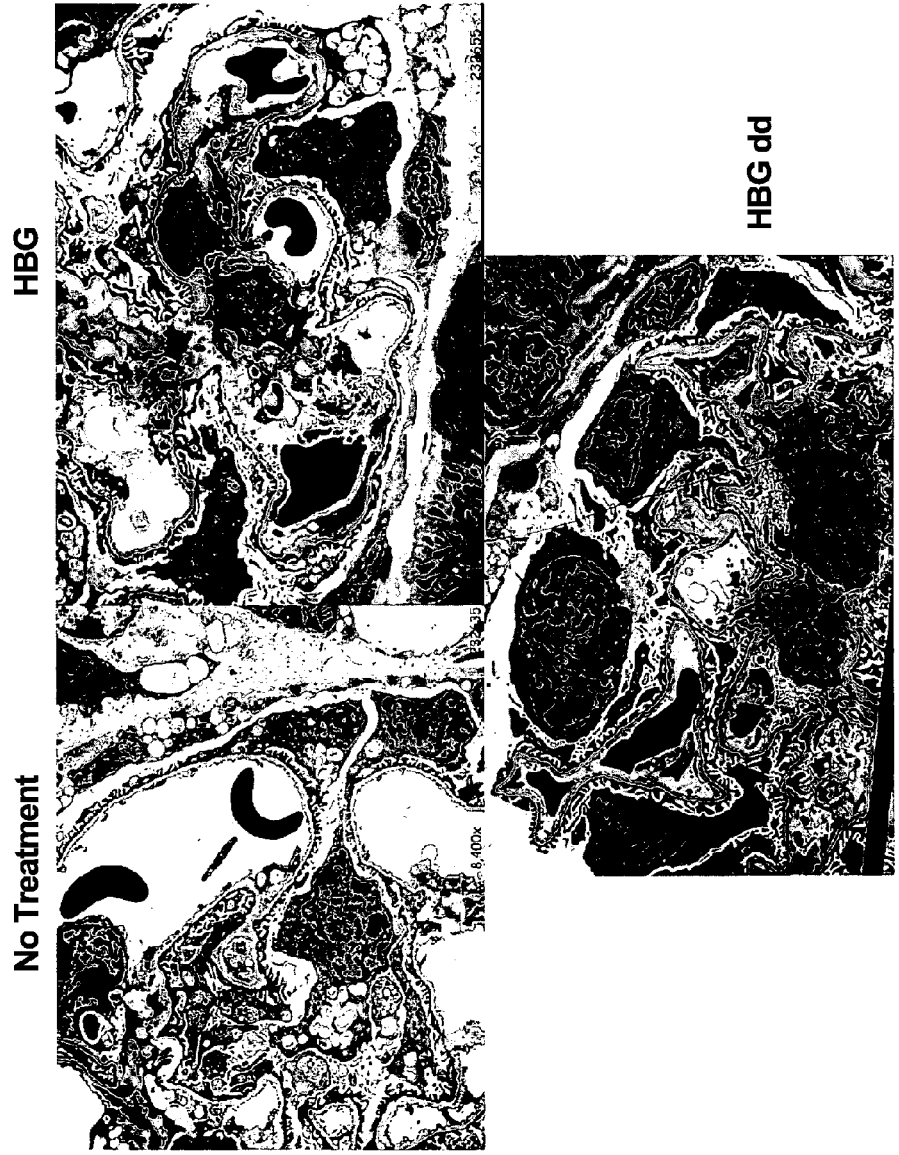

FIG. 25 depicts electron microscope images of kidney glomerular epithelial cells (podocytes) from MPS VII mice treated with GUSΔC18-GILTΔ1-7 (HBG dd), untagged human β-glucuronidase (HBG), or no enzyme.

Figure 26:
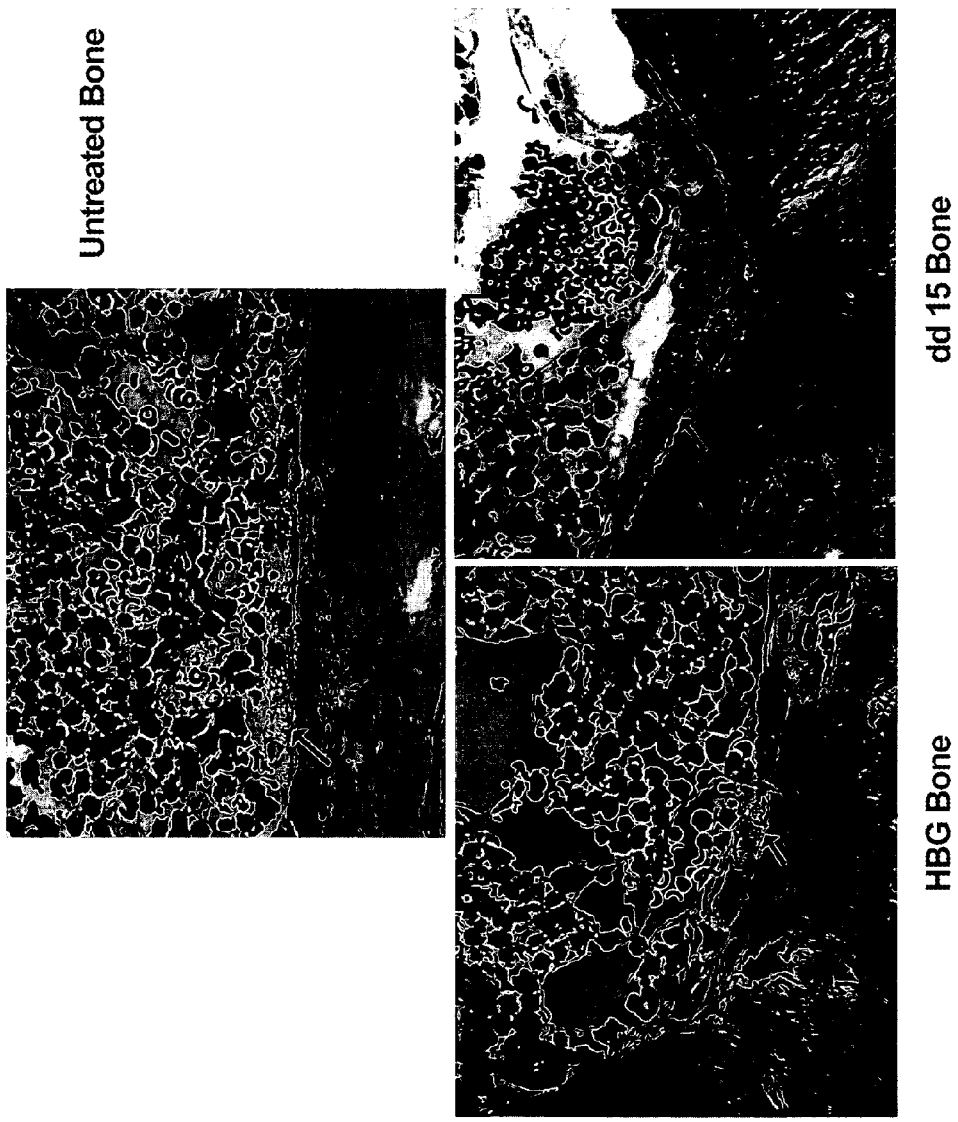

FIG. 26 depicts histological analysis of osteoblasts lining the bone from MPS VII mice treated with GUSΔC18-GILTΔ1-7 (dd 15), untagged human β-glucuronidase (HBG), or no enzyme.

FIG. 27 depicts an exemplary GILT-tagged α-GAL A cassette sequence (SEQ ID NO:25) with a targeting portion fused to the C-terminus of α-GAL A.

FIG. 28 depicts an exemplary unmodified α-GAL A cassette sequence (SEQ ID NO:26).

FIG. 29 depicts the sequence of pISSWA vector (SEQ ID NO:27).

Figure 30:
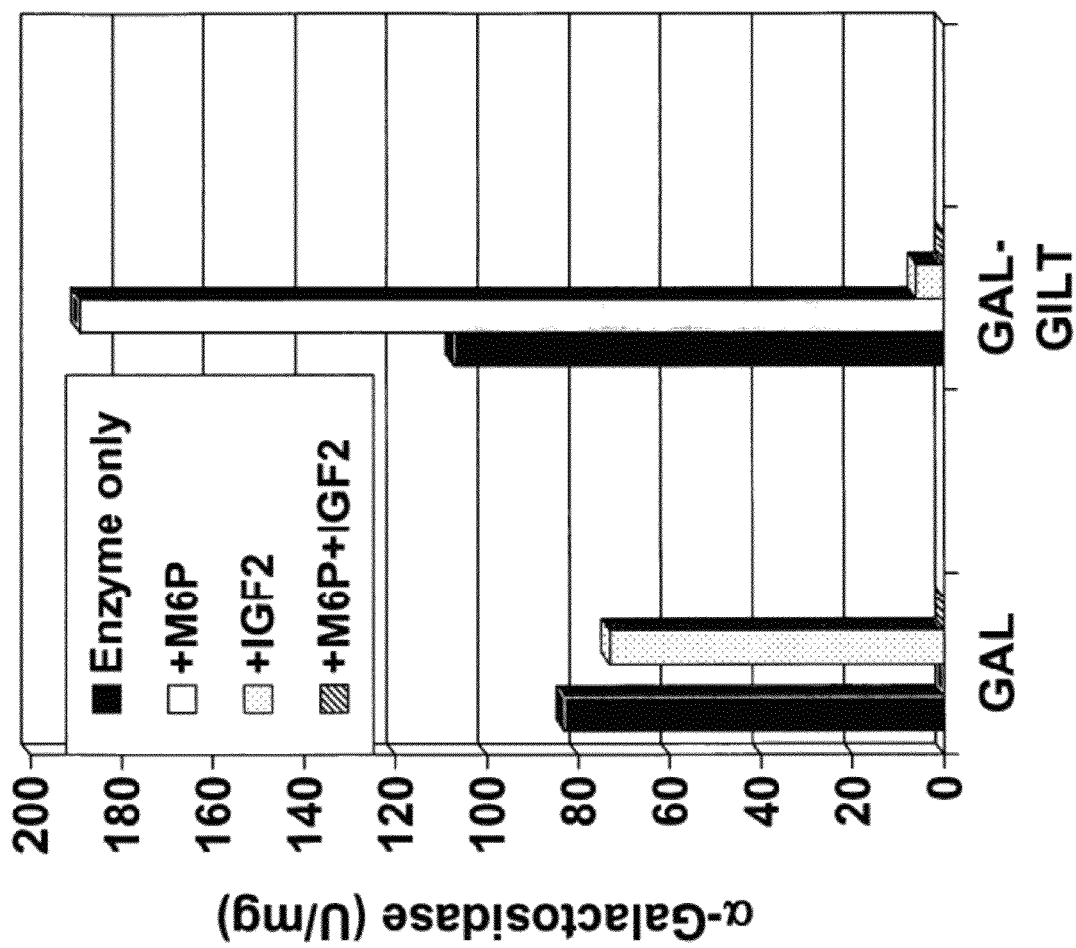

FIG. 30 depicts exemplary results of uptake experiments in α-GAL A-deficient fibroblasts.

DETAILED DESCRIPTION OF THE INVENTION

As used herein and except where otherwise specified, "glycosylation independent lysosomal targeting" and "GILT" refer to lysosomal targeting that is mannose-6-phosphate-independent.

As used herein, "GILT construct" refers to a construct including a mannose-6-phosphate-independent lysosomal targeting portion and a therapeutic portion effective in a mammalian lysosome.

As used herein, "GUS" refers to β-glucuronidase, an exemplary therapeutic portion.

As used herein, "GUSΔC18" refers to GUS with a deletion of the C-terminal 18 amino acids, removing a potential proteolysis site.

As used herein, "GUS-GILT" refers to a GILT construct with GUS coupled to an IGF-II targeting portion.

All references to amino acid positions in IGF-II refer to the positions in mature human IGF-II. Thus, for example, positions 1, 2, and 3 are occupied by alanine, tyrosine, and arginine, respectively.

As used herein, GILTΔ1-7 refers to an IGF-II targeting portion with a deletion of the N-terminal 7 amino acids.

As used herein, GUSΔC18-GILTΔ1-7 refers to a fusion protein in which GUSΔC18 is fused to the N-terminus of GILTΔ1-7.

The present invention facilitates treatment of metabolic diseases by providing targeted therapeutics that, when provided externally to a cell, enter the cell and localize to a subcellular compartment where the targeted therapeutic is active. The targeted therapeutic includes at least a therapeutic agent and a targeting moiety, such as a subcellular targeting domain of a protein, or, for lysosomal targeting, a means (e.g. a protein, peptide, peptide analog, or organic chemical) for binding the human cation-independent mannose-6-phosphate receptor.

Association Between Therapeutic Agent and Targeting Moiety

The therapeutic agent and the targeting moiety are necessarily associated, directly or indirectly. In one embodiment, the therapeutic agent and the targeting moiety are non-covalently associated. The association is preferably stable at or about pH 7.4. For example, the targeting moiety can be biotinylated and bind avidin associated with the therapeutic agent. Alternatively, the targeting moiety and the therapeutic agent can each be associated (e.g. as fusion proteins) with different subunits of a multimeric protein. In another embodiment, the targeting moiety and the therapeutic agent are crosslinked to each other (e.g. using a chemical crosslinking agent).

In a preferred embodiment, the therapeutic agent is fused to the targeting moiety as a fusion protein. The targeting moiety can be at the amino-terminus of the fusion protein, the carboxy-terminus, or can be inserted within the sequence of the therapeutic agent at a position where the presence of the targeting moiety does not unduly interfere with the therapeutic activity of the therapeutic agent.

Where the therapeutic agent is a heteromeric protein, one or more of the subunits can be associated with a targeting portion. Hexosaminidase A, for example, a lysosomal protein affected in Tay-Sachs disease, includes an alpha subunit and a beta subunit. The alpha subunit, the beta subunit, or both can be associated with a targeting moiety in accordance with the present invention. If, for example, the alpha subunit is associated with a targeting moiety and is coexpressed with the beta subunit, an active complex is formed and targeted appropriately (e.g. to the lysosome).

For targeting a therapeutic to the lysosome, the therapeutic agent can be connected to the targeting moiety through an interaction that is disrupted by decreasing the pH from at or about 7.4 to at or about 5.5. The targeting moiety binds a receptor on the exterior of a cell; the selected receptor is one that undergoes endocytosis and passes through the late endosome, which has a pH of about 5.5. Thus, in the late endosome, the therapeutic agent dissociates from the targeting moiety and proceeds to the lysosome, where the therapeutic agent acts. For example, a targeting moiety can be chemically modified to incorporate a chelating agent (e.g. EDTA, EGTA, or trinitrilotriacetic acid) that tightly binds a metal ion such as nickel. The targeting moiety (e.g. GUS) can be expressed as a fusion protein with a six-histidine tag (e.g. at the amino-terminus, at the carboxy-terminus, or in a surface-accessible flexible loop). At or about pH 7.4, the six-histidine tag is substantially deprotonated and binds metal ions such as nickel with high affinity. At or about pH 5.5, the six-histidine tag is substantially protonated, leading to release of the nickel and, consequently, release of the therapeutic agent from the targeting moiety.

Therapeutic Agent

While methods and compositions of the invention are useful for producing and delivering any therapeutic agent to a subcellular compartment, the invention is particularly useful for delivering gene products for treating metabolic diseases.

Preferred LSD genes are shown in Table 1, and preferred genes associated with golgi or ER defects are shown in Table 2. In a preferred embodiment, a wild-type LSD gene product is delivered to a patient suffering from a defect in the same LSD gene. In alternative embodiments, a functional sequence or species variant of the LSD gene is used. In further embodiments, a gene coding for a different enzyme that can rescue an LSD gene defect is used according to methods of the invention.

TABLE 1

Lysosomal Storage Diseases and associated enzyme defects

| Disease Name | Enzyme Defect | Substance Stored |
|---|---|---|
| A. Glycogenosis Disorders ||| 
| Pompe Disease | Acid-al, 4-Glucosidase | Glycogen α 1-4 linked Oligosaccharides |
| B. Glycolipidosis Disorders |||
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A & B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A and B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders |||
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders |||
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders |||
| Mucolipidosis II (I-Cell Disease) | N-Acetylglucosamine-1- Phosphotransferase | Heparan Sulfate |
| Mucolipidosis III (Pseudo-Hurler Polydystrophy) | Same as ML II | |
| F. Lysosomal Membrane Transport Disorders |||
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other |||
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

TABLE 2

Diseases of the golgi and ER

| Disease Name | Gene and Enzyme Defect | Features |
|---|---|---|
| Ehlers-Danlos Syndrome Type VI | PLOD1 lysyl hydroxylase | Defect in lysyl hydroxylation of Collagen; located in ER lumen |
| Type Ia glycogen storage disease | glucose6 phosphatase | Causes excessive accumulation of Glycogen in the liver, kidney, and Intestinal mucosa; enzyme is transmembrane but active site is ER lumen |

TABLE 2-continued

Diseases of the golgi and ER

Congenital Disorders of Glycosylation

| | | |
|---|---|---|
| CDG Ic | ALG6<br>α1,3 glucosyltransferase | Defects in N-glycosylation ER lumen |
| CDG Id | ALG3<br>α1,3 mannosyltransferase | Defects in N-glycosylation ER transmembrane protein |
| CDG IIa | MGAT2<br>N-acetylglucosaminyl-transferase II | Defects in N-glycosylation golgi transmembrane protein |
| CDG IIb | GCS1<br>α1,2-Glucosidase I | Defect in N glycosylation ER membrane bound with lumenal catalytic domain releasable by proteolysis |

One particularly preferred therapeutic agent is glucocerebrosidase, currently manufactured by Genzyme as an effective enzyme replacement therapy for Gaucher's Disease. Currently, the enzyme is prepared with exposed mannose residues, which targets the protein specifically to cells of the macrophage lineage. Although the primary pathology in type 1 Gaucher patients are due to macrophage accumulating glucocerebroside, there can be therapeutic advantage to delivering glucocerebrosidase to other cell types. Targeting glucocerebrosidase to lysosomes using the present invention would target the agent to multiple cell types and can have a therapeutic advantage compared to other preparations.

Another preferred therapeutic agent is acid alpha-glucosidase (GAA), a lysosomal enzyme deficient in Pompe disease (see discussion in Example 13). Pompe disease, also known as acid maltase deficiency (AMD), glycogen storage disease type II (GSDII), glycogenosis type II, or GAA deficiency, is a lysosomal storage disease resulting from insufficient activity of GAA, the enzyme that hydrolyzes the α 1-4 linkage in maltose and other linear oligosaccharides, including the outer branches of glycogen, thereby breaking down excess glycogen in the lysosome (Hirschhorn et al. (2001) in *The Metabolic and Molecular Basis of Inherited Disease*, Scriver, et al., eds. (2001), McGraw-Hill: New York, p. 3389-3420). The diminished enzymatic activity occurs due to a variety of missense and nonsense mutations in the gene encoding GAA. Consequently, glycogen accumulates in the lysosomes of all cells in patients with Pompe disease. In particular, glycogen accumulation is most pronounced in lysosomes of cardiac and skeletal muscle, liver, and other tissues. Accumulated glycogen ultimately impairs muscle function. In the most severe form of Pompe disease death occurs before two years of age due to cardio-respiratory failure.

Presently, there is no approved treatment available to cure or slow the progress of Pompe disease. Enzyme replacement therapy currently in clinical trials requires that administered recombinant GAA be taken up by the cells in muscle and liver tissues and be transported to the lysosomes in those cells. However, recombinant GAA produced in engineered CHO cells and in milk of transgenic rabbits currently used in enzyme replacement therapy contains extremely little M6P (Van Hove et al. (1996) *Proc Natl Acad Sci USA*, 93(1):65-70; and U.S. Pat. No. 6,537,785). Therefore, M6P-dependent delivery of recombinant GAA to lysosomes is not efficient, requiring high dosages and frequent infusions. The present invention, in contrast, permits M6P-independent targeting of GAA to patient lysosomes, as described in greater detail in Example 13.

Subcellular Targeting Domains

The present invention permits targeting of a therapeutic agent to a lysosome using a protein, or an analog of a protein, that specifically binds a cellular receptor for that protein. The exterior of the cell surface is topologically equivalent to endosomal, lysosomal, golgi, and endoplasmic reticulum compartments. Thus, endocytosis of a molecule through interaction with an appropriate receptor(s) permits transport of the molecule to any of these compartments without crossing a membrane. Should a genetic deficiency result in a deficit of a particular enzyme activity in any of these compartments, delivery of a therapeutic protein can be achieved by tagging it with a ligand for the appropriate receptor(s).

Multiple pathways directing receptor-bound proteins from the plasma membrane to the golgi and/or endoplasmic reticulum have been characterized. Thus, by using a targeting portion from, for example, SV40, cholera toxin, or the plant toxin ricin, each of which coopt one or more of these subcellular trafficking pathways, a therapeutic can be targeted to the desired location within the cell. In each case, uptake is initiated by binding of the material to the exterior of the cell. For example, SV40 binds to MHC class I receptors, cholera toxin binds to GM1 ganglioside molecules and ricin binds to glycolipids and glycoproteins with terminal galactose on the surface of cells. Following this initial step the molecules reach the ER by a variety of pathways. For example, SV40 undergoes caveolar endocytosis and reaches the ER in a two step process that bypasses the golgi whereas cholera toxin undergoes caveolar endocytosis but traverses the golgi before reaching the ER.

If a targeting moiety related to cholera toxin or ricin is used, it is important that the toxicity of cholera toxin or ricin be avoided. Both cholera toxin and ricin are heteromeric proteins, and the cell surface binding domain and the catalytic activities responsible for toxicity reside on separate polypeptides. Thus, a targeting moiety can be constructed that includes the receptor-binding polypeptide, but not the polypeptide responsible for toxicity. For example, in the case of ricin, the B subunit possesses the galactose binding activity responsible for internalization of the protein, and can be fused to a therapeutic protein. If the further presence of the A subunit improves subcellular localization, a mutant version (mutein) of the A chain that is properly folded but catalytically inert can be provided with the B subunit-therapeutic agent fusion protein.

Proteins delivered to the golgi can be transported to the endoplasmic reticulum (ER) via the KDEL receptor, which retrieves ER-targeted proteins that have escaped to the golgi. Thus, inclusion of a KDEL motif at the terminus of a targeting domain that directs a therapeutic protein to the golgi permits subsequent localization to the ER. For example, a targeting moiety (e.g. an antibody, or a peptide identified by high-throughput screening such as phage display, yeast two hybrid, chip-based assays, and solution-based assays) that binds the cation-independent M6P receptor both at or about pH 7.4 and at or about pH 5.5 permits targeting of a therapeutic agent to the golgi; further addition of a KDEL motif permits targeting to the ER.

Lysosomal Targeting Moieties

The invention permits targeting of a therapeutic agent to a lysosome. Targeting may occur, for example, through binding of a plasma membrane receptor that later passes through a lysosome. Alternatively, targeting may occur through binding of a plasma receptor that later passes through a late endosome; the therapeutic agent can then travel from the late endosome to a lysosome. A preferred lysosomal targeting mechanism involves binding to the cation-independent M6P receptor.

Cation-Independent M6P Receptor

The cation-independent M6P receptor is a 275 kDa single chain transmembrane glycoprotein expressed ubiquitously in mammalian tissues. It is one of two mammalian receptors that bind M6P: the second is referred to as the cation-dependent M6P receptor. The cation-dependent M6P receptor requires divalent cations for M6P binding; the cation-independent M6P receptor does not. These receptors play an important role in the trafficking of lysosomal enzymes through recognition of the M6P moiety on high mannose carbohydrate on lysosomal enzymes. The extracellular domain of the cation-independent M6P receptor contains 15 homologous domains ("repeats") that bind a diverse group of ligands at discrete locations on the receptor.

The cation-independent M6P receptor contains two binding sites for M6P: one located in repeats 1-3 and the other located in repeats 7-9. The receptor binds monovalent M6P ligands with a dissociation constant in the μM range while binding divalent M6P ligands with a dissociation constant in the nM range, probably due to receptor oligomerization. Uptake of IGF-II by the receptor is enhanced by concomitant binding of multivalent M6P ligands such as lysosomal enzymes to the receptor.

The cation-independent M6P receptor also contains binding sites for at least three distinct ligands that can be used as targeting moieties. The cation-independent M6P receptor binds IGF-II with a dissociation constant of about 14 nM at or about pH 7.4, primarily through interactions with repeat 11. Consistent with its function in targeting IGF-II to the lysosome, the dissociation constant is increased approximately 100-fold at or about pH 5.5 promoting dissociation of IGF-II in acidic late endosomes. The receptor is capable of binding high molecular weight O-glycosylated IGF-II forms.

An additional useful ligand for the cation-independent M6P receptor is retinoic acid. Retinoic acid binds to the receptor with a dissociation constant of 2.5 nM. Affinity photolabeling of the cation-independent M6P receptor with retinoic acid does not interfere with IGF-II or M6P binding to the receptor, indicating that retinoic acid binds to a distinct site on the receptor. Binding of retinoic acid to the receptor alters the intracellular distribution of the receptor with a greater accumulation of the receptor in cytoplasmic vesicles and also enhances uptake of M6P modified β-glucuronidase. Retinoic acid has a photoactivatable moiety that can be used to link it to a therapeutic agent without interfering with its ability to bind to the cation-independent M6P receptor.

The cation-independent M6P receptor also binds the urokinase-type plasminogen receptor (uPAR) with a dissociation constant of 9 μM. uPAR is a GPI-anchored receptor on the surface of most cell types where it functions as an adhesion molecule and in the proteolytic activation of plasminogen and TGF-β. Binding of uPAR to the CI-M6P receptor targets it to the lysosome, thereby modulating its activity. Thus, fusing the extracellular domain of uPAR, or a portion thereof competent to bind the cation-independent M6P receptor, to a therapeutic agent permits targeting of the agent to a lysosome.

IGF-II

In a preferred embodiment, the lysosomal targeting portion is a protein, peptide, or other moiety that binds the cation independent M6P/IGF-II receptor in a mannose-6-phosphate-independent manner. Advantageously, this embodiment mimics the normal biological mechanism for uptake of LSD proteins, yet does so in a manner independent of mannose-6-phosphate.

For example, by fusing DNA encoding the mature IGF-II polypeptide to the 3' end of LSD gene cassettes, fusion proteins are created that can be taken up by a variety of cell types and transported to the lysosome. Alternatively, DNA encoding a precursor IGF-II polypeptide can be fused to the 3' end of an LSD gene cassette; the precursor includes a carboxy-terminal portion that is cleaved in mammalian cells to yield the mature IGF-II polypeptide, but the IGF-II signal peptide is preferably omitted (or moved to the 5' end of the LSD gene cassette). This method has numerous advantages over methods involving glycosylation including simplicity and cost effectiveness, because once the protein is isolated, no further modifications need be made.

IGF-II is preferably targeted specifically to the M6P receptor. Particularly useful are mutations in the IGF-II polypeptide that result in a protein that binds the M6P receptor with high affinity while no longer binding the other two receptors with appreciable affinity. IGF-II can also be modified to minimize binding to serum IGF-binding proteins (Baxter (2000) *Am. J. Physiol Endocrinol Metab.* 278(6):967-76) to avoid sequestration of IGF-II/GILT constructs. A number of studies have localized residues in IGF-1 and IGF-II necessary for binding to IGF-binding proteins. Constructs with mutations at these residues can be screened for retention of high affinity binding to the M6P/IGF-II receptor and for reduced affinity for IGF-binding proteins. For example, replacing PHE 26 of IGF-II with SER is reported to reduce affinity of IGF-II for IGFBP-1 and -6 with no effect on binding to the M6P/IGF-II receptor (Bach et al. (1993) *J. Biol. Chem.* 268(13):9246-54). Other substitutions, such as SER for PHE 19 and LYS for GLU 9, can also be advantageous. The analogous mutations, separately or in combination, in a region of IGF-I that is highly conserved with IGF-II result in large decreases in IGF-BP binding (Magee et al. (1999) *Biochemistry* 38(48):15863-70).

An alternate approach is to identify minimal regions of IGF-II that can bind with high affinity to the M6P/IGF-II receptor. The residues that have been implicated in IGF-II binding to the M6P/IGF-II receptor mostly cluster on one face of IGF-II (Terasawa et al. (1994) *EMBO J.* 13(23):5590-7). Although IGF-II tertiary structure is normally maintained by three intramolecular disulfide bonds, a peptide incorporating the amino acid sequence on the M6P/IGF-II receptor binding surface of IGF-II can be designed to fold properly and have binding activity. Such a minimal binding peptide is a highly preferred targeting portion. Designed peptides based on the region around amino acids 48-55 can be tested for binding to the M6P/IGF-II receptor. Alternatively, a random library of peptides can be screened for the ability to bind the M6P/IGF-II receptor either via a yeast two hybrid assay, or via a phage display type assay.

Blood-Brain Barrier

One challenge in therapy for lysosomal storage diseases is that many of these diseases have significant neurological involvement. Therapeutic enzymes administered into the blood stream generally do not cross the blood-brain barrier and therefore cannot relieve neurological symptoms associated with the diseases. IGF-II, however, has been reported to promote transport across the blood-brain barrier via transcytosis (Bickel et al. (2001) *Adv. Drug Deliv. Rev.* 46(1-3):247-79). Thus, appropriately designed GILT constructs should be capable of crossing the blood-brain barrier, affording for the first time a means of treating neurological symptoms associated with lysosomal storage diseases. The constructs can be tested using GUS minus mice as described in Example 14. Further details regarding design, construction and testing of targeted therapeutics that can reach neuronal tissue from blood are disclosed in U.S. Ser. No. 60/329,650, filed Oct. 16, 2001, and in U.S. Ser. No. 10/136,639, filed Apr. 30, 2002.

Structure of IGF-II

NMR structures of IGF-II have been solved by two groups (Terasawa et al. (1994) *EMBO J.* 13(23):5590-7; Torres et al. (1995) *J. Mol. Biol.* 248(2):385-401) (see, e.g., Protein Data Bank record 1IGL). The general features of the IGF-II structure are similar to IGF-I and insulin. The A and B domains of correspond to the A and B chains of insulin. Secondary structural features include an alpha helix from residues 11-21 of the B region connected by a reverse turn in residues 22-25 to a short beta strand in residues 26-28. Residues 25-27 appear to form a small antiparallel beta sheet; residues 59-61 and residues 26-28 may also participate in intermolecular beta-sheet formation. In the A domain of IGF-II, alpha helices spanning residues 42-49 and 53-59 are arranged in an antiparallel configuration perpendicular to the B-domain helix. Hydrophobic clusters formed by two of the three disulfide bridges and conserved hydrophobic residues stabilize these secondary structure features. The N and C termini remain poorly defined as is the region between residues 31-40.

IGF-II binds to the IGF-II/M6P and IGF-I receptors with relatively high affinity and binds with lower affinity to the insulin receptor. IGF-II also interacts with a number if serum IGFBPs.

Binding to the IGF-II/M6P Receptor

Substitution of IGF-II residues 48-50 (Phe Arg Ser) with the corresponding residues from insulin, (Thr Ser Ile), or substitution of residues 54-55 (Ala Leu) with the corresponding residues from IGF-I (Arg Arg) result in diminished binding to the IGF-II/M6P receptor but retention of binding to the IGF-I and insulin receptors (Sakano et al. (1991) *J. Biol. Chem.* 266(31):20626-35).

IGF-I and IGF-II share identical sequences and structures in the region of residues 48-50 yet have a 1000-fold difference in affinity for the receptor. The NMR structure reveals a structural difference between IGF-I and IGF-II in the region of IGF-II residues 53-58 (IGF-I residues 54-59): the alpha-helix is better defined in IGF-II than in IGF-I and, unlike IGF-I, there is no bend in the backbone around residues 53 and 54 (Tones et al. (1995) *J. Mol. Biol.* 248(2):385-401). This structural difference correlates with the substitution of Ala 54 and Leu 55 in IGF-II with Arg 55 and Arg 56 in IGF-I. It is possible either that binding to the IGF-II receptor is disrupted directly by the presence of charged residues in this region or that changes in the structure engendered by the charged residues yield the changes in binding for the IGF-II receptor. In any case, substitution of uncharged residues for the two Arg residues in IGF-I resulted in higher affinities for the IGF-II receptor (Cacciari et al. (1987) *Pediatrician* 14(3): 146-53). Thus the presence of positively charged residues in these positions correlates with loss of binding to the IGF-II receptor.

IGF-II binds to repeat 11 of the cation-independent M6P receptor. Indeed, a minireceptor in which only repeat 11 is fused to the transmembrane and cytoplasmic domains of the cation-independent M6P receptor is capable of binding IGF-II (with an affinity approximately one tenth the affinity of the full length receptor) and mediating internalization of IGF-II and its delivery to lysosomes (Grimme et al. (2000) *J. Biol. Chem.* 275(43):33697-33703). The structure of domain 11 of the M6P receptor is known (Protein Data Base entries 1GP0 and 1GP3; Brown et al. (2002) *EMBO J.* 21(5):1054-1062). The putative IGF-II binding site is a hydrophobic pocket believed to interact with hydrophobic amino acids of IGF-II; candidate amino acids of IGF-II include leucine 8, phenylalanine 48, alanine 54, and leucine 55. Although repeat 11 is sufficient for IGF-II binding, constructs including larger portions of the cation-independent M6P receptor (e.g. repeats 10-13, or 1-15) generally bind IGF-II with greater affinity and with increased pH dependence (see, for example, Linnell et al. (2001) *J. Biol. Chem.* 276(26):23986-23991).

Binding to the IGF-I Receptor

Substitution of IGF-II residues Tyr 27 with Leu, Leu 43 with Val or Ser 26 with Phe diminishes the affinity of IGF-II for the IGF-I receptor by 94-, 56-, and 4-fold respectively (Tones et al. (1995) *J. Mol. Biol.* 248(2):385-401). Deletion of residues 1-7 of human IGF-II resulted in a 30-fold decrease in affinity for the human IGF-I receptor and a concomitant 12 fold increase in affinity for the rat IGF-II receptor (Hashimoto et al. (1995) *J. Biol. Chem.* 270(30):18013-8). The NMR structure of IGF-II shows that Thr 7 is located near residues 48 Phe and 50 Ser as well as near the 9 Cys-47 Cys disulfide bridge. It is thought that interaction of Thr 7 with these residues can stabilize the flexible N-terminal hexapeptide required for IGF-I receptor binding (Terasawa et al. (1994) *EMBO J.* 13(23)5590-7). At the same time this interaction can modulate binding to the IGF-II receptor. Truncation of the C-terminus of IGF-II (residues 62-67) also appear to lower the affinity of IGF-II for the IGF-I receptor by 5 fold (Roth et al. (1991) *Biochem. Biophys. Res. Commun.* 181(2):907-14).

Deletion Mutants of IGF-II

The binding surfaces for the IGF-I and cation-independent M6P receptors are on separate faces of IGF-II. Based on structural and mutational data, functional cation-independent M6P binding domains can be constructed that are substantially smaller than human IGF-II. For example, the amino terminal amino acids 1-7 and/or the carboxy terminal residues 62-67 can be deleted or replaced. Additionally, amino acids 29-40 can likely be eliminated or replaced without altering the folding of the remainder of the polypeptide or binding to the cation-independent M6P receptor. Thus, a targeting moiety including amino acids 8-28 and 41-61 can be constructed. These stretches of amino acids could perhaps be joined directly or separated by a linker. Alternatively, amino acids 8-28 and 41-61 can be provided on separate polypeptide chains. Comparable domains of insulin, which is homologous to IGF-II and has a tertiary structure closely related to the structure of IGF-II, have sufficient structural information to permit proper refolding into the appropriate tertiary structure, even when present in separate polypeptide chains (Wang et al. (1991) *Trends Biochem. Sci.* 279-281). Thus, for example, amino acids 8-28, or a conservative substitution variant thereof, could be fused to a therapeutic agent; the resulting fusion protein could be admixed with amino acids 41-61, or a conservative substitution variant thereof, and administered to a patient.

Binding to IGF Binding Proteins

IGF-II and related constructs can be modified to diminish their affinity for IGFBPs, thereby increasing the bioavailability of the tagged proteins.

Substitution of IGF-II residue phenylalanine 26 with serine reduces binding to IGFBPs 1-5 by 5-75 fold (Bach et al. (1993) *J. Biol. Chem.* 268(13):9246-54). Replacement of IGF-II residues 48-50 with threonine-serine-isoleucine reduces binding by more than 100 fold to most of the IGFBPs (Bach et al. (1993) *J. Biol. Chem.* 268(13):9246-54); these residues are, however, also important for binding to the cation-independent mannose-6-phosphate receptor. The Y27L substitution that disrupts binding to the IGF-I receptor interferes with formation of the ternary complex with IGFBP3 and acid labile subunit (Hashimoto et al. (1997) *J. Biol. Chem.* 272(44):27936-42); this ternary complex accounts for most of the IGF-II in the circulation (Yu et al. (1999) *J. Clin. Lab Anal.* 13(4):166-72). Deletion of the first six residues of IGF-II also interferes with IGFBP binding (Luthi et al. (1992) *Eur. J. Biochem.* 205(2):483-90).

Studies on IGF-I interaction with IGFBPs revealed additionally that substitution of serine for phenylalanine 16 did not effect secondary structure but decreased IGFBP binding by between 40 and 300 fold (Magee et al. (1999) *Biochemistry* 38(48):15863-70). Changing glutamate 9 to lysine also resulted in a significant decrease in IGFBP binding. Furthermore, the double mutant lysine 9/serine 16 exhibited the lowest affinity for IGFBPs. Although these mutations have not previously been tested in IGF-II, the conservation of sequence between this region of IGF-I and IGF-II suggests that a similar effect will be observed when the analogous mutations are made in IGF-II (glutamate 12 lysine/phenylalanine 19 serine).

IGF-II Homologs

The amino acid sequence of human IGF-II, or a portion thereof affecting binding to the cation-independent M6P receptor, may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to human IGF-II.

Figure 2B:
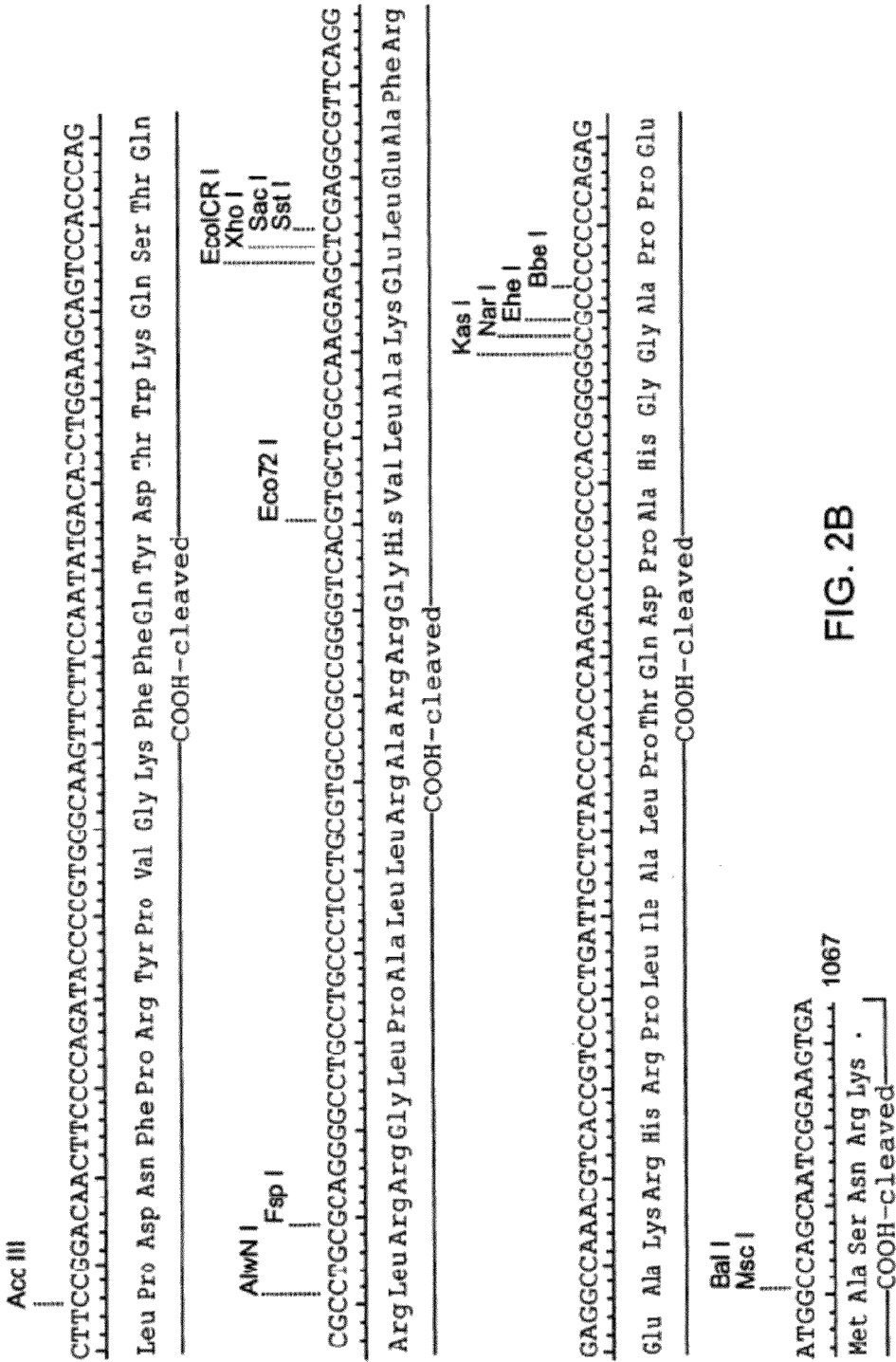
FIG. 2 is a map of the human IGF-II open reading frame (SEQ ID NO:1) and its encoded protein (SEQ ID NO:2). Mature IGF-II lacks the signal peptide and COOH-cleaved regions. The IGF-II signal peptide and the mature polypeptide can be fused to the GAA coding sequence. The IGF-II portion can be modified to incorporated various mutations that enhance the selective binding of IGF-II to the IGF-II receptor.
Figure 3:
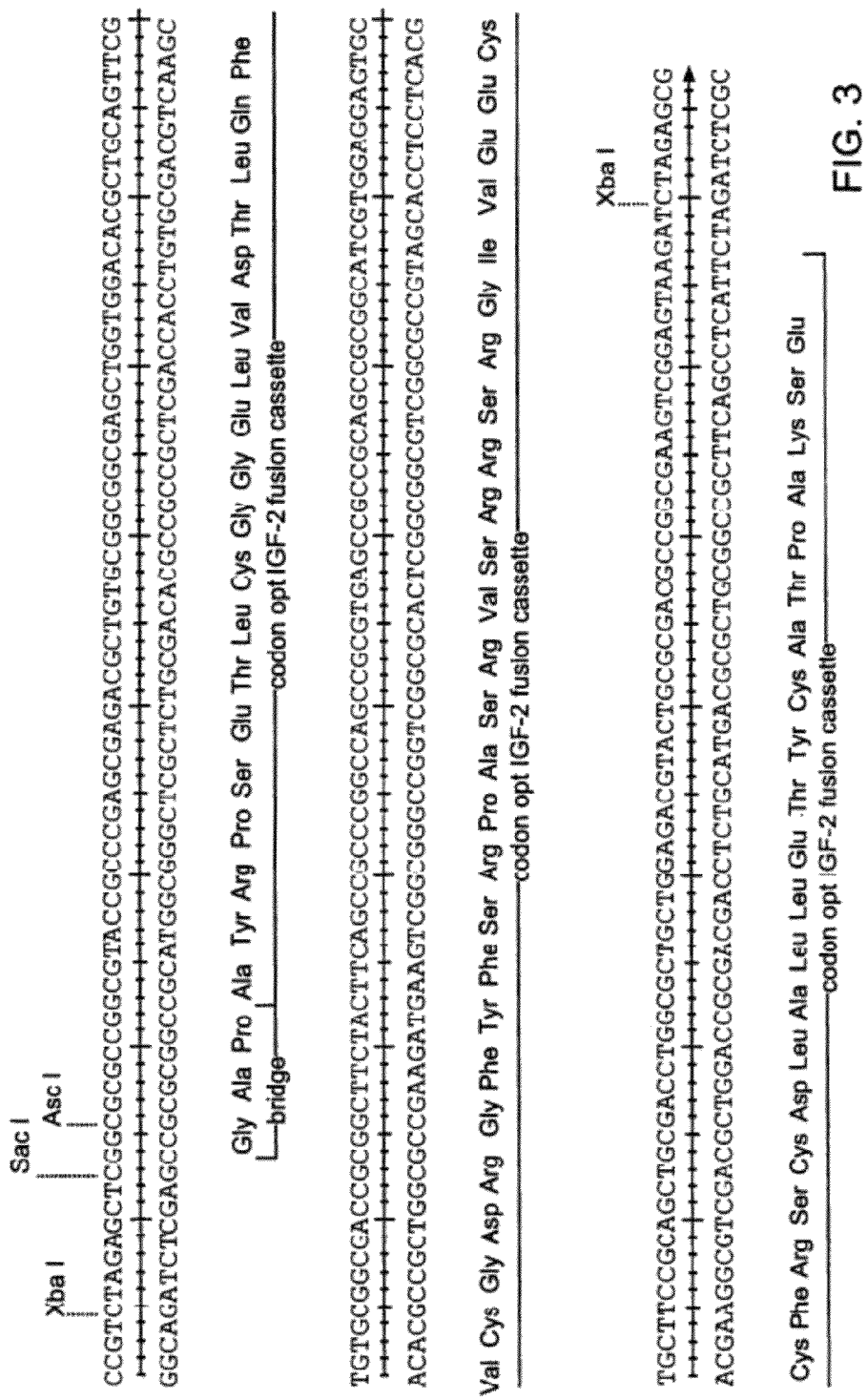
FIG. 3 is a *Leishmania* codon-optimized IGF-II depicted in the XbaI site of pIR1-SAT; the nucleic acid is SEQ ID NO:3 and the encoded protein is SEQ ID NO:4.

To determine whether a candidate peptide region has the requisite percentage similarity or identity to human IGF-II, the candidate amino acid sequence and human IGF-II are first aligned using the dynamic programming algorithm described in Smith and Waterman (1981) *J. Mol. Biol.* 147:195-197, in combination with the BLOSUM62 substitution matrix described in FIG. 2 of Henikoff and Henikoff (1992) *PNAS* 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

IGF-II Structural Analogs

The known structures of human IGF-II and the cation-independent M6P receptors permit the design of IGF-II analogs and other cation-independent M6P receptor binding proteins using computer-assisted design principles such as those discussed in U.S. Pat. Nos. 6,226,603 and 6,273,598. For example, the known atomic coordinates of IGF-II can be provided to a computer equipped with a conventional computer modeling program, such as INSIGHTII, DISCOVER, or DELPHI, commercially available from Biosym, Technologies Inc., or QUANTA, or CHARMM, commercially available from Molecular Simulations, Inc. These and other software programs allow analysis of molecular structures and simulations that predict the effect of molecular changes on structure and on intermolecular interactions. For example, the software can be used to identify modified analogs with the ability to form additional intermolecular hydrogen or ionic bonds, improving the affinity of the analog for the target receptor.

The software also permits the design of peptides and organic molecules with structural and chemical features that mimic the same features displayed on at least part of the surface of the cation-independent M6P receptor binding face of IGF-II. Because a major contribution to the receptor binding surface is the spatial arrangement of chemically interactive moieties present within the sidechains of amino acids which together define the receptor binding surface, a preferred embodiment of the present invention relates to designing and producing a synthetic organic molecule having a framework that carries chemically interactive moieties in a spatial relationship that mimics the spatial relationship of the chemical moieties disposed on the amino acid sidechains which constitute the cation-independent M6P receptor binding face of IGF-II. Preferred chemical moieties, include but are not limited to, the chemical moieties defined by the amino acid side chains of amino acids constituting the cation-independent M6P receptor binding face of IGF-II. It is understood, therefore, that the receptor binding surface of the IGF-II analog need not comprise amino acid residues but the chemical moieties disposed thereon.

For example, upon identification of relevant chemical groups, the skilled artisan using a conventional computer program can design a small molecule having the receptor interactive chemical moieties disposed upon a suitable carrier framework. Useful computer programs are described in, for example, Dixon (1992) Tibtech 10: 357-363; Tschinke et al. (1993) J. Med. Chem. 36: 3863-3870; and Eisen et al. (1994) Proteins: Structure, Function, and Genetics 19: 199-221, the disclosures of which are incorporated herein by reference.

One particular computer program entitled "CAVEAT" searches a database, for example, the Cambridge Structural Database, for structures which have desired spatial orientations of chemical moieties (Bartlett et al. (1989) in "Molecular Recognition: Chemical and Biological Problems" (Roberts, S. M., ed) pp 182-196). The CAVEAT program has been used to design analogs of tendamistat, a 74 residue inhibitor of α-amylase, based on the orientation of selected amino acid side chains in the three-dimensional structure of tendamistat (Bartlett et al. (1989) supra).

Alternatively, upon identification of a series of analogs which mimic the cation-independent M6P receptor binding activity of IGF-II, the skilled artisan may use a variety of computer programs which assist the skilled artisan to develop quantitative structure activity relationships (QSAR) and further to assist in the de novo design of additional morphogen analogs. Other useful computer programs are described in, for example, Connolly-Martin (1991) Methods in Enzymology 203:587-613; Dixon (1992) supra; and Waszkowycz et al. (1994) J. Med. Chem. 37: 3994-4002.

Targeting Moiety Affinities

Preferred targeting moieties bind to their target receptors with a submicromolar dissociation constant. Generally speaking, lower dissociation constants (e.g. less than $10^{-7}$ M, less than $10^{-8}$ M, or less than $10^{-9}$ M) are increasingly preferred. Determination of dissociation constants is preferably determined by surface plasmon resonance as described in Linnell et al. (2001) *J. Biol. Chem.* 276(26):23986-23991. A soluble form of the extracellular domain of the target receptor (e.g. repeats 1-15 of the cation-independent M6P receptor) is generated and immobilized to a chip through an avidin-biotin interaction. The targeting moiety is passed over the chip, and kinetic and equilibrium constants are detected and calculated by measuring changes in mass associated with the chip surface.

Nucleic Acids and Expression Systems

Chimeric fusion proteins can be expressed in a variety of expression systems, including in vitro translation systems and intact cells. Since M6P modification is not a prerequisite for targeting, a variety of expression systems including yeast, baculovirus and even prokaryotic systems such as *E. coli* that do not glycosylate proteins are suitable for expression of targeted therapeutic proteins. In fact, an unglycosylated protein generally has improved bioavailability, since glycosylated proteins are rapidly cleared from the circulation through binding to the mannose receptor in hepatic sinusoidal endothelium.

Alternatively, production of chimeric targeted lysosomal enzymes in mammalian cell expression system produces proteins with multiple binding determinants for the cation-independent M6P receptor. Synergies between two or more cation-independent M6P receptor ligands (e.g. M6P and IGF-II, or M6P and retinoic acid) can be exploited: multivalent ligands have been demonstrated to enhance binding to the receptor by receptor crosslinking.

In general, gene cassettes encoding the chimeric therapeutic protein can be tailored for the particular expression system to incorporate necessary sequences for optimal expression including promoters, ribosomal binding sites, introns, or alterations in coding sequence to optimize codon usage. Because the protein is preferably secreted from the producing cell, a DNA encoding a signal peptide compatible with the expression system can be substituted for the endogenous signal peptide. For example, for expression of β-glucuronidase and α-galactosidase A tagged with IGF-II in *Leishmania*, DNA cassettes encoding *Leishmania* signal peptides (GP63 or SAP) are inserted in place of the DNA encoding the endogenous signal peptide to achieve optimal expression. In mammalian expression systems the endogenous signal peptide may be employed but if the IGF-II tag is fused at the 5' end of the coding sequence, it could be desirable to use the IGF-II signal peptide.

CHO cells are a preferred mammalian host for the production of therapeutic proteins. The classic method for achieving high yield expression from CHO cells is to use a CHO cell line deficient in dihydrofolate reductase (DHFR), for example CHO line DUKX (O'Dell et al. (1998) *Int. J. Biochem. Cell Biol.* 30(7):767-71). This strain of CHO cells requires hypoxanthine and thymidine for growth. Co-transfection of the gene to be overexpressed with a DHFR gene cassette, on separate plasmids or on a single plasmid, permits selection for the DHFR gene and generally allows isolation of clones that also express the recombinant protein of choice. For example, plasmid pcDNA3 uses the cytomegalovirus (CMV) early region regulatory region promoter to drive expression of a gene of interest and pSV2DHFR to promote DHFR expression. Subsequent exposure of cells harboring the recombinant gene cassettes to incrementally increasing concentrations of the folate analog methotrexate leads to amplification of both the gene copy number of the DHFR gene and of the co-transfected gene.

A preferred plasmid for eukaryotic expression in this system contains the gene of interest placed downstream of a strong promoter such as CMV. An intron can be placed in the 3' flank of the gene cassette. A DHFR cassette can be driven by a second promoter from the same plasmid or from a separate plasmid. Additionally, it can be useful to incorporate into the plasmid an additional selectable marker such as neomycin phosphotransferase, which confers resistance to G418.

Another CHO expression system (Ulmasov et al. (2000) *PNAS* 97(26):14212-14217) relies on amplification of the gene of interest using G418 instead of the DHFR/methotrexate system described above. A pCXN vector with a slightly defective neomycin phosphotransferase driven by a weak promoter (see, e.g., Niwa et al. (1991) *Gene* 108:193-200) permits selection for transfectants with a high copy number (>300) in a single step.

Alternatively, recombinant protein can be produced in the human HEK 293 cell line using expression systems based on the Epstein-Barr Virus (EBV) replication system. This consists of the EBV replication origin oriP and the EBV on binding protein, EBNA-1. Binding of EBNA-1 to oriP initiates replication and subsequent amplification of the extrachromosomal plasmid. This amplification in turn results in high levels of expression of gene cassettes housed within the plasmid. Plasmids containing oriP can be transfected into EBNA-1 transformed HEK 293 cells (commercially available from Invitrogen) or, alternatively, a plasmid such as pCEP4 (commercially available from Invitrogen) which drives expression of EBNA-1 and contains the EBV oriP can be employed.

In *E. coli*, the therapeutic proteins are preferably secreted into the periplasmic space. This can be achieved by substituting for the DNA encoding the endogenous signal peptide of the LSD protein a nucleic acid cassette encoding a bacterial signal peptide such as the ompA signal sequence. Expression can be driven by any of a number of strong inducible promoters such as the lac, trp, or tac promoters. One suitable vector is pBAD/gIII (commercially available from Invitrogen) which uses the Gene III signal peptide and the araBAD promoter.

In Vitro Refolding

One useful IGF-II targeting portion has three intramolecular disulfide bonds. GILT fusion proteins (for example GUS-GILT) in *E. coli* can be constructed that direct the protein to the periplasmic space. IGF-II, when fused to the C-terminus of another protein, can be secreted in an active form in the periplasm of *E. coli* (Wadensten et al. (1991) *Biotechnol. Appl. Biochem.* 13(3):412-21). To facilitate optimal folding of the IGF-II moiety, appropriate concentrations of reduced and oxidized glutathione are preferably added to the cellular milieu to promote disulfide bond formation. In the event that a fusion protein with disulfide bonds is incompletely soluble, any insoluble material is preferably treated with a chaotropic agent such as urea to solubilize denatured protein and refolded in a buffer having appropriate concentrations of reduced and oxidized glutathione, or other oxidizing and reducing agents, to facilitate formation of appropriate disulfide bonds (Smith et al. (1989) *J. Biol. Chem.* 264(16):9314-21). For example, IGF-I has been refolded using 6M guanidine-HCl and 0.1 M tris(2-carboxyethyl)phosphine reducing agent for denaturation and reduction of IGF-II (Yang et al. (1999) *J. Biol. Chem.* 274(53):37598-604). Refolding of proteins was accomplished in 0.1M Tris-HCl buffer (pH8.7) containing 1 mM oxidized glutathione, 10 mM reduced glutathione, 0.2M KCl and 1 mM EDTA.

Underglycosylation

Figure 1:
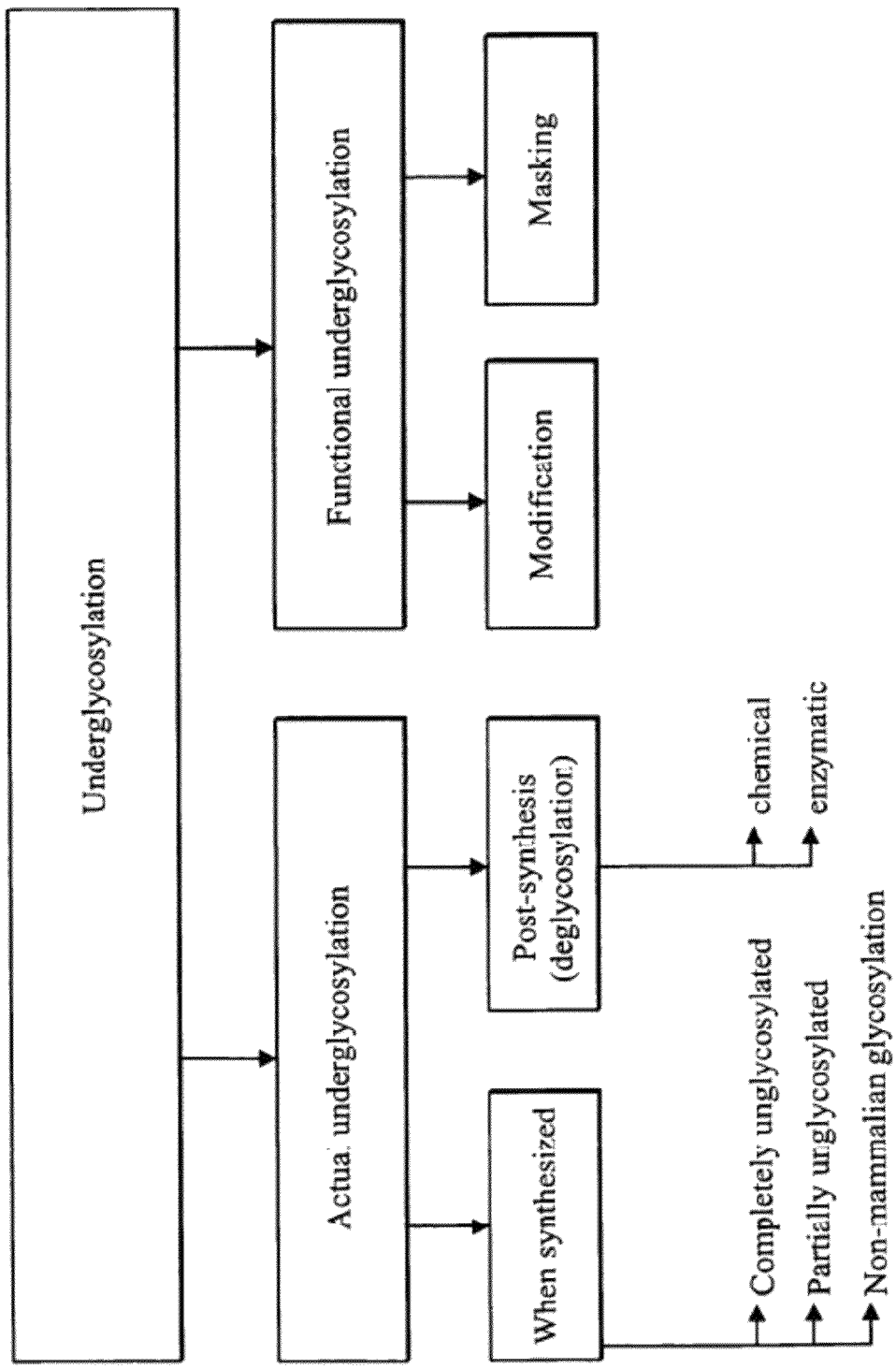
FIG. 1 depicts several types of underglycosylation.

Targeted therapeutic proteins are preferably underglycosylated: one or more carbohydrate structures that would normally be present if the protein were produced in a mammalian cell is preferably omitted, removed, modified, or masked, extending the half-life of the protein in a mammal. Underglycosylation can be achieved in many ways, several of which are diagrammed in FIG. 1. As shown in FIG. 1, a protein may be actually underglycosylated, actually lacking one or more of the carbohydrate structures, or functionally underglycosylated through modification or masking of one or more of the carbohydrate structures. A protein may be actually underglycosylated when synthesized, as discussed in Example 15, and may be completely unglycosylated (as when synthesized in *E. coli*), partially unglycosylated (as when synthesized in a mammalian system after disruption of one or more glycosylation sites by site-directed mutagenesis), or may have a non-mammalian glycosylation pattern. Actual underglycosylation can also be achieved by deglycosylation of a protein after synthesis. As discussed in Example 15, deglycosylation can be through chemical or enzymatic treatments, and may lead to complete deglycosylation or, if only a portion of the carbohydrate structure is removed, partial deglycosylation.

In Vivo Expression

A nucleic acid encoding a therapeutic protein, preferably a secreted therapeutic protein, can be advantageously provided directly to a patient suffering from a disease, or may be provided to a cell ex vivo, followed by administration of the living cell to the patient. In vivo gene therapy methods known in the art include providing purified DNA (e.g. as in a plasmid), providing the DNA in a viral vector, or providing the DNA in a liposome or other vesicle (see, for example, U.S. Pat. No. 5,827,703, disclosing lipid carriers for use in gene therapy, and U.S. Pat. No. 6,281,010, providing adenoviral vectors useful in gene therapy).

Methods for treating disease by implanting a cell that has been modified to express a recombinant protein are also well known. See, for example, U.S. Pat. No. 5,399,346, disclosing methods for introducing a nucleic acid into a primary human cell for introduction into a human. Although use of human cells for ex vivo therapy is preferred in some embodiments, other cells such as bacterial cells may be implanted in a patient's vasculature, continuously releasing a therapeutic agent. See, for example, U.S. Pat. Nos. 4,309,776 and 5,704,910.

Methods of the invention are particularly useful for targeting a protein directly to a subcellular compartment without requiring a purification step. In one embodiment, an IGF-II fusion protein is expressed in a symbiotic or attenuated parasitic organism that is administered to a host. The expressed IGF-II fusion protein is secreted by the organism, taken up by host cells and targeted to their lysosomes.

In some embodiments of the invention, GILT proteins are delivered in situ via live *Leishmania* secreting the proteins into the lysosomes of infected macrophage. From this organelle, it leaves the cell and is taken up by adjacent cells not of the macrophage lineage. Thus, the GILT tag and the therapeutic agent necessarily remain intact while the protein resides in the macrophage lysosome. Accordingly, when GILT proteins are expressed in situ, they are preferably modified to ensure compatibility with the lysosomal environment. Human β-glucuronidase (human "GUS"), an exemplary therapeutic portion, normally undergoes a C-terminal peptide cleavage either in the lysosome or during transport to the lysosome (e.g. between residues 633 and 634 in GUS). Thus, in embodiments where a GUS-GILT construct is to be expressed by *Leishmania* in a macrophage lysosome human GUS is preferably modified to render the protein resistant to cleavage, or the residues following residue 633 are preferably simply omitted from a GILT fusion protein. Similarly, IGF-II, an exemplary targeting portion, is preferably modified to increase its resistance to proteolysis, or a minimal binding peptide (e.g. as identified by phage display or yeast two hybrid) is substituted for the wildtype IGF-II moiety.

Administration

The targeted therapeutics produced according to the present invention can be administered to a mammalian host by any route. Thus, as appropriate, administration can be oral or parenteral, including intravenous and intraperitoneal routes of administration. In addition, administration can be by periodic injections of a bolus of the therapeutic or can be made more continuous by intravenous or intraperitoneal administration from a reservoir which is external (e.g., an i.v. bag). In certain embodiments, the therapeutics of the instant invention can be pharmaceutical-grade. That is, certain embodiments comply with standards of purity and quality control required for administration to humans. Veterinary applications are also within the intended meaning as used herein.

The formulations, both for veterinary and for human medical use, of the therapeutics according to the present invention typically include such therapeutics in association with a pharmaceutically acceptable carrier therefor and optionally other ingredient(s). The carrier(s) can be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified according to the invention and/or known in the art) also can be incorporated into the compositions. The formulations can conveniently be presented in dosage unit form and can be prepared by any of the methods well known in the art of pharmacy/microbiology. In general, some formulations are prepared by bringing the therapeutic into association with a liquid carrier or a finely divided solid carrier or both, and then, if necessary, shaping the product into the desired formulation.

A pharmaceutical targeting composition of the invention is formulated to be compatible with its intended route of administration. Examples of routes of administration include oral or parenteral, e.g., intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Ph can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., 1990.

Formulations for parenteral administration also can include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions that are solid at room temperature and liquid at body temperatures. Formulations also can include, for example, polyalkylene glycols such as polyethylene glycol, oils of vegetable origin, hydrogenated naphthalenes, and the like. Formulations for direct administration can include glycerol and other compositions of high viscosity. Other potentially useful parenteral carriers for these therapeutics include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration can be in the form of discrete units such as capsules, gelatin capsules, sachets, tablets, troches, or lozenges, each containing a predetermined amount of the drug; in the form of a powder or granules; in the form of a solution or a suspension in an aqueous liquid or non-aqueous liquid; or in the form of an oil-in-water emulsion or a water-in-oil emulsion. The therapeutic can also be administered in the form of a bolus, electuary or paste. A tablet can be made by compressing or molding the drug optionally with one or more accessory ingredients. Compressed tablets can be prepared by compressing, in a suitable machine, the drug in a free-flowing form such as a powder or granules, optionally mixed by a binder, lubricant, inert diluent, surface active or dispersing agent. Molded tablets can be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the therapeutic which can be in microcrystalline form, for example, in the form of an aqueous microcrystalline suspension. Liposomal formulations or biodegradable polymer systems can also be used to present the therapeutic for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the therapeutic with a dermatologically acceptable carrier such as a lotion, cream, ointment or soap. In some embodiments, useful are carriers capable of forming a film or layer over the skin to localize application and inhibit removal. Where adhesion to a tissue surface is desired the composition can include the therapeutic dispersed in a fibrinogen-thrombin composition or other bioadhesive. The therapeutic then can be painted, sprayed or otherwise applied to the desired tissue surface. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, such as for asthma, inhalation of powder (self-propelling or spray formulations) dispensed with a spray can, a nebulizer, or an atomizer can be used. Such formulations can be in the form of a finely comminuted powder for pulmonary administration from a powder inhalation device or self-propelling powder-dispensing formulations. In the case of self-propelling solution and spray formulations, the effect can be achieved either by choice of a valve having the desired spray characteristics (i.e., being capable of producing a spray having the desired particle size) or by incorporating the active ingredient as a suspended powder in controlled particle size. For administration by inhalation, the therapeutics also can be delivered in the form of an aerosol spray from a pressured container or dispenser which contains a suitable propellant, e.g., a gas such as carbon dioxide, or a nebulizer. Nasal drops also can be used.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents, bile salts, and filsidic acid derivatives. Transmucosal administration can be accomplished through the use of nasal sprays or suppositories. For transdermal administration, the therapeutics typically are formulated into ointments, salves, gels, or creams as generally known in the art.

In one embodiment, the therapeutics are prepared with carriers that will protect against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Generally, the therapeutics identified according to the invention can be formulated for parenteral or oral administration to humans or other mammals, for example, in therapeutically effective amounts, e.g., amounts which provide appropriate concentrations of the drug to target tissue for a time sufficient to induce the desired effect. Additionally, the therapeutics of the present invention can be administered alone or in combination with other molecules known to have a beneficial effect on the particular disease or indication of interest. By way of example only, useful cofactors include symptom-alleviating cofactors, including antiseptics, antibiotics, antiviral and antifungal agents and analgesics and anesthetics.

The effective concentration of the therapeutics identified according to the invention that is to be delivered in a therapeutic composition will vary depending upon a number of factors, including the final desired dosage of the drug to be administered and the route of administration. The preferred dosage to be administered also is likely to depend on such variables as the type and extent of disease or indication to be treated, the overall health status of the particular patient, the relative biological efficacy of the therapeutic delivered, the formulation of the therapeutic, the presence and types of excipients in the formulation, and the route of administration. In some embodiments, the therapeutics of this invention can be provided to an individual using typical dose units deduced from the earlier-described mammalian studies using non-human primates and rodents. As described above, a dosage unit refers to a unitary, i.e. a single dose which is capable of being administered to a patient, and which can be readily handled and packed, remaining as a physically and biologically stable unit dose comprising either the therapeutic as such or a mixture of it with solid or liquid pharmaceutical diluents or carriers.

In certain embodiments, organisms are engineered to produce the therapeutics identified according to the invention. These organisms can release the therapeutic for harvesting or can be introduced directly to a patient. In another series of embodiments, cells can be utilized to serve as a carrier of the therapeutics identified according to the invention.

Therapeutics of the invention also include the "prodrug" derivatives. The term prodrug refers to a pharmacologically inactive (or partially inactive) derivative of a parent molecule that requires biotransformation, either spontaneous or enzymatic, within the organism to release or activate the active component. Prodrugs are variations or derivatives of the therapeutics of the invention which have groups cleavable under metabolic conditions. Prodrugs become the therapeutics of the invention which are pharmaceutically active in vivo, when they undergo solvolysis under physiological conditions or undergo enzymatic degradation. Prodrug of this invention can be called single, double, triple, and so on, depending on the number of biotransformation steps required to release or activate the active drug component within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Moreover, the prodrug derivatives according to this invention can be combined with other features to enhance bioavailability.

EXAMPLES

Example 1

GILT Constructs

IGF-II cassettes have been synthesized by ligation of a series of overlapping oligos and cloned into Pir1-SAT, a standard *Leishmania* expression vector. 4 IGF-II cassettes have been made: one that encodes the wildtype mature polypeptide, one with a Δ1-7 deletion, one with a Y27L mutation, and one with both mutations. These mutations are reported to reduce binding of IGF-II to the other receptors while not affecting binding to the M6P receptor.

The coding sequence of human IGF-II is shown in FIG. 2. The protein is synthesized as a pre-pro-protein with a 24 amino acid signal peptide at the amino terminus and a 89 amino acid carboxy terminal region both of which are removed post-translationally, reviewed in O'Dell et al. (1998) *Int. J. Biochem Cell Biol.* 30(7):767-71. The mature protein is 67 amino acids. A *Leishmania* codon optimized version of the mature IGF-II is shown in FIG. 3 (Langford et al. (1992) *Exp. Parasitol.* 74(3):360-1). This cassette was constructed by annealing overlapping oligonucleotides whose sequences are shown in Table 3. Additional cassettes containing a deletion of amino acids 1-7 of the mature polypeptide (Δ1-7), alteration of residue 27 from tyrosine to leucine (Y27L) or both mutations (Δ1-7,Y27L) were made to produce IGF-II cassettes with specificity for only the desired receptor as described below. To make the wildtype IGF-II cassette, oligos GILT1-9 were annealed and ligated. To make the Y27L cassette, oligos 1, 12, 3, 4, 5, 16, 7, 8 and 9 were annealed and ligated. After ligation, the two cassettes were column purified. Wildtype and Y27L cassettes were amplified by PCR using oligos GILT 20 and 10 and the appropriate template. To incorporate the Δ1-7 deletion, the two templates were amplified using oligos GILT 11 and 10. The resulting 4 IGF-II cassettes (wildtype, Y27L, Δ1-7, and Y27LΔ1-7) were column purified, digested with XbaI, gel purified and ligated to XbaI cut Pir1-SAT.

Gene cassettes were then cloned between the XmaI site (not shown) upstream of XbaI in the vector and the AscI site in such a way as to preserve the reading frame. An overlapping DAM methylase site at the 3' XbaI site permitted use of the 5' XbaI site instead of the XmaI site for cloning. The AscI site adds a bridge of 3 amino acid residues.

TABLE 3

Oligonucleotides used in the construction of Pir-GILT vectors.

| NAME | SEQ ID NO: | SEQUENCE | POSITION |
|---|---|---|---|
| GILT 1 | 9 | GCGGCGGCGAGCTGGTGGACA CGCTGCAGTTCGTGTGCGGCG ACCGCGGC | 48-97 top strand |
| GILT 2 | 10 | TTCTACTTCAGCCGCCCGGCC AGCCGCGTGAGCCGCCGCAGC CGCGGCAT | 98-147 top strand |
| GILT 3 | 11 | CGTGGAGGAGTGCTGCTTCCG CAGCTGCGACCTGGCGCTGCT GGAGACGT | 148-197 top strand |
| GILT 4 | 12 | ACTGCGCGACGCCGGCGAAGT CGGAGTAAGATCTAGAGCG | 198-237 top strand |
| GILT 5 | 13 | AGCGTGTCCACCAGCTCGCCG CCGCACAGCGTCTCGCTCGGG CGGTACGC | 72-23 bottom |
| GILT 6 | 14 | GGCTGGCCGGGCGGCTGAAGT AGAAGCCGCGGTCGCCGCACA CGAACTGC | 122-73 bottom |
| GILT 7 | 15 | GCTGCGGAAGCAGCACTCCTC CACGATGCCGCGGCTGCGGCG GCTCACGC | 172-123 bottom |
| GILT 8 | 16 | CTCCGACTTCGCCGGCGTCGC GCAGTACGTCTCCAGCAGCGC CAGGTCGCA | 223-173 bottom |
| GILT 9 | 17 | CCGTCTAGAGCTCGGCGCGCC GGCGTACCGCCCGAGCGAGAC GCTGT | 1-47 top strand |
| GILT 10 | 18 | CGCTCTAGATCTTACTCCGAC TTCG | 237-202 bottom |
| GILT 11 | 19 | CCGTCTAGAGCTCGGCGCGCC GCTGTGCGGCGGCGAGCTGGT GGAC | 1-67, Δ23-43 top |

TABLE 3-continued

Oligonucleotides used in the construction of Pir-GILT vectors.

| NAME | SEQ ID NO: | SEQUENCE | POSITION |
|---|---|---|---|
| GILT 12 | 20 | TTCCTGTTCAGCCGCCCGGCC AGCCGCGTGAGCCGCCGCAGC CGCGGCAT | 98-147 (Y27L) top |
| GILT 16 | 21 | GGCTGGCCGGGCGGCTGAACA GGAAGCCGCGGTCGCCGCACA CGAACTGC | 122-73 (Y27L) bot |
| GILT 20 | 22 | CCGTCTAGAGCTCGGCGCGCC GGCG | 1-25 top strand |

Figure 7:
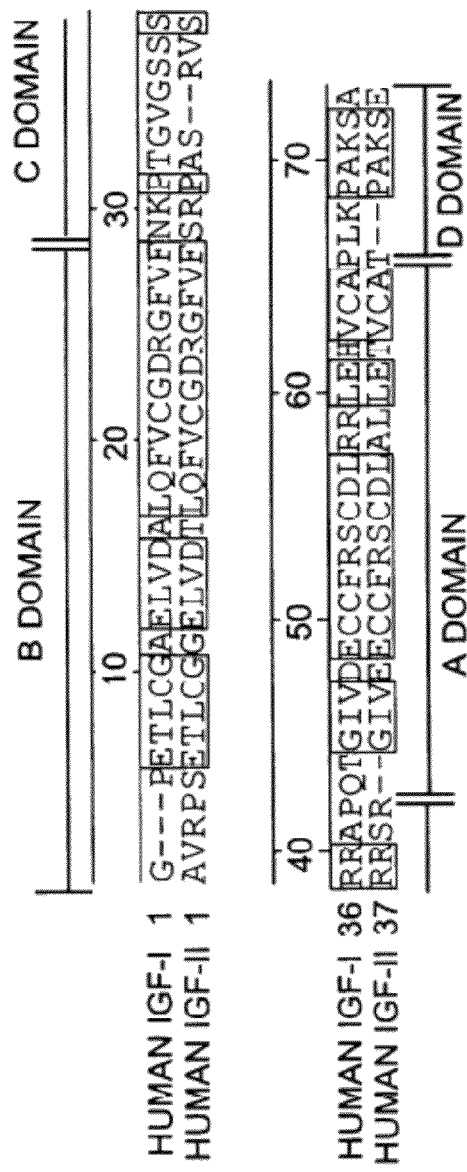

The purpose of incorporating the indicated mutations into the IGF-II cassette is to ensure that the fusion proteins are targeted to the appropriate receptor. Human IGF-II has a high degree of sequence and structural similarity to IGF-I (see, for example, FIG. 7) and the B and A chains of insulin (Terasawa et al. (1994) *EMBO J.* 13(23):5590-7). Consequently, it is not surprising that these hormones have overlapping receptor binding specificities. IGF-II binds to the insulin receptor, the IGF-I receptor and the cation independent mannose 6-phosphate/IGF-II receptor (CIM6P/IGF-II). The CIM6P/IGF-II receptor is a dual activity receptor acting as a receptor for IGF-II and as a mannose 6-phosphate receptor involved in sorting of lysosomal hydrolases. For a number of years, these two activities were attributed to separate proteins until it was determined that both activities resided in a single protein (Morgan et al. (1987) *Nature* 329(6137):301-7; Tong et al. (1988) *J. Biol. Chem.* 263(6):2585-8).

The most profound biological effects of IGF-II, such as its mitogenic effect, are mediated through the IGF-I receptor rather than the CIM6P/IGF-II receptor, reviewed in Ludwig et al. (1995) *Trends in Cell Biology* 5:202-206 (also see Korner et al. (1995) *J. Biol. Chem.* 270(1):287-95). It is thought that the primary result of IGF-II binding to the CIM6P/IGF-II receptor is transport to the lysosome for subsequent degradation. This represents an important means of controlling IGF-II levels and explains why mice carrying null mutants of the CIM6P/IGF-II receptor exhibit perinatal lethality unless IGF-II is also deleted (Lau et al. (1994) *Genes Dev.* 8(24):2953-63; Wang et al. (1994) *Nature* 372(6505):464-7; Ludwig et al. (1996) *Dev. Biol.* 177(2):517-35). In methods of the present invention, it is desirable to have the IGF-II fusion proteins bind to the CIM6P/IGF-II receptor. The Y27L and Δ1-7 mutations reduce binding to the IGF-I and insulin receptors without altering the affinity for the CIM6P/IGF-II receptor (Sakano et al. (1991) *J. Biol. Chem.* 266(31):20626-35; Hashimoto et al. (1995) *J. Biol. Chem.* 270(30):18013-8). Therefore, according to the invention, these mutant forms of IGF-II should provide a means of targeting fusion proteins specifically to the CIM6P/IGF-II receptor.

In one experiment, 4 different IGF-II cassettes with the appropriate sequences, wild type, Δ1-7, Y27L and Δ1-7/Y27L are made. β-GUS cassettes are fused to IGF-II cassettes and these constructs are put into parasites. Alpha-galactosidase cassettes are also fused to the IGF-II cassettes. GUS fusions have been tested and shown to produce enzymatically active protein.

One preferred construct, shown in FIG. 4, includes the signal peptide of the *L. mexicana* secreted acid phosphatase, SAP-1, cloned into the XbaI site of a modified Pir1-SAT in which the single SalI site has been removed. Fused in-frame is the mature β-GUS sequence, connected to an IGF-II tag by a bridge of three amino acids.

Example 2

GILT Protein Preparation

*L. mexicana* expressing and secreting β-GUS were grown at 26° C. in 100 ml Standard Promastigote medium (M199 with 40 mM HEPES, pH 7.5, 0.1 mM adenine, 0.0005% hemin, 0.0001% biotin, 5% fetal bovine serum, 5% embryonic fluid, 50 units/ml penicillin, 50 µg/ml streptomycin and 50 µg/ml nourseothricin). After reaching a density of approximately $5 \times 10^6$ promastigotes/ml, the promastigotes were collected by centrifugation for 10 min. at 1000×g at room temperature; these promastigotes were used to inoculate 1 liter of low protein medium (M199 supplemented with 0.1 mM adenine, 0.0001% biotin, 50 units/ml penicillin and 50 µg/ml streptomycin) at room temperature. The 1 liter cultures were contained in 2 liter capped flasks with a sterile stir bar so that the cultures could be incubated at 26° C. with gentle stirring. The 1 liter cultures were aerated twice a day by moving them into a laminar flow hood, removing the caps and swirling vigorously before replacing the caps. When the cultures reached a density of $2-3 \times 10^7$ promastigotes/ml, the cultures were centrifuged as described above except the promastigote pellet was discarded and the media decanted into sterile flasks. The addition of 434 g $(NH_4)_2SO_4$ per liter precipitated active GUS protein from the medium; the salted out medium was stored at 4° C. overnight. Precipitated proteins were harvested either by centrifugation at 10,500×g for 30 min. or filtration through Gelman Supor-800 membrane; the proteins were resuspended in 10 mM Tris pH 8, 1 mM $CaCl_2$ and stored at −80° C. until dialysis. The crude preparations from several liters of medium were thawed, pooled, placed in dialysis tubing (Spectra/Por −7, MWCO 25,000), and dialyzed overnight against two 1 liter volumes of DMEM with bicarbonate (Dulbecco's Modified Eagle's Medium).

Example 3

GILT Uptake Assay

Skin fibroblast line GM4668 (human, NIGMS Human Genetic Mutant Cell Repository) is derived from a patient with mucopolysaccharidosis VII; the cells therefore have little or no β-GUS activity. GM4668 cells are therefore particularly useful for testing the uptake of GUS-GILT constructs into human cells. GM4668 cells were cultured in 12-well tissue culture plates in Dulbecco's modified Eagle's medium (DMEM) supplemented with 15% (v/v) fetal calf serum at 37° C. in 5% $CO_2$. Fibroblasts were cultured overnight in the presence of about 150 units of preparations of *Leishmania*-expressed human β-glucuronidase (GUS), GUS-IGF-II fusion protein (GUS-GILT), or mutant GUS-IGF-II fusion protein (GUSΔ-GILT) prepared as described in Example 2. Control wells contained no added enzyme (DMEM media blank). After incubation, media was removed from the wells and assayed in triplicate for GUS activity. Wells were washed five times with 1 ml of 37° C. phosphate-buffered saline, then incubated for 15 minutes at room temperature in 0.2 ml of lysis buffer (10 mM Tris, pH 7.5, 100 mM NaCl, 5 mM EDTA, 2 mM 4-(2-aminoethyl)-benzenesulfonyl fluoride hydrochloride (AEBSF, Sigma), and 1% NP-40). Cell lysates were transferred to microfuge tubes, then spun at 13,000 rpm for 5 minutes to remove cell debris. Three 10 µL aliquots of lysate were assayed for protein concentration (Pierce Micro BCA protein assay, Pierce, Ill.).

Three 38 µL aliquots of lysate were assayed for GUS activity using a standard fluorometric assay adapted from Wolfe et al. (1996) *Protocols for Gene Transfer in Neuroscience: Towards Gene Therapy of Neurological Disorders* 263-274. Assays are done in disposable fluorimeter cuvettes. 150 µl of reaction mix is added to each cuvette. 1 ml of reaction mix is 860 µl $H_2O$, 100 µl 1 µM NaAcetate, and 40 µl 25× β-GUS substrate mix. [25×β-GUS substrate mix is a suspension of 250 mg 4-methylumbelliferyl-β-D glucuronide in 4.55 ml ethanol stored at ±20° C. in a dessicator]. 38 µl of sample are added to the reaction mix and the reaction is incubated at 37° C. Reactions are terminated by addition of 2 ml stop solution (10.6 g $Na_2CO_3$, 12.01 g glycine, $H_2O$ to 500 ml, pH 10.5). Fluorescence output is then measured by fluorimeter.

Figure 5:
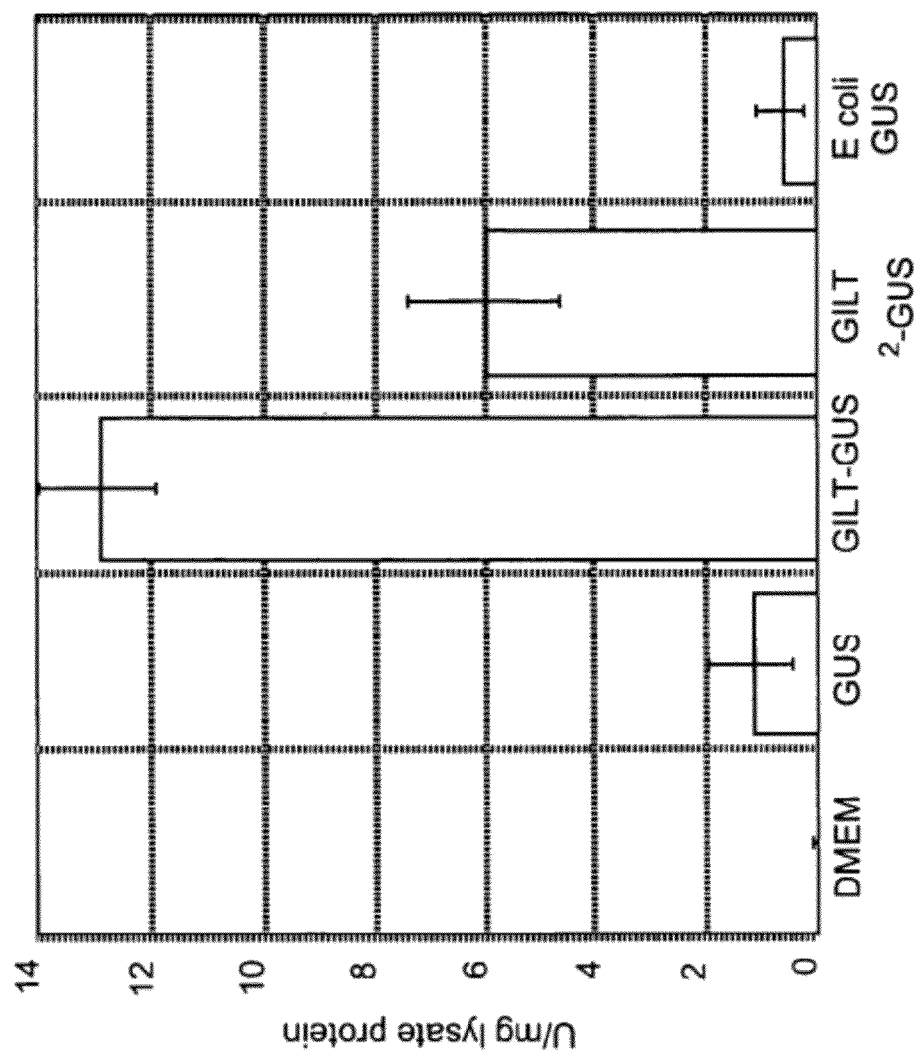

Results of the uptake experiment indicate that the amount of cell-associated GUS-GILT is 10-fold greater than that of the unmodified GUS (FIG. 5). The double mutant construct is about 5-fold more effective than unmodified GUS. These results indicate that the GILT technology is an effective means of targeting a lysosomal enzyme for uptake. Uptake can also be verified using standard immunofluorescence techniques.

Example 4

Competition Experiments

To verify that the GILT-mediated uptake occurs via the IGF-II binding site on the cation-independent M6P receptor, competition experiments were performed using recombinant IGF-II. The experimental design was identical to that described above except that GM4668 fibroblasts were incubated with indicated proteins in DMEM minus serum+2% BSA for about 18 hours. Each β-GUS derivative was added at 150 Upper well. 2.85 µg IGF-II was added to each well for competition. This represents approximately a 100 fold molar excess over GILT-GUS, a concentration sufficient to compete for binding to the M6P/IGF-II receptor.

Figure 6:
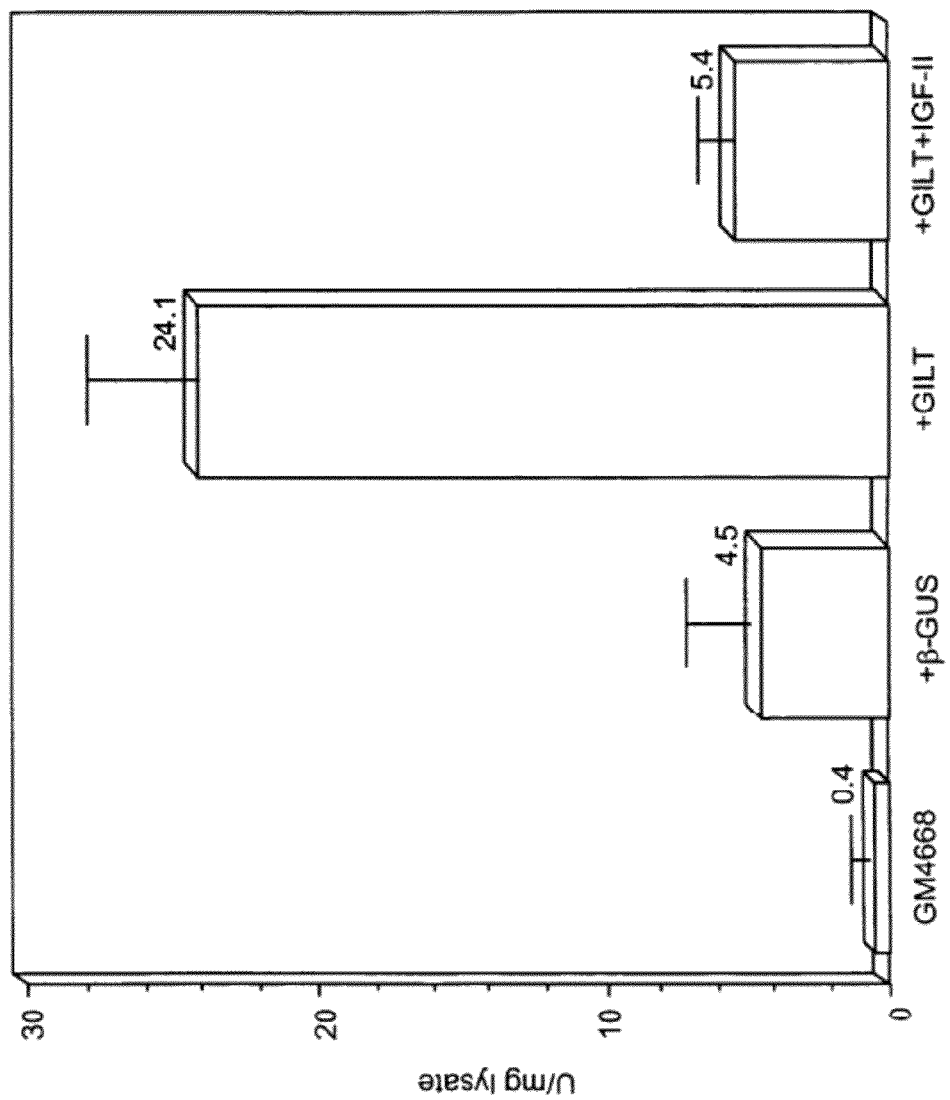

Results of the competition experiment are depicted in FIG. 6. In the absence of IGF-II over 24 units of GILT-GUS/mg lysate were detected. Upon addition of IGF-II, the amount of cell associated GILT-GUS fell to 5.4 U. This level is similar to the level of unmodified GUS taken up by the fibroblasts. Thus, the bulk of the GILT protein uptake can be competed by IGF-II indicating that the uptake is indeed occurring through a specific receptor-ligand interaction.

Example 5

Gene Product Expression in Serum Free Media

Expression products have also been isolated from serum free media. In general, the expression strain is grown in medium with serum, diluted into serum free medium, and allowed to grow for several generations, preferably 2-5 generations, before the expression product is isolated. For example, secreted targeted therapeutic proteins were isolated from *Leishmania mexicana* promastigotes cultured initially in 50 ml 1×M199 medium in a 75 cm² flask at 27° C. When the cell density reached $1-3 \times 10^7$/ml, the culture was used to inoculate 1.2 L of M199 media. When the density of this culture reached about $5 \times 10^6$/ml, the cells were harvested by centrifugation, resuspended in 180 ml of the supernatant and used to inoculate 12 L of "Zima" medium in a 16 L spinner flask. The initial cell density of this culture was typically about 5×10$^5$/ml. This culture was expanded to a cell density of about 1.0-1.7×10 e$^7$ cells/ml. When this cell density was reached, the cells were separated from the culture medium by centrifugation and the supernatant was filtered at 4° C. through a 0.2µ filter to remove residual promastigotes. The filtered media was concentrated from 12.0 L to 500 ml using a tangential flow filtration device (MILLIPORE Prep/Scale-TFF cartridge).

Preferred growth media for this method are M199 and "Zima" growth media. However, other serum containing and serum free media are also useful. M199 growth media is as follows: (1 L batch)=200 ml 5×M199 (with phenol red pH indicator)+636 ml H$_2$O, 50.0 ml fetal bovine serum, 50.0 ml EF bovine embryonic fluid, 1.0 ml of 50 mg/ml nourseothricin, 2.0 ml of 0.25% hemin in 50% triethanolamine, 10 ml of 10 mM adenine in 50 mM Hepes pH 7.5, 40.0 ml of 1M Hepes pH 7.5, 1 ml of 0.1% biotin in 95% ethanol, 10.0 ml of penicillin/streptomycin. All sera used are inactivated by heat. The final volume=1 L and is filter sterilized. "Zima" modified M199 media is as follows: (20.0 L batch)=219.2 g M199 powder (O)phenol red+7.0 g sodium bicarbonate, 200.0 ml of 10 mM adenine in 50 mM Hepes pH 7.5, 800.0 ml of Hepes free acid pH 7.5, 20.0 ml 0.1% biotin in 95% ethanol, 200.0 ml penicillin/streptomycin, Final volume=20.0 L and is filter sterilized.

Figure 8:
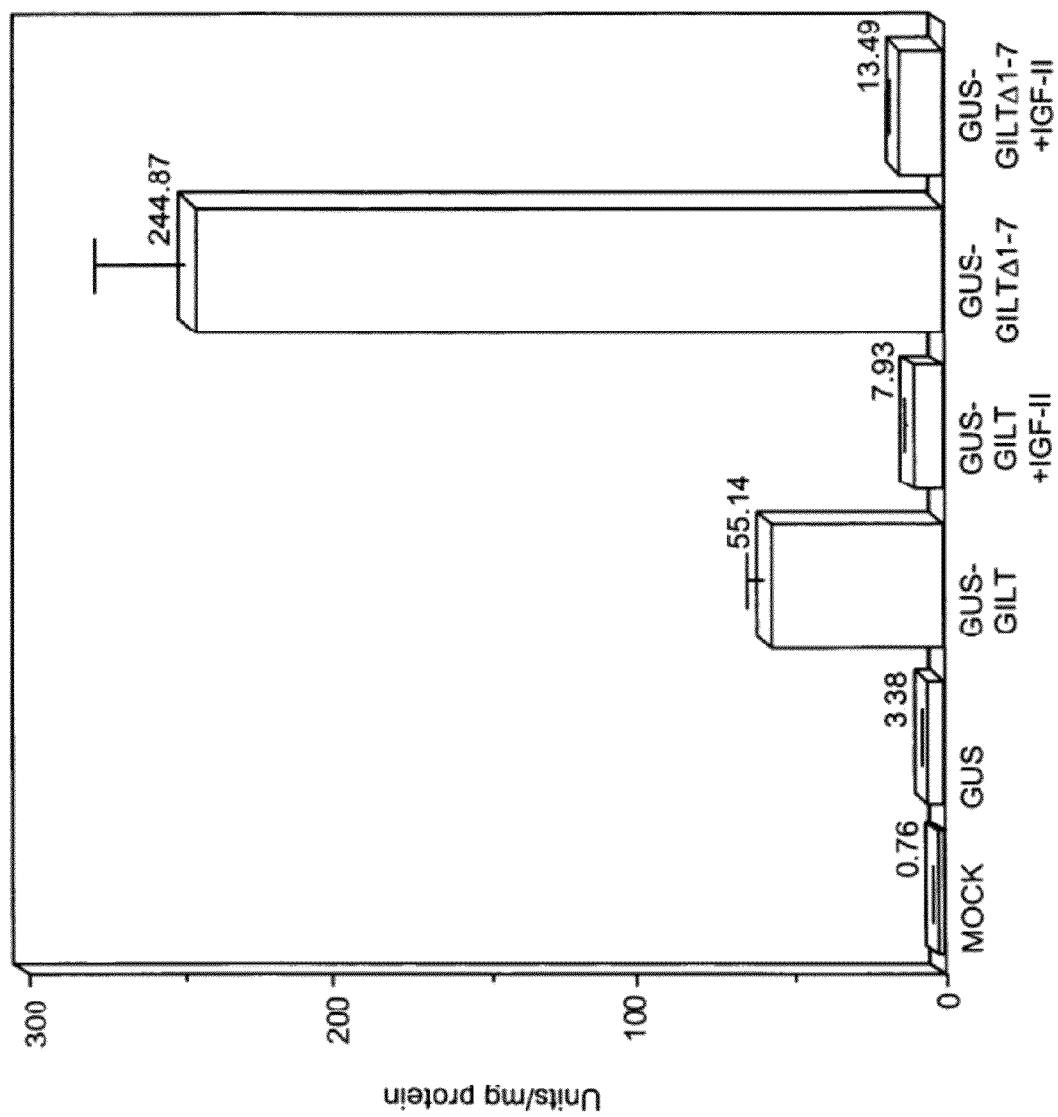

The targeted therapeutic proteins are preferably purified by Concanavalin A (Con A) chromatography. For example, when a culture of *L. mexicana* reached a density of >1.0×10$^7$ promastigotes/ml, the cells were removed by centrifugation, 10 min at 500×g. The harvested culture medium was passed through a 0.2 µm filter to remove particulates before being loaded directly onto a Con A-agarose column (4% cross-linked beaded agarose, Sigma). The Con A-agarose column was pretreated with 1 M NaCl, 20 mM Tris pH 7.4, 5 mM each of CaCl$_2$, MgCl$_2$ and MnCl$_2$ and then equilibrated with 5 volumes of column buffer (20 mM Tris pH 7.4, 1 mM CaCl$_2$, and 1 mM MnCl$_2$). A total of 179,800 units (nmol/hr) of GUS activity (in 2 L) in culture medium was loaded onto a 22 ml Con A agarose column. No activity was detectable in the flow through or wash. The GUS activity was eluted with column buffer containing 200 mM methyl mannopyranoside. Eluted fractions containing the activity peak were pooled and concentrated. Uptake and competition experiments were performed as described in Examples 3 and 4, except that the organisms were grown in serum-free medium and purified with ConA; about 350-600 units of enzyme were applied to the fibroblasts. Results are shown in FIG. 8.

Example 6

Competition Experiments Using Denatured IGF-II as Competitor

The experiment in Example 4 is repeated using either normal or denatured IGF-II as competitor. As in Example 4, the amount of cell-associated GUS-GILT is reduced when coincubated with normal IGF-II concentrations that are effective for competition but, at comparable concentrations, denatured IGF-II has little or no effect.

Example 7

Enzyme Assays

Assays for GUS activity are performed as described in Example 3 and/or as described below.

Glass assay tubes were numbered in triplicate, and 100 µL of 2×GUS reaction mix were added to each tube. 2×GUS reaction mix was prepared by adding 100 mg of 4-methylumbelliferyl-β-D glucuronide to 14.2 mL 200 mM sodium acetate, pH adjusted to 4.8 with acetic acid. Up to 100 µl of sample were added to each tube; water was added to a final reaction volume of 200 µL. The reaction tubes were covered with Parafilm and incubated in a 37° C. water bath for 1-2 hours. The reaction was stopped by addition of 1.8 mL of stop buffer (prepared by dissolving 10.6 g of Na$_2$CO$_3$ and 12.01 g of glycine in a final volume of 500 mL of water, adjusting the pH to 10.5 and filter-sterilizing into a repeat-dispenser). A fluorimeter was then calibrated using 2 mL of stop solution as a blank, and the fluorescence was read from the remaining samples. A standard curve was prepared using 1, 2, 5, 10, and 20 µL of a 166 µM 4-methylumbelliferone standard in a final volume of 2 mL stop buffer.

The 4-methylumbelliferone standard solution was prepared by dissolving 2.5 mg 4-methylumbelliferone in 1 mL ethanol and adding 99 mL of sterile water, giving a concentration of approximately 200 nmol/mL. The precise concentration was determined spectrophotometrically. The extinction coefficient at 360 nm is 19,000 cm$^{-1}$ M$^{-1}$. For example, 100 µL is added to 900 µL of stop buffer, and the absorbance at 360 nm is read. If the reading is 0.337, then the concentration of the standard solution is 0.337×10 (dilution)/19,000=177 µM, which can then be diluted to 166 µM by addition of an appropriate amount of sterile water.

Example 8

Binding Uptake and Halflife Experiments

Binding of GUS-GILT proteins to the M6P/IGF-II receptor on fibroblasts are measured and the rate of uptake is assessed similar to published methods (York et al. (1999) *J. Biol. Chem.* 274(2):1164-71). GM4668 fibroblasts cultured in 12 well culture dishes as described above are washed in ice-cold media minus serum containing 1% BSA. Ligand, (either GUS, GUS-GILT or GUS-ΔGILT, or control proteins) is added to cells in cold media minus serum plus 1% BSA. Upon addition of ligand, the plates are incubated on ice for 30 minutes. After 30 minutes, ligand is removed and cells are washed quickly 5 times with ice cold media. Wells for the 0 time point receive 1 ml ice cold stripping buffer (0.2 M Acetic acid, pH 3.5, and 0.5M NaCl). The plate is then floated in a 37° water bath and 0.5 ml prewarmed media is added to initiate uptake. At every stopping point, 1 ml of stripping buffer is added. When the experiment is over, aliquots of the stripping buffer are saved for fluorometric assay of β-glucuronidase activity as described in Example 3. Cells are then lysed as described above and the lysate assayed for β-glucuronidase activity. Alternatively, immunological methods can be used to test the lysate for the presence of the targeted therapeutic protein.

It is expected that GUS-GILT is rapidly taken up by fibroblasts in a matter of minutes once the temperature is shifted to 37° C. (York et al. (1999) *J. Biol. Chem.* 274(2):1164-71) and that the enzyme activity persists in the cells for many hours.

Example 9

Protein Production in Mammalian Cells

CHO Cells

GUS-GILTΔ1-7 and GUSΔC18-GILTΔ1-7 were expressed in CHO cells using the system of Ulmasov et al.

(2000) *PNAS* 97(26):14212-14217. Appropriate gene cassettes were inserted into the Eco RI site of the pCXN vector, which was electroporated into CHO cells at 50 μF and 1,200 V in a 0.4-cm cuvette. Selection of colonies and amplification was mediated by 400 μg/mL G418 for 2-3 weeks. The CHO cells were propagated in MEM media supplemented with 15% FBS, 1.2 mM glutamine, 50 μg/mL proline, and 1 mM pyruvate. For enzyme production, cells were plated in multifloor flasks in MEM. Once cells reached confluence, collection medium (Weymouth medium supplemented with 2% FBS, 1.2 mM glutamine, and 1 mM pyruvate) was applied to the cells. Medium containing the secreted recombinant enzyme was collected every 24-72 hours. A typical level of secretion for one GUS-GILTΔ1-7 cell line was 4000-5000 units/mL/24 hours.

A number of GUSΔC18-GILTΔ1-7 CHO lines were assayed for the amount of secreted enzyme produced. The six highest producers secreted between 8600 and 14900 units/mL/24 hours. The highest producing line was selected for collection of protein.

HEK 293 Cells

GUS-GILT cassettes were cloned into pCEP4 (Invitrogen) for expression in HEK 293 cells. Cassettes used included wild-type GUS-GILT; GUS-GILTΔ1-7; GUS-GILTY27L; GUSΔC18-GILTΔ1-7; GILTY27L; and GUS-GILTF19S/E12K.

HEK 293 cells were cultured to 50-80% confluency in 12-well plates containing DMEM medium with 4 mM glutamine and 10% FBS. Cells were transfected with pCEP-GUS-GILT DNA plasmids using FuGENE 6™ (Roche) as described by the manufacturer. 0.5 μg DNA and 2 μL of FuGENE 6™ were added per well. Cells were removed from wells 2-3 days after transfection using trypsin, then cultured in T25 cm² culture flasks containing the above DMEM medium with 100 μg/mL hygromycin to select for a stable population of transfected cells. Media containing hygromycin were changed every 2-3 days. The cultures were expanded to T75 cm² culture flasks within 1-2 weeks. For enzyme production cells were plated in multifloor flasks in DMEM. Once cells reached confluence, collection medium (Weymouth medium supplemented with 2% FBS, 1.2 mM glutamine, and 1 mM pyruvate) was applied to the cells. This medium has been optimized for CHO cells, not for 293 cells; accordingly, levels of secretion with the HEK 293 lines may prove to be significantly higher in alternate media.

Levels of secreted enzyme are shown in Table 4.

TABLE 4

| Cell line | Recombinant Protein | Units/mL/24 hours |
| --- | --- | --- |
| HEK293 2-1 | GUS-GILT | 3151 |
| HEK293 2-2 | GUSΔC18-GILTΔ1-7 | 10367 |
| HEK293 2-3 | GUS-GILTΔ1-7 | 186 |
| HEK293 4-4 | GILTY27L | 3814 |
| HEK293 3-5 | GUS-GILTF19S/E12K | 13223 |
| HEK293 3-6 | GILTY27L | 7948 |
| CHO 15 | GUSΔC18-GILTΔ1-7 | 18020 |

Example 10

Purification of GUS-GILT Fusion Proteins

Chromatography, including conventional chromatography and affinity chromatography, can be used to purify GUS-GILT fusion proteins.

Conventional Chromatography

One procedure for purifying GUS-GILT fusion proteins produced in *Leishmania* is described in Example 2. An alternative procedure is described in the following paragraph.

Culture supernatants from *Leishmania mexicana* cell lines expressing GUS-GILT fusions were harvested, centrifuged, and passed through a 0.2μ A filter to remove cell debris. The supernatants were concentrated using a tangential ultrafilter with a 100,000 molecular weight cut-off and stored at −80° C. Concentrated supernatants were loaded directly onto a column containing Concanavalin A (Con A) immobilized to beaded agarose. The column was washed with ConA column buffer (50 mM Tris pH 7.4, 1 mM $CaCl_2$, and 1 mM $MnCl_2$) before mannosylated proteins including GUS-GILT fusions were eluted using a gradient of 0-0.2M methyl-α-D-pyranoside in the ConA column buffer. Fractions containing glucuronidase activity (assayed as described in Example 7) were pooled, concentrated, and the buffer exchanged to SP column buffer (25 mM sodium phosphate pH 6, 20 mM NaCl, 1 mM EDTA) in preparation for the next column. The concentrated fractions were loaded onto an SP fast flow column equilibrated in the same buffer, and the column was washed with additional SP column buffer. The GUS-GILT fusions were eluted from the column in two steps: 1) a gradient of 0-0.15 M glucuronic acid in 25 mM sodium phosphate pH 6 and 10% glycerol, followed by 0.2 M glucuronic acid, 25 mM sodium phosphate pH 6, 10% glycerol. Fractions containing glucuronidase activity were pooled, and the buffer exchanged to 20 mM potassium phosphate pH 7.4. These pooled fractions were loaded onto an HA-ultragel column equilibrated with the same buffer. The GUS-GILT fusion proteins were eluted with an increasing gradient of phosphate buffer, from 145-340 mM potassium phosphate pH 7.4. The fractions containing glucuronidase activity were pooled, concentrated, and stored at −80° C. in 20 mM Tris pH 8 with 25% glycerol.

A conventional chromatography method for purifying GUS-GILT fusion proteins produced in mammalian cells is described in the following paragraphs.

Mammalian cells overexpressing a GUS-GILT fusion protein were grown to confluency in Nunc Triple Flasks, then fed with serum-free medium (Waymouth MB 752/1) supplemented with 2% fetal bovine serum to collect enzyme for purification. The medium was harvested and the flasks were re-fed at 24 hour intervals. Medium from several flasks were pooled and centrifuged at 5000×g for 20 minutes at 4° C. to remove detached cells, etc. The supernatant was removed and aliquots are taken for β-GUS assays. The medium can now be used directly for purification or frozen at −20° C. for later use.

1 L of secretion medium was thawed at 37° C. (if frozen), filtered through a 0.2μ filter, and transferred to a 4 L beaker. The volume of the medium was diluted 4-fold by addition of 3 L of dd water to reduce the salt concentration; the pH of the diluted medium was adjusted to 9.0 using 1 M Tris base. 50 mL of DEAE-Sephacel pre-equilibrated with 10 mM Tris pH 9.0 was added to the diluted medium and stirred slowly with a large stirring bar at 4° C. for 2 hours. [A small aliquot can be removed, microfuged, and the supernatant assayed to monitor binding.] When binding is complete, the resin was collected on a fritted glass funnel and washed with 750 mL of 10 mM Tris pH 9.0 in several batches. The resin was transferred to a 2.5 cm column and washed with an additional 750 mL of the same buffer at a flow rate of 120 mL/hour. The DEAE column was eluted with a linear gradient of 0-0.4 M NaCl in 10 mM Tris pH 9.0. The fractions containing the GUS-GILT fusion proteins were detected by 4-methylumbelliferyl-β-D glucuronide assay, pooled, and loaded onto a 600 mL column of Sephacryl S-200 equilibrated with 25 mM Tris pH 8, 1 mM β-glycerol phosphate, 0.15 M sodium chloride and eluted with the same buffer.

The fractions containing the GUS-GILT fusion proteins were pooled and dialyzed with 3×4 L of 25 mM sodium acetate pH 5.5, 1 mM β-glycerol phosphate, 0.025% sodium azide. The dialyzed enzyme was loaded at a flow rate of 36 mL/hour onto a 15 mL column of CM-Sepharose equilibrated with 25 mM sodium acetate pH 5.5, 1 mM β-glycerol phosphate, 0.025% sodium azide. It was then washed with 10 column volumes of this same buffer. The CM column was eluted with a linear gradient of 0-0.3 M sodium chloride in the equilibration buffer. The fractions containing the GUS-GILT fusion proteins were pooled and loaded onto a 2.4×70 cm (Bed volume=317 mL) column of Sephacryl S-300 equilibrated with 10 mM Tris pH 7.5, 1 mM β-glycerol phosphate, 0.15 M NaCl at a flow rate of 48 mL/hour. The fractions containing the fusion proteins were pooled; the pool was assayed for GUS activity and for protein concentration to determine specific activity. Aliquots were run on SDS-PAGE followed by Coomassie or silver staining to confirm purity. If a higher concentration of enzyme was required, Amicon Ultrafiltration Units with an XM-50 membrane (50,000 molecular weight cut-off) or Centricon C-30 units (30,000 molecular weight cut-off) were used to concentrate the fusion protein. The fusion protein is stored at −80° C. in the 10 mM Tris pH 7.5, 1 mM sodium β-glycerol phosphate, 0.15 M NaCl buffer.

Affinity Chromatography

Affinity chromatography conditions were essentially as described in Islam et al. (1993) *J. Biol. Chem.* 268(30):22627-22633. Conditioned medium from mammalian cells overexpressing a GUS-GILT fusion protein (collected and centrifuged as described above for conventional chromatography) was filtered through a 0.22µ filter. Sodium chloride (crystalline) was added to a final concentration of 0.5M, and sodium azide was added to a final concentration of 0.025% by adding 1/400 volume of a 10% stock solution. The medium was applied to a 5 mL column of anti-human β-glucuronidase-Affigel 10 (pre-equilibrated with Antibody Sepharose Wash Buffer: 10 mM Tris pH 7.5, 10 mM potassium phosphate, 0.5 M NaCl, 0.025% sodium azide) at a rate of 25 mL/hour at 4° C. Fractions were collected and monitored for any GUS activity in the flow-through. The column was washed at 36 mL/hour with 10-20 column volumes of Antibody Sepharose Wash Buffer. Fractions were collected and monitored for GUS activity. The column was eluted at 36 mL/hour with 50 mL of 10 mM sodium phosphate pH 5.0+3.5 M $MgCl_2$. 4 mL fractions were collected and assayed for GUS activity. Fractions containing the fusion protein were pooled, diluted with an equal volume of P6 buffer (25 mM Tris pH 7.5, 1 mM β-glycerol phosphate, 0.15 mM NaCl, 0.025% sodium azide) and desalted over a BioGel P6 column (pre-equilibrated with P6 buffer) to remove the $MgCl_2$ and to change the buffer to P6 buffer for storage. The fusion protein was eluted with P6 buffer, fractions containing GUS activity were pooled, and the pooled fractions assayed for GUS activity and for protein. An SDS-PAGE gel stained with Coomassie Blue or silver stain was used to confirm purity. The fusion protein was stored frozen at −80° C. in P6 buffer for long-term stability.

Example 11

Uptake Experiments on Mammalian-Produced Proteins

Culture supernatants from HEK293 cell lines or CHO cell lines producing GUS or GUS-GILT constructs were harvested through a 0.2 µm filter to remove cells. GM 4668 fibroblasts were cultured in 12-well tissue culture plates in DMEM supplemented with 15% (v/v) fetal calf serum at 37° C. in 5% $CO_2$. Cells were washed once with uptake medium (DMEM+2% BSA (Sigma A-7030)) at 37° C. Fibroblasts were then cultured (3-21 hours) with 1000-4000 units of enzyme per mL of uptake medium. In some experiments, competitors for uptake were added. Mannose-6-phosphate (Calbiochem 444100) was added to some media at concentrations from 2-8 mM and pure recombinant IGF-II (Cell Sciences OU100) was added to some media at 2.86 mM, representing a 10-100 fold molar excess depending on the quantity of input enzyme. Uptake was typically measured in triplicate wells.

After incubation, the media were removed from the wells and assayed in duplicate for GUS activity. Wells were washed five times with 1 mL of 37° C. phosphate-buffered saline, then incubated for 15 minutes at room temperature in 0.2 mL of lysis buffer (10 mM Tris, pH 7.5, 100 mM NaCl, 5 mM EDTA, and 1% NP-40). Cell lysates were transferred to microfuge tubes and spun at 13,000 rpm for 5 minutes to remove cell debris. Two 10 µL aliquots of lysate were assayed for GUS activity using a standard fluorometric assay. Three 10 µL aliquots of lysate were assayed for protein concentration (Pierce Micro BCA protein assay, Pierce, Ill.).

An initial experiment compared uptake of CHO-produced GUS-GILTΔ1-7 with CHO-produced GUSΔC18-GILTΔ1-7. As shown in Table 5, the GUSΔC18-GILTΔ1-7 protein, which was engineered to eliminate a potential protease cleavage site, has significantly higher levels of uptake levels that can be inhibited by IGF-II or by M6P. In contrast, the uptake of a recombinant GUS produced in mammalian cells lacking the IGF-II tag was unaffected by the presence of excess IGF-II but was completely abolished by excess M6P. In this experiment, uptake was performed for 18 hours.

TABLE 5

| Enzyme | Input units | Uptake (units/mg) | +IGF-II (units/mg) | % IGF-II inhibition | +M6P (units/mg) | % M6P inhibition |
|---|---|---|---|---|---|---|
| CHO GUS-GILTΔ1-7 | 982 | 310 ± 27 | 84 ± 20 | 73 | 223 ± 36 | 28 |
| CHO GUSΔC18-GILTΔ1-7 | 1045 | 704 ± 226 | 258 ± 50 | 63 | 412 ± 79 | 41 |
| CHO GUS | 732 | 352 ± 30 | 336 ± 77 | 5 | 1 ± 0.2 | 99.7 |

A subsequent experiment assessed the uptake of CHO- and HEK293-produced enzymes by human fibroblasts from MPSVII patients. In this experiment, uptake was performed for 21 hours.

TABLE 6

| Enzyme | Input units | Uptake (units/mg) | +IGF-II Uptake (units/mg) | % IGF-II inhibition |
|---|---|---|---|---|
| CHO GUSΔC18-GILTΔ1-7 | 2812 | 4081 ± 1037 | 1007 ± 132 | 75 |
| HEK GUS-GILT | 2116 | 1432 ± 196 | | |
| HEK GUSΔC18-GILTΔ1-7 | 3021 | 5192 ± 320 | 1207 ± 128 | 77 |
| HEK GUS-GILTY27L | 3512 | 1514 ± 203 | | |
| HEK GUS-GILTF19SE12K | 3211 | 4227 ± 371 | 388 ± 96 | 90.8 |
| HEK GUS-GILTF19S | 3169 | 4733 ± 393 | 439 ± 60 | 90.7 |

A further experiment assessed the uptake of selected enzymes in the presence of IGF-II, 8 mM M6P, or both inhibitors. Uptake was measured for a period of 22.5 hours.

TABLE 7

| Enzyme | Input units | Uptake (units/mg) | +IGF-II (units/mg) | % IGF-II inhibition | +M6P (units/mg) | % M6P inhibition | +IGF-II + M6P (units/mg) | % IGF-II + M6P inhibition |
|---|---|---|---|---|---|---|---|---|
| CHO GUSΔC18-GILTΔ1-7 | 1023 | 1580 ± 150 | 473 ± 27 | 70 | 639 ± 61 | 60 | 0 ± 1 | 100 |
| HEK GUS-GILTF19S E12K | 880 | 1227 ± 76 | 22 ± 2 | 98.2 | 846 ± 61 | 31 | 0 ± 3 | 100 |
| HEK GUS- GILTF19S | 912 | 1594 ± 236 | 217 ± 17 | 86 | 952 ± 96 | 60 | 15 ± 2 | 99.06 |

The experiments described above show that CHO and HEK293 production systems are essentially equivalent in their ability to secrete functional recombinant proteins. The experiments also show that the presence of excess IGF-II diminishes uptake of tagged proteins by 70-90+%, but does not markedly affect uptake of untagged protein (4.5%), indicating specific IGF-II-mediated uptake of the mammalian-produced protein. Unlike *Leishmania*-produced proteins, the enzymes produced in mammalian cells are expected to contain M6P. The presence of two ligands on these proteins capable of directing uptake through the M6P/IGF-II receptor implies that neither excess IGF-II nor excess M6P should completely abolish uptake. Furthermore, since the two ligands bind to discrete locations on the receptor, binding to the receptor via one ligand should not be markedly affected by the presence of an excess of the other competitor.

Example 12

GILT-Modified Enzyme Replacement Therapy for Fabry's Disease

The objective of these experiments is to evaluate the efficacy of GILT-modified alpha-galactosidase A (α-GAL A) as an enzyme replacement therapy for Fabry's disease.

Fabry's disease is a lysosomal storage disease resulting from insufficient activity of α-GAL A, the enzyme responsible for removing the terminal galactose from GL-3 and other neutral sphingolipids. The diminished enzymatic activity occurs due to a variety of missense and nonsense mutations in the X-linked gene. Accumulation of GL-3 is most prevalent in lysosomes of vascular endothelial cells of the heart, liver, kidneys, skin and brain but also occurs in other cells and tissues. GL-3 buildup in the vascular endothelial cells ultimately leads to heart disease and kidney failure.

Enzyme replacement therapy is an effective treatment for Fabry's disease, and its success depends on the ability of the therapeutic enzyme to be taken up by the lysosomes of cells in which GL-3 accumulates. The Genzyme product, Fabrazyme, is recombinant α-GAL A produced in DUKX B11 CHO cells that has been approved for treatment of Fabry's patients in Europe due to its demonstrated efficacy.

The ability of Fabrazyme to be taken up by cells and transported to the lysosome is due to the presence of mannose 6-phosphate (M6P) on its N-linked carbohydrate. Fabrazyme is delivered to lysosomes through binding to the mannose-6-phosphate/IGF-II receptor, present on the cell surface of most cell types, and subsequent receptor-mediated endocytosis. Fabrazyme reportedly has three N-linked glycosylation sites at ASN residues 108, 161, and 184. The predominant carbohydrates at these positions are fucosylated biantennary bisialylated complex, monophosphorylated mannose-7 oligomannose, and biphosphorylated mannose-7 oligomannose, respectively.

The glycosylation independent lysosomal targeting (GILT) technology of the present invention directly targets therapeutic proteins to the lysosome via a different interaction with the IGF-II receptor. A targeting ligand is derived from mature human IGF-II, which also binds with high affinity to the IGF-II receptor. In current applications, the IGF-II tag is provided as a C-terminal fusion to the therapeutic protein, although other configurations are feasible including cross-linking. The competency of GILT-modified enzymes for uptake into cells has been established using GILT-modified β-glucuronidase, which is efficiently taken up by fibroblasts in a process that is competed with excess IGF-II. Advantages of the GILT modification are increased binding to the M6P/IGF-II receptor, enhanced uptake into lysosomes of target cells, altered or improved pharmacokinetics, and expanded, altered or improved range of tissue distribution. The improved range of tissue distributions could include delivery of GILT-modified α-GAL A across the blood-brain barrier since IGF proteins demonstrably cross the blood-brain barrier.

Another advantage of the GILT system is the ability to produce uptake-competent proteins in non-mammalian expression systems where M6P modifications do not occur. In certain embodiments, GILT-modified protein is produced primarily in CHO cells. In certain others, the GILT tag is placed at the C-terminus or N-terminus of α-GAL A, although the invention is not so limited.

GILT-Modified α-GAL A Construct

Human α-GAL A DNA cassettes for generation of GILT-modified α-GAL A (GAL-GILTΔ1-7) or unmodified α-GAL A (GAL) constructs were derived from plasmid pCC4 (ATCC#68266) by PCR. The sequences of GAL-GILTΔ1-7 (SEQ ID NO:25) and GAL (SEQ ID NO:26) cassettes are shown in FIGS. 27 and 28, respectively. The two cassettes were cloned into the Xho I and Xma I restriction sites of expression vector pISSWA, creating plasmids pISSWA-GAL-GILTΔ1-7-1 and pISSWA-GAL-1, respectively. pISSWA has a CMV promoter to drive high level expression of proteins in mammalian cells. The sequence of pISSWA vector (SEQ ID NO:27) is shown in FIG. 29.

Circular plasmids pISSWA-GLA-GILTΔ1-7 and pISSWA-GLA-1 were linearized by digestion with endonuclease Swa I. The linearized DNA fragments were then transfected into CHO-K1 cells (ATCC CCL-61) grown in 6-well tissue culture plates in CHO media (MEM media supplemented with 15% FBS, 1.2 mM glutamine, 50 µg/ml proline, and 1 mM pyruvate) using the FuGENE6™ transfection reagent (Roche Diagnostics, Indianapolis, Ind.). According to the manufacturer's protocol, 2 µg of DNA was mixed with 8 µl of transfection reagent and delivered to each well of CHO cells. Two days after transfection, the CHO medium was replaced with fresh medium. Antibiotic G418 was added to the medium at a concentration of either 200 µg/ml or 400 µg/ml to select for stable transformants. Stable CHO colonies were isolated 2-3 weeks after transfection and maintained with G418 selection as attached cultures in tissue culture flasks.

Cell line 863.10 expressing GAL-GILTΔ1-7, and cell line 888.7 expressing GAL, were grown to saturation in CHO media in T225 tissue culture flasks. Collection media (Waymouth MB 752/1 media supplemented with 2% FBS, 1.2 mM glutamine, and 1 mM pyruvate) was then added to saturated cells, and this media was harvested daily and kept at −20° C. for future use. Supernatants from stable clonal lines collected above were assayed for the presence of α-GAL A activity using substrate 4-methylumbelliferyl-alpha-D-galactopyranoside (Sigma #M7633 available from Sigma-Aldrich, St. Louis, Mo.) as described by Desnick R. J. et al., (1973), *Journal of Laboratory and Clinical Medicine,* 81:157-181, the teachings of which are hereby incorporated by reference. Lines 863.10 and 888.7 each produced between 1,000 and 7,000 units per ml of α-GAL A activity in the supernatant. 1 unit is defined as 1 nmol substrate hydrolyzed per hour.

Partial Purification of GILT-Modified α-GAL A

30% (w/v) ammonium sulfate was added to harvested media from cell lines 863.10 and 888.7. Precipitated GAL-GILTΔ1-7 and GAL proteins were collected by centrifugation and resuspended in loading buffer (citrate-phosphate buffer with 250 mM NaCl, pH 6.5). 10 ml of each loading sample was mixed in batch with 1 ml of charged concanavalin A (Con A) agarose resins (Sigma C7555 available from Sigma-Aldrich, St. Louis, Mo.) that had been equilibrated with loading buffer, and gently mixed for 16 hours at 4° C. The resins were then washed two times with 14 ml of washing buffer (citrate-phosphate, 500 mM NaCl, pH 6.5). 1 ml of elution buffer (citrate-phosphate, 500 mM NaCl, 1M methylmannose, pH 6.5) was added to each batch of resins and mixed slowly at room temperature. This step was repeated twice. To remove methylmannose from the Con A purified α-GAL A enzyme, the eluted protein was spin-dialyzed in loading buffer using Nanosep™ centrifugal devices (Pall Life Sciences, Dreieich, Germany) with a dialysis tube having 30,000 molecular weight cut-off.

Uptake Experiments in α-GAL A—Deficient Fibroblasts

α-GAL A—deficient fibroblast cell line GM00107 (Coriell Cell Repository, Camden, N.J.) was cultured in 12-well tissue culture plates in Fb media (MEM supplemented with 15% FBS, 2× concentration of essential and non-essential amino acids and vitamins, and 2 mM glutamine) to about 50 to 80% confluence. Cells were washed once with uptake media (MEM with 2% bovine serum albumin (Sigma A7030 available from Sigma-Aldrich, St. Louis, Mo.) and 0.1 M HEPES pH 7.4), then cultured for 4 hours in 0.5 ml of uptake media containing 2,000 units of Con A purified α-GAL A enzyme. In some experiments, competitors for uptake were added in the uptake media. For example, mannose-6-phosphate (M6P) (Calbiochem 444100 available from Merck KGaA, Darmstadt, Germany) was added to some media at concentrations ranging from 2-8 mM as a competitor and recombinant IGF-II (Cell Sciences OU100 available from Cell Sciences, Inc., Canton, Mass.) was added to some media at a concentration of 2.86 mM as a competitor. In some experiments, both M6P and recombinant IGF-II were added to media as competitors. Each uptake experiment was conducted in duplicate.

After incubation, wells were washed four times with 1 ml of 37° C. phosphate buffered saline, then incubated for 15 minutes at room temperature in 0.2 ml of lysis buffer (citrate-phosphate, pH 6.5, 100 mM NaCl, 5 mM EDTA, and 0.5% NP-40). Cell lysates were transferred to microfuge tubes and spun at 13,000 rpm for five minutes to remove cell debris. Three 20 µl aliquots of lysate were assayed for α-GAL A activity using substrate 4-methylumbelliferyl-alpha-D-galactopyranoside (Sigma #M7633 available from Sigma-Aldrich, St. Louis, Mo.) as described by Desnick R. J. et al. (1973), *Journal of Laboratory and Clinical Medicine,* 81:157-181, the teachings of which are hereby incorporated by reference. Meanwhile, three 20 µl aliquots of same lysate were assayed for protein concentration using a Pierce Micro BCA protein assay (Pierce Biotechnology, Inc., Rockford, Ill.). Uptake was reported as U/mg lysate where 1U is defined as 1 nmol substrate hydrolyzed per hour. Uptake was normalized by setting the level of uptake in the presence of both M6P and recombinant IGF-II to be 0. Exemplary results of uptake experiments are illustrated in FIG. 30.

Example 13

GILT-Modified Enzyme Replacement Therapy for Pompe Disease

The objective of these experiments is to evaluate the efficacy of GILT-modified acid alpha-glucosidase (GAA) as an enzyme replacement therapy for Pompe disease.

The glycosylation independent lysosomal targeting (GILT) technology of the present invention permits M6P-independent targeting of GAA to patient lysosomes. In one embodiment, GAA or a catalytically-active fragment thereof is fused at its N-terminus to a targeting moiety including the signal peptide of human IGF-II. A targeting moiety including the signal peptide should improve secretion of GAA from host cells, thereby achieving high yield production and facilitating harvest of the therapeutic GILT-modified GAA. The desired GILT tag can be positioned at sites downstream of known cleavage sites to preclude removal of the GILT tag by possible proteolytic processing.

To identify which GILT-modified GAA construct is most enzymatically active and uptake-competent, constructs are transfected into HEK293 cells, CHO cells, or other suitable cells and culture supernatants from pools of clones are assayed for active enzyme and for uptake into Pompe fibroblast cells.

To test enzymatic activity, culture supernatants are assayed for GAA activity using the fluorogenic substrate, 4-methylumbelliferyl-α-D-glucopyranoside (Reuser et al. (1978) *Am J Hum Genet*, 30(2):132-43) or the colorometric substrate p-nitrophenyl-α-D-glucopyranoside. Total enzyme activity is normalized to cell number to compare relative levels of expression achieved by various clonal cell lines. To test uptake competency, the culture medium is collected, subjected to filtration, and applied to Pompe fibroblast cells. To assess specificity of uptake, cells are incubated for 3-16 hours in the presence or absence of 5 mM M6P, or IGF-II, or both. Pompe fibroblast cells are harvested and the cell associated GAA activity is measured.

The GILT-modified GAA with the most promising uptake characteristics and/or enzymatic activities are selected for large scale production in CHO cells or other suitable expression systems.

GAA deficient mice (available from Jackson Laboratories) are used to assess the ability of GILT-modified GAA to clear accumulated glycogen from tissues (Bijvoet et al. (1999) *J. Pathol.*, 189(3):416-24; Raben et al. (1998) *J. Biol. Chem.*, 273(30):19086-92). One exemplary protocol includes 4 weekly injections of 3-5 mice with doses of up to 100 mg/kg. Evaluation of the injected mice includes biochemical analysis of glycogen and GAA activity in selected tissues including various muscle tissues, heart, and liver as well as histopathological analysis to visualize glycogen deposits in tissues.

Targeted GAA enzymes can be constructed using human Image cDNA clone No. 4374238 from Open Biosystems. This clone contains a full length cDNA encoding human GAA isolated from library NIH_MGC_97 made from testis and cloned into pBluescript (pBluescript -GAA). The sequence of GAA in clone No. 4374238 is shown in FIG. 20 and in SEQ ID NO:23. Sequence analysis of GAA in clone No. 4374238 confirmed the presence of a full length cDNA with four silent nucleotide changes compared to the GenBank sequence NM_000152. Three of these have been noted previously as common single-nucleotide polymorphisms in GAA: 642C/T, 1581G/A, 2133A/G. The residues in bold are present in clone 4374238. The predicted heterozygosities for these three polymorphisms are about 0.23, 0.4, and 0.42, respectively, in the general population. The fourth polymorphism is 1665C/A.

Additional guidance on constructing targeted GAA fusion proteins is found in U.S. Ser. No. 60/543,812, filed Feb. 10, 2004, the teachings of which are herein incorporated by reference.

Example 14

In Vivo Therapy

General Considerations

GUS minus mice can be used to assess the effectiveness of GUS-GILT and derivatives thereof in enzyme replacement therapy. GUS minus mice are generated by heterozygous matings of B6.C-H-$2^{bml}$/ByBIR-gus$^{mps}$/+ mice as described by Birkenmeier et al. (1989) *J. Clin. Invest* 83(4):1258-6. Preferably, the mice are tolerant to human β-GUS. The mice may carry a transgene with a defective copy of human β-GUS to induce immunotolerance to the human protein (Sly et al. (2001) *PNAS* 98:2205-2210). Alternatively, human β-GUS (e.g. as a GUS-GILT protein) can be administered to newborn mice to induce immunotolerance.

Generally, preferred doses of a targeted therapeutic protein such as GUSΔC18-GILTΔ1-7 (in which GUSΔ18, a β-GUS protein omitting the last eighteen amino acids of the protein, is fused to the N-terminus of Δ1-7 GILT, an IGF-II protein missing the first seven amino acids of the mature protein) are in the range of 0.5-7 mg/kg body weight. For example, an enzyme dose can be about 1 mg/kg body weight administered intravenously, and the enzyme concentration about 1-3 mg/mL. As another example, a dose of about 5 mg/kg body weight of GUSΔC18-GILTΔ1-7 protein treated with periodate and sodium borohydride can be administered. Injections can, for example, be weekly.

Two other assay formats can be used. In one format, animals are given a single injection of 20,000U of enzyme in 100 μl enzyme dilution buffer (150 mM NaCl, 10 mM Tris, pH7.5). Mice are killed 72-96 hours later to assess the efficacy of the therapy. In a second format, mice are given weekly injections of 20,000 units over 3-4 weeks and are killed 1 week after the final injection. Histochemical and histopathologic analysis of liver, spleen and brain are carried out by published methods (Birkenmeier et al. (1991) *Blood* 78(11): 3081-92; Sands et al. (1994) *J. Clin. Invest* 93(6):2324-31; Daly et al. (1999) *Proc. Natl. Acad. Sci. USA* 96(5):2296-300). In the absence of therapy, cells (e.g. macrophages and Kupffer cells) of GUS minus mice develop large intracellular storage compartments resulting from the buildup of waste products in the lysosomes. As indicated in the "Experimental Results" section below, in cells in mice treated with GUS-GILT constructs, the size of these compartments is visibly reduced or the compartments shrink until they are no longer visible with a light microscope.

Similarly, humans with lysosomal storage diseases will be treated using constructs targeting an appropriate therapeutic portion to their lysosomes. In some instances, treatment will take the form of regular (e.g. weekly) injections of a GILT protein. In other instances, treatment will be achieved through administration of a nucleic acid to permit persistent in vivo expression of a GILT protein, or through administration of a cell (e.g. a human cell, or a unicellular organism) expressing the GILT protein in the patient. For example, the GILT protein can be expressed in situ using a *Leishmania* vector as described in U.S. Pat. No. 6,020,144, issued Feb. 1, 2000; U.S. Provisional Application No. 60/250,446, filed Nov. 30, 2000; and U.S. Provisional Application No. 60/290,281, "Protozoan Expression Systems for Lysosomal Storage Disease Genes", filed May 11, 2001.

Targeted therapeutic proteins of the invention can also be administered, and their effects monitored, using methods (enzyme assays, histochemical assays, neurological assays, survival assays, reproduction assays, etc.) previously described for use with GUS. See, for example, Vogler et al. (1993) *Pediatric Res.* 34(6):837-840; Sands et al. (1994) *J. Clin. Invest.* 93:2324-2331; Sands et al. (1997) *J. Clin. Invest.* 99:1596-1605; O'Connor et al. (1998) *J. Clin. Invest.* 101: 1394-1400; and Soper et al. (1999) 45(2):180-186.

Experimental Results

In vivo experiments were conducted to assess the ability of GILT-tagged β-glucuronidase to reverse the lysosomal storage pathology in the MPS VII mouse model for Sly syndrome. Three mice were infused via the tail vein three times at six-day intervals with CHO-produced GUSΔC18-GILTΔ1-7 (ΔΔ15) protein at a dose of 1 mg/kg. Three control mice were similarly infused via the tail vein three times at six-day intervals with CHO-produced untagged human β-glucuronidase (HBG) at a dose of 1 mg/kg. Both enzymes have not undergone deglycosylation treatment. Six days after the last infusion, the animals were sacrificed and tissue samples were processed for pathology/histology with blinded samples.

As shown in Table 8, certain clinically significant cells and tissues responded differently to ΔΔ15 and HBG. In each instance where a difference was detected, the GILT-tagged enzyme ΔΔ15 was more effective in eliminating storage material from the lysosome than the untagged enzyme HBG. For example, as illustrated in FIG. 24, glomerular epithelial cells in the kidney (podocytes) were completely restored to normal morphology when treated with the GILT-tagged enzyme ΔΔ15 (dd 15), while no effect was observed with the untagged enzyme HBG. Electron microscope images shown in FIG. 25 illustrate that podocytes from untreated mice or mice treated with HBG exhibit multiple spherical vacuoles, an indication of LSD pathology. In contrast, podocytes from mice treated with ΔΔ15 (HBG dd) do not exhibit comparable spherical vacuoles, indicating that the storage materials were eliminated from podocytes in treated MPS VII mice. Similar results were obtained in tubular kidney epithelial cells. In addition, as illustrated in FIG. 26, in bone osteoblasts, cells involved in bone production and homeostasis, the GILT-tagged enzyme ΔΔ15 cleared storage material from the lysosome significantly better than did the untagged enzyme HBG. However, both ΔΔ15 and HBG restored normal morphology to certain tissues (e.g. liver macrophage and hepatocytes, spleen, bone marrow, and adrenal interstitial cells) because saturating levels of both enzymes were injected in the experiments.

The superior ability of the GILT-tagged enzyme to reverse the storage pathology in the kidney and in osteoblasts demonstrates a great potential of the GILT targeting technology to produce improved enzyme-replacement therapeutics for the treatment of lysosomal storage diseases. These data have a particular relevance for Fabry disease where kidney failure is a primary concern and for Gaucher disease where bone anomalies are observed in patients receiving Cerezyme®, a recombinant glucocerebrosidase provided by Genzyme Corporation (Framingham, Mass.).

TABLE 8

Comparison of in vivo therapeutic effect using untagged human β-glucuronidase (HBG) and GUSΔC18-GILTΔ1-7 (ΔΔ15) in MPS VII mice

| Tissue | HBG 5 (n = 3) | ΔΔ15 (n = 3) |
| --- | --- | --- |
| Renal Tubular Epithelial Cells | +/++ | ++/+++ |
| Glom Epithelial Cell | NC | +++ |
| Heart Valve | NC/+ | NC/++ |
| Bone Sinus Lining Cells | +++ | +++ |
| Bone Osteoblast Lining the Bone | NC/++ | ++/+++ |
| Bone Marrow | +++ | +++ |
| Adrenal Interstitial Cells | +++ | +++ |
| Liver Sinus Lining Cells | +++ | +++ |
| Hepatocytes | +++ | +++ |
| Spleen Sinus Lining Cells | +++ | +++ |
| Cornea | NC | NC |
| Retinal Pigment Epithelium | NC | NC |

+++: Marked decrease in vacuolization, essentially identical to the morphology in the normal animal.
++: Moderate decrease in cytoplasmic vacuolization.
+: Slight and/or focal decrease in cytoplasmic vacuolization.
NC: No change, storage similar to untreated mutant.

Example 15

Underglycosylated Therapeutic Proteins

The efficacy of a targeted therapeutic can be increased by extending the serum half-life of the targeted therapeutic. Hepatic mannose receptors and asialoglycoprotein receptors eliminate glycoproteins from the circulation by recognizing specific carbohydrate structures (Lee et al. (2002) *Science* 295(5561):1898-1901; Ishibashi et al. (1994) *J. Biol. Chem.* 269(45):27803-6). In some embodiments, the present invention permits targeting of a therapeutic to lysosomes and/or across the blood brain barrier in a manner dependent not on a carbohydrate, but on a polypeptide or an analog thereof. Actual underglycosylation of these proteins is expected to greatly increase their half-life in the circulation, by minimizing their removal from the circulation by the mannose and asialoglycoprotein receptors. Similarly, functional deglycosylation (e.g. by modifying the carbohydrate residues on the therapeutic protein, as by periodate/sodium borohydride treatment) achieves similar effects by interfering with recognition of the carbohydrate by one or more clearance pathways. Nevertheless, because targeting of the protein relies, in most embodiments, on protein-receptor interactions rather than carbohydrate-receptor interactions, modification or elimination of glycosylation should not adversely affect targeting of the protein to the lysosome and/or across the blood brain barrier.

Any lysosomal enzyme using a peptide targeting signal such as can be chemically or enzymatically deglycosylated or modified to produce a therapeutic with the desirable properties of specific lysosomal targeting plus long serum half-life. In the case of some lysosomal storage diseases where it might be important to deliver the therapeutic to macrophage or related cell types via mannose receptor, fully glycosylated therapeutics can be used in combination with underglycosylated targeted therapeutics to achieve targeting to the broadest variety of cell types.

Proteins Underglycosylated when Synthesized

In some cases it will be preferable to produce the targeted therapeutic protein initially in a system that does not produce a fully glycosylated protein. For example, a targeted therapeutic protein can be produced in *E. coli*, thereby generating a completely unglycosylated protein. Alternatively, an unglycosylated protein is produced in mammalian cells treated with tunicamycin, an inhibitor of Dol-PP-GlcNAc formation. If, however, a particular targeted therapeutic does not fold correctly in the absence of glycosylation, it is preferably produced initially as a glycosylated protein, and subsequently deglycosylated or rendered functionally underglycosylated.

Underglycosylated targeted therapeutic proteins can also be prepared by engineering a gene encoding the targeted therapeutic protein so that an amino acid that normally serves as an acceptor for glycosylation is changed to a different amino acid. For example, an asparagine residue that serves as an acceptor for N-linked glycosylation can be changed to a glutamine residue, or another residue that is not a glycosylation acceptor. This conservative change is most likely to have a minimal impact on enzyme structure while eliminating glycosylation at the site. Alternatively, other amino acids in the vicinity of the glycosylation acceptor can be modified, disrupting a recognition motif for glycosylation enzymes without necessarily changing the amino acid that would normally be glycosylated.

In the case of GUS, removal of any one of 4 potential glycosylation sites lessens the amount of glycosylation while retaining ample enzyme activity (Shipley et al. (1993) *J. Biol.*

Chem. 268(16):12193-8). Removal of some sets of two glycosylation sites from GUS still permits significant enzyme activity. Removal of all four glycosylation sites eliminates enzyme activity, as does treatment of cells with tunicamycin, but deglycosylation of purified enzyme results in enzymatically active material. Therefore, loss of activity associated with removal of the glycosylation sites is likely due to incorrect folding of the enzyme.

Other enzymes, however, fold correctly even in the absence of glycosylation. For example, bacterial β-glucuronidase is naturally unglycosylated, and can be targeted to a mammalian lysosome and/or across the blood brain barrier using the targeting moieties of the present invention. Such enzymes can be synthesized in an unglycosylated state, rather than, for example, synthesizing them as glycosylated proteins and subsequently deglycosylating them.

Deglycosylation

If the targeted therapeutic is produced in a mammalian cell culture system, it is preferably secreted into the growth medium, which can be harvested, permitting subsequent purification of the targeted therapeutic by, for example, chromatographic purification protocols, such as those involving ion exchange, gel filtration, hydrophobic chromatography, ConA chromatography, affinity chromatography or immunoaffinity chromatography.

Chemical deglycosylation of glycoproteins can be achieved in a number of ways, including treatment with trifluoromethane sulfonic acid (TFMS), or treatment with hydrogen fluoride (HF).

Chemical deglycosylation by TFMS (Sojar et al. (1989) *J. Biol. Chem.* 264(5):2552-9; Sojar et al. (1987) *Methods Enzymol.* 138:341-50): 1 mg GILT-GUS is dried under vacuum overnight. The dried protein is treated with 150 µl TFMS at 0° C. for 0.5-2 hours under nitrogen with occasional shaking. The reaction mix is cooled to below −20° C. in a dry ice-ethanol bath and the reaction is neutralized by the gradual addition of a prechilled (−20° C.) solution of 60% pyridine in water. The neutralized reaction mix is then dialyzed at 4° C. against several changes of $NH_4HCO_3$ at pH 7.0. Chemical deglycosylation with TFMS can result in modifications to the treated protein including methylation, succinimide formation and isomerization of aspartate residues (Douglass et al. (2001) *J. Protein Chem.* 20(7):571-6).

Chemical deglycosylation by HF (Sojar et al. (1987) *Methods Enzymol.* 138:341-50): The reaction is carried out in a closed reaction system such as that can be obtained from Peninsula Laboratories, Inc. 10 mg GILT-GUS is vacuum dried and placed in a reaction vessel which is then connected to the HF apparatus. After the entire HF line is evacuated, 10 mL anhydrous HF is distilled over from the reservoir with stirring of the reaction vessel. The reaction is continued for 1-2 hours at 0° C. Afterwards, a water aspirator removes the HF over 15-30 minutes. Remaining traces of HF are removed under high vacuum. The reaction mixture is dissolved in 2 mL 0.2M NaOH to neutralize any remaining HF and the pH is readjusted to 7.5 with cold 0.2M HCl.

Enzymatic deglycosylation (Thotakura et al. (1987) *Methods Enzymol.* 138:350-9): N-linked carbohydrates can be removed completely from glycoproteins using protein N-glycosidase (PNGase) A or F. In one embodiment, a glycoprotein is denatured prior to treatment with a glycosidase to facilitate action of the enzyme on the glycoprotein; the glycoprotein is subsequently refolded as discussed in the "In vitro refolding" section above. In another embodiment, excess glycosidase is used to treat a native glycoprotein to promote effective deglycosylation. Some cell types, such as the CHO-derived Lec1 cell line, produce glycoproteins with reduced or simplified glycosylation, facilitating subsequent enzymatic deglycosylation as described in Example 15D.

In the case of a targeted therapeutic protein that is actually underglycosylated, it is possible that the reduced glycosylation will reveal protease-sensitive sites on the targeted therapeutic protein, which will diminish the half-life of the protein. N-linked glycosylation is known to protect a subset of lysosomal enzymes from proteolysis (Kundra et al. (1999) *J. Biol. Chem.* 274(43):31039-46). Such protease-sensitive sites are preferably engineered out of the protein (e.g. by site-directed mutagenesis). As discussed below, the risk of revealing either a protease-sensitive site or a potential epitope can be minimized by incomplete deglycosylation or by modifying the carbohydrate structure rather than omitting the carbohydrate altogether.

Modification of Carbohydrate Structure or Partial Deglycosylation

In some embodiments, the therapeutic protein is partially deglycosylated. For example, the therapeutic protein can be treated with an endoglycosidase such as endoglycosidase H, which cleaves N-linked high mannose carbohydrate but not complex type carbohydrate leaving a single GlcNAc residue linked to the asparagine. A therapeutic protein treated in this way will lack high mannose carbohydrate, reducing interaction with the hepatic mannose receptor. Even though this receptor recognizes terminal GlcNAc, the probability of a productive interaction with the single GlcNAc on the protein surface is not as great as with an intact high mannose structure. If the therapeutic protein is produced in mammalian cells, any complex carbohydrate present on the protein will remain unaffected by the endoH treatment and may be terminally sialylated, thereby diminishing interactions with hepatic carbohydrate recognizing receptors. Such a protein is therefore likely to have increased half-life. At the same time, steric hindrance by the remaining carbohydrate should shield potential epitopes on the protein surface from the immune system and diminish access of proteases to the protein surface (e.g. in the protease-rich lysosomal environment).

Figure 9A:
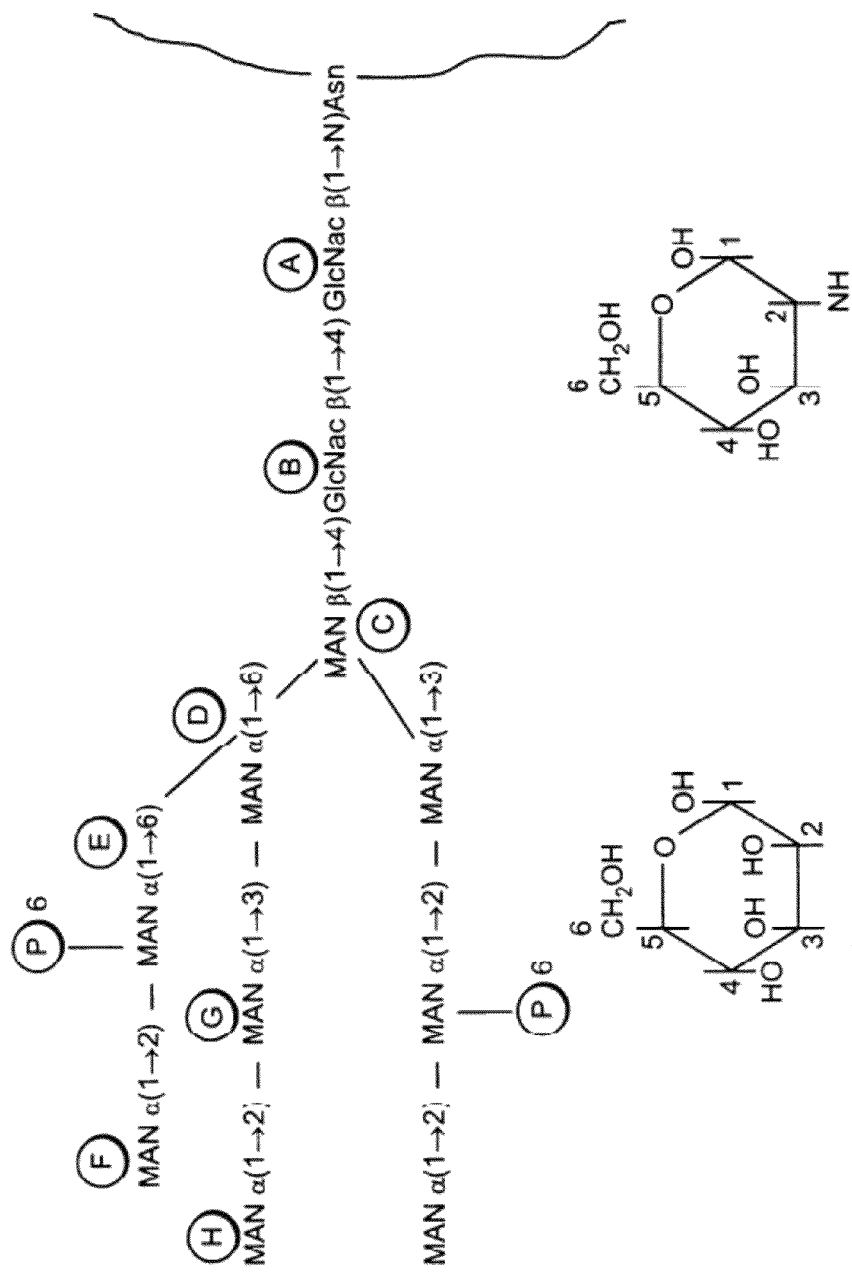
Figure 9B:
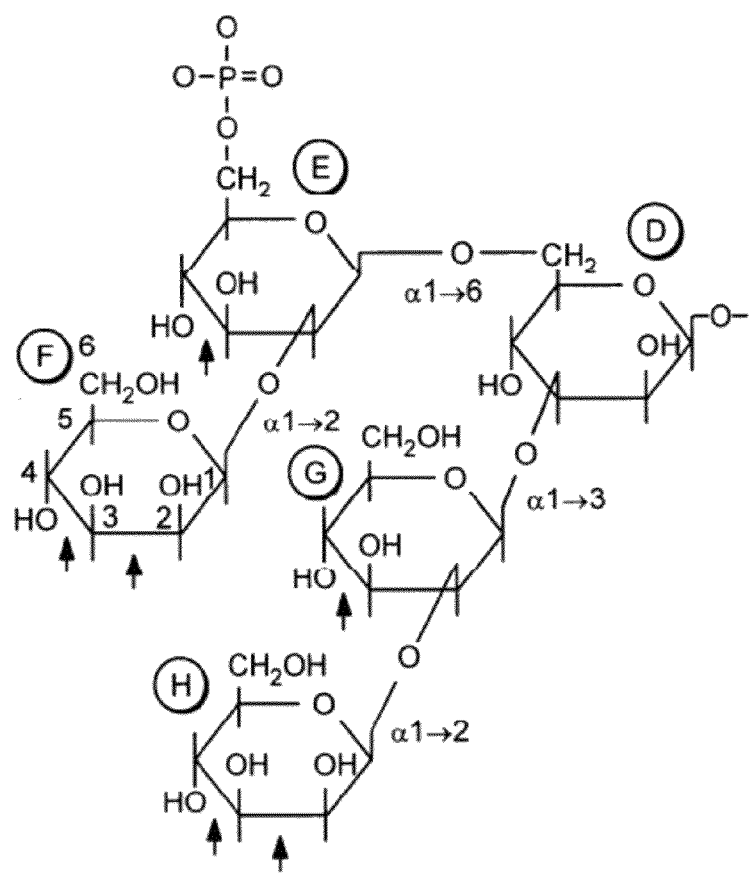

In other embodiments, glycosylation of a therapeutic protein is modified, e.g. by oxidation, reduction, dehydration, substitution, esterification, alkylation, sialylation, carbon-carbon bond cleavage, or the like, to reduce clearance of the therapeutic protein from the blood. In some preferred embodiments, the therapeutic protein is not sialylated. For example, treatment with periodate and sodium borohydride is effective to modify the carbohydrate structure of most glycoproteins. Periodate treatment oxidizes vicinal diols, cleaving the carbon-carbon bond and replacing the hydroxyl groups with aldehyde groups; borohydride reduces the aldehydes to hydroxyls. Many sugar residues include vicinal diols and, therefore, are cleaved by this treatment. As shown in FIG. 9A, a protein may be glycosylated on an asparagine residue with a high mannose carbohydrate that includes N-acetylglucosamine residues near the asparagine and mannose residues elsewhere in the structure. As shown in FIG. 9B, the terminal mannose residues have three consecutive carbons with hydroxyl groups; both of the carbon-carbon bonds involved are cleaved by periodate treatment. Some nonterminal mannose residues also include a vicinal diol, which would similarly be cleaved. Nevertheless, while this treatment converts cyclic carbohydrates into linear carbohydrates, it does not completely remove the carbohydrate, minimizing risks of exposing potentially protease-sensitive or antigenic polypeptide sites.

The half-life of lysosomal enzyme β-glucuronidase is known to increase more than ten-fold after sequential treatment with periodate and sodium borohydride (Houba et al. (1996) *Bioconjug. Chem.* 7(5):606-11; Stahl et al (1976) *PNAS* 73:4045-4049; Achord et al. (1977) *Pediat. Res.* 11:816-822; Achord et al. (1978) *Cell* 15(1):269-78). Similarly, ricin has been treated with a mixture of periodate and sodium cyanoborohydride (Thorpe et al. (1985) *Eur. J. Biochem.* 147:197). After injection into rats, the fraction of ricin adsorbed by the liver decreased from 40% (untreated ricin) to 20% (modified ricin) of the injected dose with chemical treatment. In contrast, the amount of ricin in the blood increased from 20% (untreated ricin) to 45% (treated ricin). Thus, the treated ricin enjoyed a wider tissue distribution and longer half-life in the circulation.

A β-glucuronidase construct (or other glycoprotein) coupled to a targeting moiety of the invention when deglycosylated or modified by sequential treatment with periodate and sodium borohydride should enjoy a similar (e.g. more than two-fold, more than four-fold, or more than ten-fold) increase in half life while still retaining a high affinity for the cation-independent M6P receptor, permitting targeting of the construct to the lysosome of all cell types that possess this receptor. The construct is also predicted to cross the blood brain barrier efficiently. In contrast, if a β-glucuronidase preparation that relies on M6P for lysosomal targeting is deglycosylated or treated with periodate and sodium borohydride, it will enjoy an elevated serum half-life but will be unable to target the lysosome since the M6P targeting signal will have been modified by the treatment.

Carbohydrate modification by sequential treatment with periodate and sodium borohydride can be performed as follows: Purified GILT-GUS is incubated with 40 mM $NaIO_4$ in 50 mM sodium acetate pH 4.5 for 2 hours at 4° C. The reaction is stopped by addition of excess ethylene glycol and unreacted reagents are removed by passing the reaction mix over Sephadex G-25M equilibrated with PBS pH 7.5. This treatment is followed by incubation with 40 mM $NaBH_4$ in PBS at pH 7.5 and 37° C. for three hours and then for one hour at 4° C. Passing the reaction mixture over a Sephadex G-25M column eluted with PBS at pH 7.5 terminates the reaction.

Another protocol for periodate and sodium borohydride treatment is described in Hickman et al. (1974) *BBRC* 57:55-61. The purified protein is dialyzed into 0.01M sodium phosphate pH 6.0, 0.15 M NaCl. Sodium periodate is added to a final concentration of 0.01M and the reaction proceeds at 4° C. in the dark for at least six hours. Treatment of β-hexosaminidase with periodate under these conditions is sufficient to prevent uptake of the protein by fibroblasts; uptake is normally dependent on M6P moieties on the β-hexosaminidase with the M6P receptor on the fibroblast cell surface. Thus, periodate oxidation modifies M6P sufficiently to abolish its ability to interact with the M6P receptor.

Alternatively, the carbohydrate can be modified by treatment with periodate and cyanoborohydride in a one step reaction as disclosed in Thorpe et al. (1985) *Eur. J. Biochem.* 147:197-206.

The presence of carbohydrate in a partially deglycosylated protein or a protein with a modified glycosylation pattern should shield potential polypeptide epitopes that might be uncovered by complete absence of glycosylation. In the event that a therapeutic protein does provoke an immune response, immunosuppressive therapies can be used in conjunction with the therapeutic protein (Brooks (1999) *Molecular Genetics and Metabolism* 68:268-275). For example, it has been reported that about 15% of Gaucher disease patients treated with alglucerase developed immune responses (Beutler et al. in *The Metabolic and Molecular Bases of Inherited Disease*, 8th ed. (2001), Scriver et al. eds., pp. 3635-3668). Fortunately, many (82/142) of the patients that produced antibody against alglucerase became tolerized by the normal treatment regimen (Rosenberg et al. (1999) *Blood* 93:2081-2088). Thus, to benefit the small minority of patients who may develop an immune response, a patient receiving a therapeutic protein also receives an immunosuppressive therapy in some embodiments of the invention.

Testing

To verify that a protein is underglycosylated, it can be tested by exposure to Con A. An underglycosylated protein is expected to demonstrate reduced binding to Con A-Sepharose when compared to the corresponding fully glycosylated protein.

An actually underglycosylated protein can also be resolved by SDS-PAGE and compared to the corresponding fully-glycosylated protein. For example, chemically deglycosylated GUS-GILT can be compared to untreated (glycosylated) GUS-GILT and to enzymatically deglycosylated GUS-GILT prepared with PNGase A. The underglycosylated protein is expected to have a greater mobility in SDS-PAGE when compared to the fully glycosylated protein.

Underglycosylated targeted therapeutic proteins display uptake that is dependent on the targeting domain. Underglycosylated proteins should display reduced uptake (and, preferably, substantially no uptake) that is dependent on mannose or M6P. These properties can be experimentally verified in cell uptake experiments.

For example, a GUS-GILT protein synthesized in mammalian cells and subsequently treated with periodate and borohydride can be tested for functional deglycosylation by testing M6P-dependent and mannose-dependent uptake. To demonstrate that M6P-dependent uptake has been reduced, uptake assays are performed using GM4668 fibroblasts. In the absence of competitor, treated and untreated enzyme will each display significant uptake. The presence of excess IGF-II substantially reduces uptake of treated and untreated enzyme, although untreated enzyme retains residual uptake via a M6P-dependent pathway. Excess M6P reduces the uptake of untreated enzyme, but is substantially less effective at reducing the uptake of functionally deglycosylated protein. For treated and untreated enzymes, the simultaneous presence of both competitors should substantially abolish uptake.

Uptake assays to assess mannose-dependent uptake are performed using J774-E cells, a mouse macrophage-like cell line bearing mannose receptors but few, if any, M6P receptors (Diment et al. (1987) *J. Leukocyte Biol.* 42:485-490). The cells are cultured in DMEM, low glucose, supplemented with 10% FBS, 4 mM glutamine, and antibiotic, antimycotic solution (Sigma, A-5955). Uptake assays with these cells are performed in a manner identical to assays performed with fibroblasts. In the presence of excess M6P and IGF-II, which will eliminate uptake due to any residual M6P/IGF-II receptor, fully glycosylated enzyme will display significant uptake due to interaction with the mannose receptor. Underglycosylated enzyme is expected to display substantially reduced uptake under these conditions. The mannose receptor-dependent uptake of fully glycosylated enzyme can be competed by the addition of excess (100 µg/mL) mannan.

Pharmacokinetics of deglycosylated GUS-GILT can be determined by giving intravenous injections of 20,000 enzyme units to groups of three MPSVII mice per timepoint. For each timepoint 50 µL of blood is assayed for enzyme activity.

Example 15A

Deglycosylation of GUSΔC18-GILTΔ1-7

GUSΔC18-GILTΔ1-7 was treated with endoglycosidase F1 to reduce glycosylation. Specifically, 0.5 mg of GUSΔC18-GILTΔ1-7 were incubated with 25 μL of endoglycosidase F1 (Prozyme, San Leandro, Calif.) for 7.5 hours at 37° C. in a final volume of 250-300 μL of 50 mM phosphate buffer pH 5.5. After incubation, the GUSΔC18-GILTΔ1-7 was repeatedly concentrated in a Centricon spin concentrator with a 50 kD molecular weight cut-off to separate the GUSΔC18-GILTΔ1-7 from the endoglycosidase F1.

In a separate experiment, GUSΔC18-GILTΔ1-7 was treated both with endoglycosidase F1 and with endoglycosidase F2. Specifically, 128 μL of GUSΔC18-GILTΔ1-7 (7.79 million units/mL) were incubated with 12.8 μL of each endoglycosidase (each from Prozyme) in a final volume of 325 μl, of 50 mM phosphate, pH 5.5, for 6 hours at 37° C., followed by purification by spin concentrators as described above.

Figure 10:

One to three micrograms of the GUSΔC18-GILTΔ1-7 treated with endoglycosidase F1 was resolved by electrophoresis through a 7.5% polyacrylamide gel. The gel was stained with coomassie brilliant blue dye and is shown in FIG. 10. ΔΔN refers to untreated GUSΔC18-GILTΔ1-7. HBG5 refers to untagged human β-glucuronidase, which has a lower molecular weight and higher mobility than the tagged GUSΔC18-GILTΔ1-7. The treated GUSΔC18-GILTΔ1-7 is shown as ΔΔN+F1, and has, on average, a modestly increased mobility compared to the untreated protein, consistent with at least partial deglycosylation of the protein. A further increase in mobility is observed in samples of GUSΔC18-GILTΔ1-7 treated with both endoglycosidase F1 and endoglycosidase F2 (data not shown), further suggesting that endoglycosidase F1 only partially deglycosylates the protein.

Example 15B

In Vitro Uptake of Deglycosylated Protein

Cultured mucopolysaccharidosis VII skin fibroblast GM 4668 cells were used to assess uptake of GUSΔC18-GILTΔ1-7 with or without treatment with endoglycosidase F1. Specifically, the cells were grown in DMEM low glucose+4 mM glutamine+antibiotic/antimycotic+15% FBS (not heat inactivated) at 37° C. in 5% $CO_2$. Passaging of cells was done with a scraper. Cells were cultured to about 50-80% confluency in T75 flasks (75 cm$^2$ surface area). The day before the uptake experiment, the cells were split into 12-well tissue culture plates (46 cm$^2$ total surface area). The cells were permitted to re-attach for 1-4 hours, then the medium was changed before permitting the cells to grow overnight.

Uptake experiments were performed in triplicate. The uptake medium is DMEM low glucose+2% BSA (Sigma A-7030)+4 mM glutamine+antibiotic/antimycotic. The final volume of uptake medium+enzyme is 1 mL/well. The cells were washed in uptake medium and incubated in uptake medium+β-glucuronidase (M6P), untreated GUSΔC18-GILTΔ1-7 (GILT), or GUSΔC18-GILTΔ1-7 after treatment with endoglycosidase F1 (GILT+F1) (approximately 4000 units) with or without 2 mM mannose-6-phosphate (+M6P) or 2.86 mM recombinant IGF-II (+Tag) for 3 hours. The medium was then removed, each well was washed with 4×1 mL PBS, and the cells were incubated for 5-10 minutes at room temperature with 200 μL lysis buffer (100 mL lysis buffer: 1 mL of 1M Tris pH 7.5, 2 mL NaCl, 1 mL 0.5M EDTA, 96 mL water; add 10 μL of NP-40 for every mL of lysis buffer immediately prior to use). All lysate was transferred into microfuge tubes and spun for 5 minutes at full speed. 10 μL of lysates were assayed in duplicate for GUS activity. 10 μL of lysates were assayed in triplicate for total protein concentration using Pierce's Micro BCA kit. 2 μL of the uptake medium was also assayed in duplicate for GUS activity.

Figure 11:
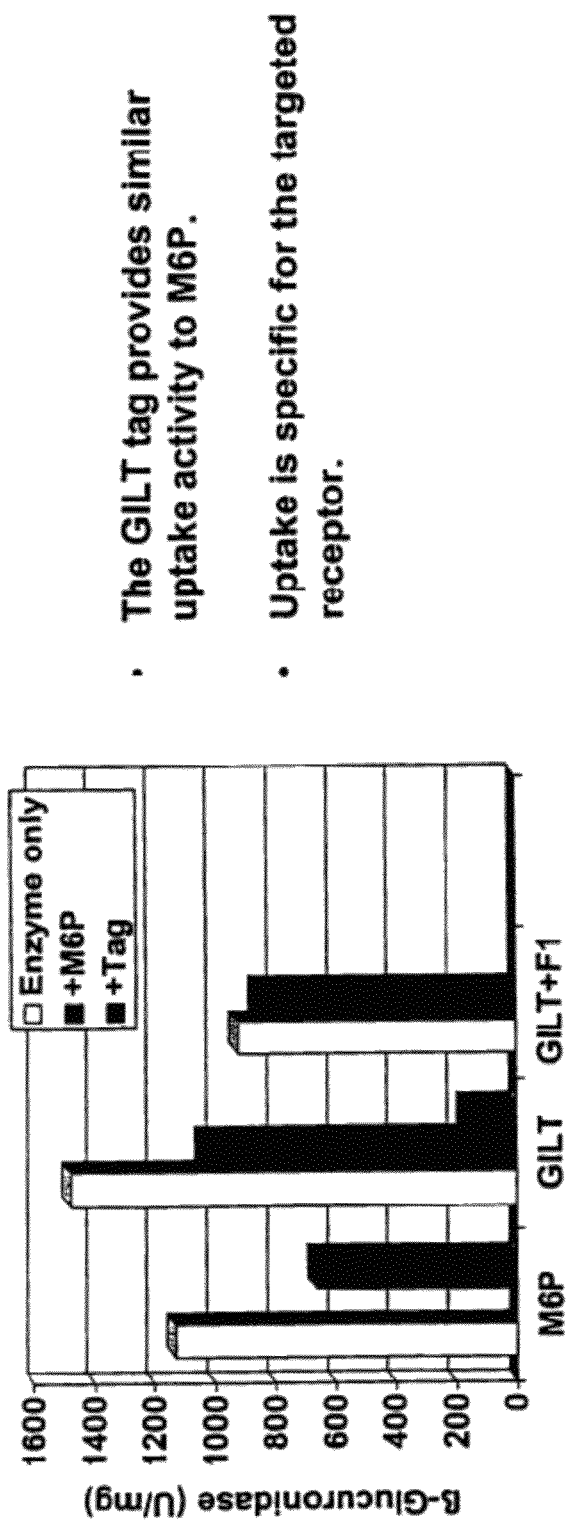

As shown in FIG. 11, GUSΔC18-GILTΔ1-7, with or without treatment with endoglycosidase F1, is taken up efficiently by the fibroblasts, even in the presence of mannose-6-phosphate, whereas the uptake of the untagged β-glucuronidase is essentially eliminated by the presence of the mannose-6-phosphate competitor. In contrast, IGF-II successfully inhibited uptake of the GUSΔC18-GILTΔ1-7 protein, essentially abolishing uptake of the protein treated with endoglycosidase F1, indicating that the uptake of the treated protein is indeed mediated by the GILTΔ1-7 tag.

Example 15C

In Vivo Uptake Experiments

Figure 12:
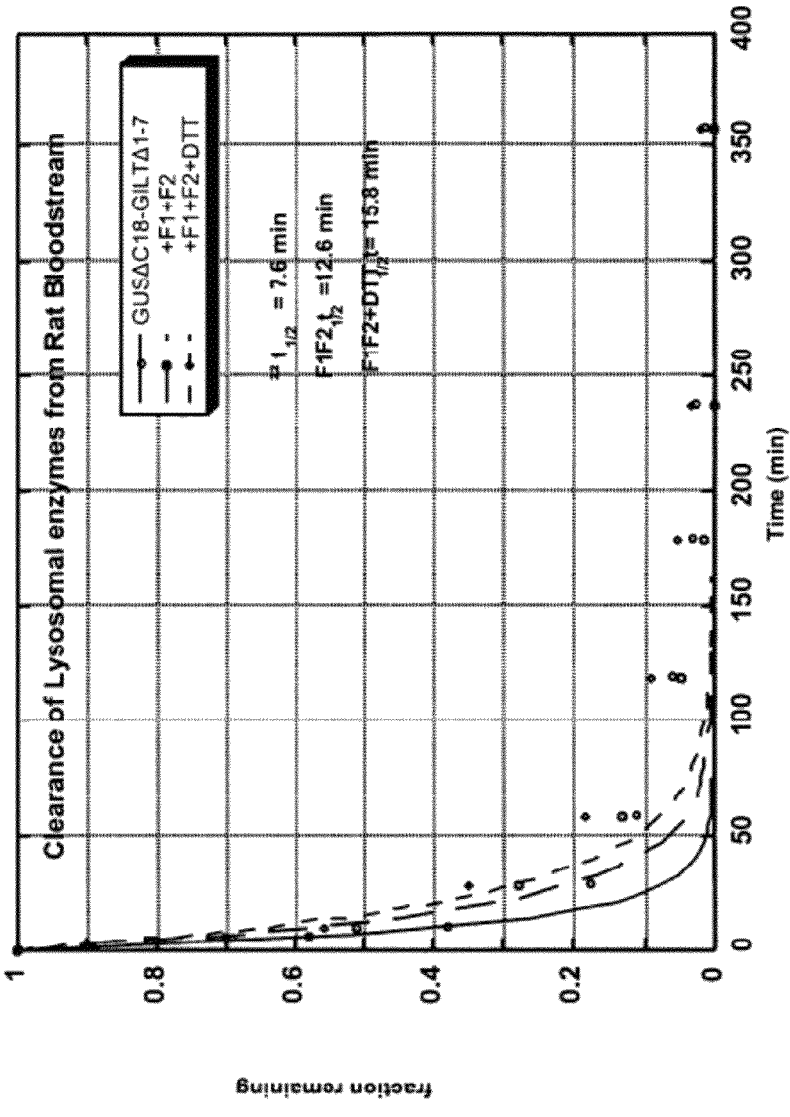

To determine the half-life of the treated and untreated proteins in circulation, experiments were done using cannulated Sprague-Dawley rats. 100,000-150,000 units of GUSΔC18-GILTΔ1-7 were administered intravenously, the protein was untreated (GUSΔC18-GILTΔ1-7), treated with endoglycosidase F1 and endoglycosidase F2 (+F1+F2), or treated with endoglycosidase F1 and endoglycosidase F2 followed by a 45 minute incubation with 5 mM dithiothreitol in phosphate-buffered saline at 37° C. to disrupt the GILT tag. Blood was withdrawn through the cannula at regular intervals thereafter, treated at 60° C. for one hour to inactivate endogenous rat glucuronidase, and assayed for glucuronidase activity. The results are shown in FIG. 12. The half-life of the protein was estimated by fitting the early time points to an equation in the form of $y=e^{-kt}$ using KaleidaGraph v.3.52. The half-life of the untreated protein is estimated at 8 minutes. Treatment with endoglycosidases F1 and F2 increases the half-life to about 13 minutes, consistent with improved evasion of the reticuloendothelial clearance system upon deglycosylation. Treatment with DTT should interfere with uptake of the tagged enzyme via the IGF-II receptor and further increases the half-life of the endoglycosidase F1/endoglycosidase F2 treated protein to about 16 minutes.

Figure 13:
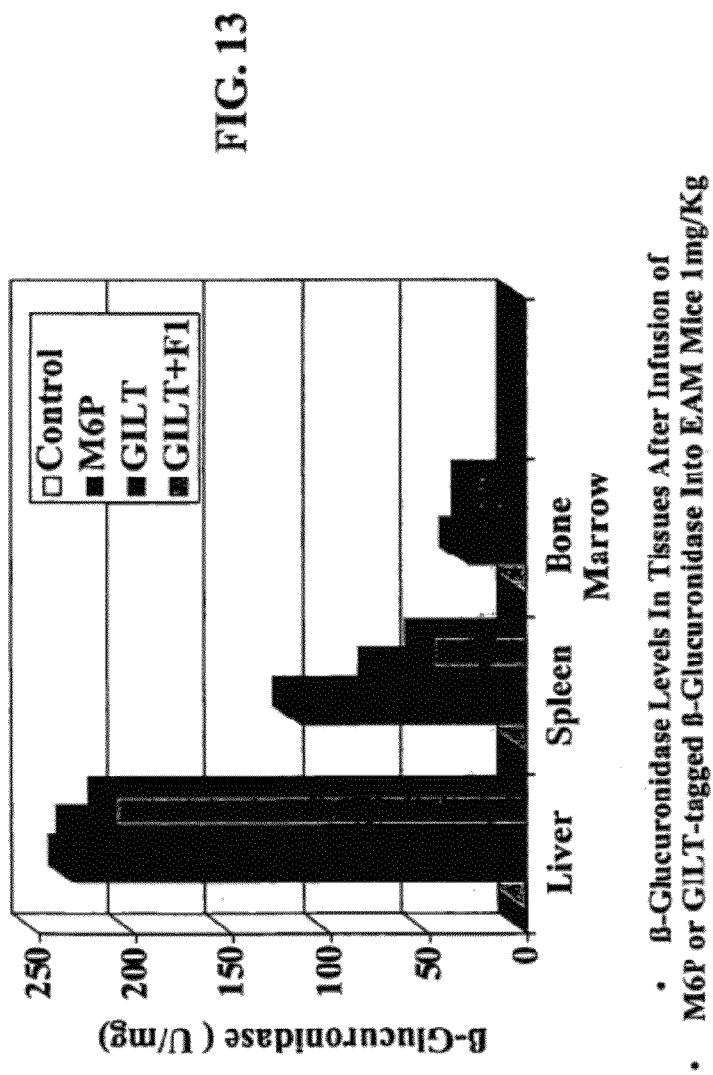
Figure 14:
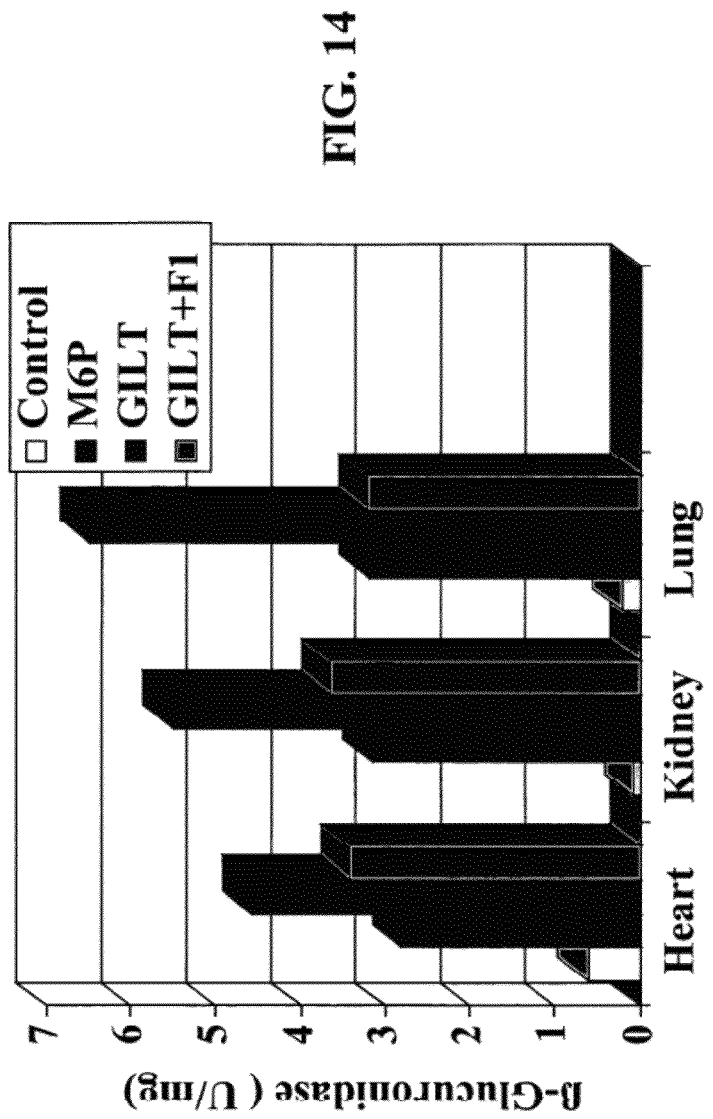

As illustrated in FIGS. 13-15, the delivery of untreated GUSΔC18-GILTΔ1-7 (GILT), treated with endoglycosidase F1 (GILT+F1) to tissues in vivo was assessed and compared to delivery of untagged β-glucuronidase (M6P). All proteins were produced in CHO cells. 1 mg of M6P, GILT, or GILT+F1 per kg of body weight was administered to MPSVII mice by infusing the protein into the tail vein. Control animals (Control) were infused with buffer alone. Twenty-four hours later the animals were sacrificed and tissue samples were collected for analysis. The data depicted in FIGS. 13-15 result from infusion of 6-7 animals with each enzyme.

FIG. 13 shows the levels of the various enzymes detected in liver, spleen, and bone marrow. Macrophages are abundant in these tissues and clear the enzymes from the circulation, primarily through the high mannose receptor. Because GILT+F1 should have less high mannose carbohydrate than the untreated enzymes, less accumulation in these tissues is expected. In the liver and bone marrow, accumulation of the endoglycosidase F1 treated enzyme was almost as great accumulation of the untreated enzyme. In the spleen, however, there was a noticeable reduction in accumulation of GILT+F1. Both the treated and untreated GUSΔC18-GILTΔ1-7 proteins reached heart, kidney, and lung tissues efficiently, with accumulation equal to or exceeding accumulation of untagged β-glucuronidase, as shown in FIG. 14. Thus, the GILTΔ1-7 tag permits targeting to the same tissues as mannose-6-phosphate, with equal or better efficiency. Furthermore, as shown in FIG. 15, both the treated and untreated GUSΔC18-GILTΔ1-7 proteins reached brain tissue at levels exceeding levels observed for untagged β-glucuronidase, although accumulation levels in brain tissue were distinctly lower than the accumulation levels in other tissues.

Selected tissues from infused animals were also subjected to histology to detect β-glucuronidase as described in Wolf et al. (1992) *Nature* 360:749-753. β-glucuronidase is detected as a red stain; nuclei are stained blue. The results of the liver histology for untagged β-glucuronidase (HGUS), untreated GUSΔC18-GILTΔ1-7 (Dd-15gilt), and GUSΔC18-GILTΔ1-7 treated with endoglycosidase F1 (dd15F1) are shown in FIG. 16. On the HGUS slide, the elongate Kupffer cells stain an intense red, whereas the more compact cells, primarily hepatocytes, contain relatively little red stain, and appear in the figure as a blue nucleus surrounded by a whitish area. In contrast, the hepatocytes of the other two slides, containing untreated or treated GUSΔC18-GILTΔ1-7, stain rather intensely, as evidenced by the sharply reduced number of blue nuclei immediately surrounded by white. This helps to explain why even the GUSΔC18-GILTΔ1-7 treated with endoglycosidase F1 still localized significantly to the liver. The tagged protein reaches a more diverse subset of cell types in the liver. Thus, while it may be less subject to clearance by high mannose receptors, the protein nevertheless reaches the liver in quantity because it targets a greater variety of cells.

Additional histology data are shown in FIGS. 17-19. FIG. 17 shows localization to the glomeruli of the kidney. Although histochemical staining is not often quantitative, slides from animals infused with GUSΔC18-GILTΔ1-7 (shown as Dd-15 (untreated) and F1 (treated with endoglycosidase F1) reproducibly show a more intense staining in the glomeruli than slides from animals infused with the untagged protein. As shown in FIGS. 18 and 19, the tagged protein, whether (dd-15F1) or not (dd-15) treated with endoglycosidase F1, appears capable of reaching the same cells that untagged protein (HGUS) reaches.

Example 15D

Deglycosylated, Lec1-Produced Proteins

GUSΔC18-GILTΔ1-7 protein was produced in Lec1 cells, treated with endoglycosidase F1, and tested in vitro and in vivo for targeting and uptake. The Lec1 cells, which were procured from the ATCC (ATCC#CRL1735), are CHO-derived cells lacking β-1,2-N-acetylglucosaminyl transferase I (GlcNAc-T1) activity (Stanley et al., (1975) *Cell* 6(2):121-8; Stanley et al., (1975) *PNAS* 72(9):3323-7). GlcNAc-T1 adds N-acetylglucosamine to the core oligosaccharide $Man_5$-$GlcNAc_2$-Asn. This addition is an initial, obligatory step in the synthesis of complex and hybrid N-linked oligosaccharides. Thus, glycoproteins from Lec1 cells lack complex and hybrid oligosaccharides. Although Lec1 cells do produce glycoproteins bearing high mannose oligosaccharides, these structures are amenable to removal with endoglycosidase F1. Accordingly, production of a GILT-tagged protein in Lec1 cells with subsequent endoglycosidase F1 treatment should yield a deglycosylated protein. When injected into the bloodstream of an animal, such a protein should avoid clearance by mannose receptors in liver-resident macrophage and accumulate to greater levels in target tissues.

A β-GUSΔC18-GILTΔ1-7 cassette in expression plasmid pCXN was electroporated into Lec1 cells at 50 μF and 1,200 V in a 0.4-cm cuvette. Cells were propagated in DMEM supplemented with 15% FBS, 1.2 mM glutamine, 50 μg/mL proline, and 1 mM pyruvate. Selection of colonies and amplification was mediated by 400 μg/mL G418 for 2-3 weeks. Confluent cultures of clonal lines were placed in collection medium (Weymouth medium supplemented with 2% FBS, 1.2 mM glutamine, and 1 mM pyruvate). Medium containing the secreted recombinant enzyme was collected every 24-72 hours. One line, Lea-18, was selected for enzyme production as it produced the highest yields of recombinant enzyme.

Recombinant enzyme from Led cells was affinity purified using anti-human β-glucuronidase-Affigel 10 resin as described in Example 10. The uptake of the Lec1-produced, GILT-tagged enzyme was compared to that of CHO-produced tagged or untagged enzymes. As shown in Table 9, the tagged, Lec1-produced enzyme exhibited more M6P-independent uptake than the corresponding tagged, CHO-produced enzyme and much more than an untagged enzyme. Treatment of the Lec1-produced enzyme with endoglycosidase F1 eliminated M6P-independent binding but not IGF-II-dependent binding. As shown in FIG. 21, SDS-PAGE of endoglycosidase F1 treated and untreated Lec1-produced enzymes showed a distinct mobility shift approaching the mobility of a PNGase F treated enzyme, which should be completely deglycosylated. This suggests treatment of Lec1-produced enzyme with endoglycosidase F1 causes a significant loss of glycosylation. In contrast, neither the CHO-produced enzyme nor the HEK-produced enzyme showed a marked shift in mobility after treatment with endoglycosidase F1.

TABLE 9

Comparison of uptake +/− M6P of CHO-produced untagged human β-glucuronidase (HBG5) and ΔΔ and Lec-1-18-produced ΔΔ by MPS VII fibroblasts

| Enzyme (cell line) | −M6P | +M6P | % non-M6P Mediated Uptake |
|---|---|---|---|
| HBG5 (CHO) | 251 | 7 | 2.7% |
| ΔΔ (CHO) | 207 | 98 | 47% |
| ΔΔ (Lec1-18) | 230 | 150 | 65% |

The endoglycosidase F1-treated Lec1 and CHO-produced enzymes and the untreated HEK 293-produced enzyme were each infused into 3 immunotolerant MPSVII mice (Sly et al. (2001) *PNAS* 98:2205-2210) at a dose of 1 mg/kg. 24 hours later, the mice were sacrificed and tissues were assayed for enzyme activity. As shown in FIG. 22, the Lec1-produced enzyme accumulated less in the liver and more in the target tissues of heart, muscle, and kidney than did the CHO-produced enzyme. HEK 293-produced enzyme showed slightly higher accumulation of enzyme in the heart, kidney and muscle than did the Lec1-produced enzyme.

The measured accumulation of the enzyme in the target tissues depends both on the efficiency of targeting to the tissue and on the rate of clearance of the enzyme from the tissue. If, upon proper targeting to the lysosome, the Lec1-produced enzyme is degraded more slowly than the CHO-produced enzyme, this could account for the higher observed levels of accumulation. On the other hand, a more rapid degradation of the Lec1-produced enzyme could mask a magnified targeting efficacy. To address this possibility, the half lives of treated and untreated Lec1- and CHO-produced enzymes were tested in an uptake assay with MPSVII fibroblasts. The fibroblasts were incubated with enzyme for 3 hours, the cells were washed and placed in fresh media that were changed daily. For each enzyme, duplicate wells were lysed on days 0, 3 and 7. The fraction of enzyme remaining was plotted against time and the data were fit to an exponential equation. As shown in FIG. 23, the endoglycosylase F1-treated, Lec 1-produced enzyme was found to have a half-life similar to that of HBG5 and slightly less than that of the CHO-produced enzyme in human fibroblasts.

INCORPORATION BY REFERENCE

The disclosure of each of the patent documents, scientific publications, and Protein Data Bank records disclosed herein, and U.S. Provisional Application No. 60/250,446, filed Nov. 30, 2000; U.S. Provisional Application 60/287,531, filed Apr. 30, 2001; U.S. Provisional Application 60/290,281, filed May 11, 2001; U.S. Provisional Application 60/304,609, filed Jul. 10, 2001; U.S. Provisional Application No. 60/329,461, filed Oct. 15, 2001; International Patent Application Serial No. PCT/US01/44935, filed Nov. 30, 2001; U.S. Provisional Application No. 60/351,276, filed Jan. 23, 2002; U.S. Ser. Nos. 10/136,841 and 10/136,639, filed Apr. 30, 2002, U.S. Ser. No. 60/384,452, filed May 29, 2002; U.S. Ser. No. 60/386,019, filed Jun. 5, 2002; and U.S. Ser. No. 60/408,816, filed Sep. 6, 2002, are incorporated by reference into this application in their entirety.

---

We claim:

1. An underglycosylated targeted therapeutic fusion protein comprising: a lysosomal enzyme; and a lysosomal targeting domain that binds an extracellular domain of human cation-independent mannose-6-phosphate receptor in a mannose-6-phosphate-independent manner, wherein the lysosomal targeting domain is mature human IGF-II or a mutein of mature human IGF-II having an amino acid sequence at least 70% identical to mature human IGF-II, and (i) does not bind a mutein in which amino acid 1572 of the human cation-independent mannose-6-phosphate receptor is changed from isoleucine to threonine; or (ii) binds the mutein with a dissociation constant at least ten times the dissociation constant for binding the extracellular domain of human cation-independent mannose-6-phosphate receptor.

2. The targeted therapeutic fusion protein of claim 1, wherein the targeted therapeutic fusion protein is deglycosylated.

3. The targeted therapeutic fusion protein of claim 2, wherein the targeted therapeutic fusion protein is deglycosylated by treatment with periodic acid.

* * * * *